United States Patent
Lee et al.

(10) Patent No.: US 12,351,605 B2
(45) Date of Patent: Jul. 8, 2025

(54) OPTICALLY CONTROLLABLE FGFR STIMULATION USING WIRELESS CONTROLLED CELLULAR LIGHTING SYSTEM

(71) Applicant: THE JOHNS HOPKINS UNIVERSITY, Baltimore, MD (US)

(72) Inventors: Gabsang Lee, Ellicott City, MD (US); Hyesoo Kim, Baltimore, MD (US); InYoung Choi, Baltimore, MD (US); HoTae Lim, Baltimore, MD (US); Alex V. Huynh, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 478 days.

(21) Appl. No.: 17/152,220

(22) Filed: Jan. 19, 2021

(65) Prior Publication Data
US 2021/0221858 A1 Jul. 22, 2021

Related U.S. Application Data

(60) Provisional application No. 62/962,246, filed on Jan. 17, 2020.

(51) Int. Cl.
| | |
|---|---|
| C07K 14/405 | (2006.01) |
| C07K 14/71 | (2006.01) |
| C12M 1/00 | (2006.01) |
| C12N 5/0735 | (2010.01) |
| C12N 5/074 | (2010.01) |
| C12N 13/00 | (2006.01) |

(52) U.S. Cl.
CPC ............ *C07K 14/405* (2013.01); *C07K 14/71* (2013.01); *C12M 31/10* (2013.01); *C12N 5/0606* (2013.01); *C12N 5/0696* (2013.01); *C12N 13/00* (2013.01); *C07K 2319/02* (2013.01)

(58) Field of Classification Search
None
See application file for complete search history.

(56) References Cited

U.S. PATENT DOCUMENTS

| | | |
|---|---|---|
| 5,785,116 A | 7/1998 | Wagner |
| 6,307,024 B1 | 10/2001 | Novak et al. |
| 6,337,435 B1 | 1/2002 | Chu et al. |
| 9,091,447 B2 | 7/2015 | Arrigoni et al. |
| 9,839,698 B2 | 12/2017 | Yang et al. |
| 10,604,553 B2 | 3/2020 | Heo et al. |
| 10,711,242 B2 | 7/2020 | Deisseroth et al. |
| 2003/0082809 A1 | 5/2003 | Quail et al. |
| 2005/0095266 A1 | 5/2005 | Perichaud et al. |
| 2006/0004306 A1 | 1/2006 | Altshuler et al. |
| 2009/0057000 A1 | 3/2009 | Kraus et al. |
| 2009/0186334 A1 | 7/2009 | Young et al. |
| 2011/0207209 A1 | 8/2011 | Hammons et al. |
| 2011/0216953 A1 | 9/2011 | Callahan et al. |
| 2012/0004124 A1 | 1/2012 | Schultze et al. |
| 2014/0099662 A1 | 4/2014 | Ando et al. |
| 2015/0203837 A1 | 7/2015 | Heo et al. |
| 2016/0326219 A1* | 11/2016 | Riedler ............... G01N 33/5088 |
| 2016/0328216 A1 | 11/2016 | Leonelli et al. |
| 2016/0369222 A1 | 12/2016 | Cho |
| 2017/0146720 A1 | 5/2017 | Yamamoto et al. |
| 2019/0155146 A1 | 5/2019 | Hribar et al. |
| 2020/0140821 A1 | 5/2020 | Elfenbein et al. |
| 2022/0017577 A1 | 1/2022 | Kennedy et al. |
| 2022/0195371 A1 | 6/2022 | Schaffer et al. |
| 2023/0105479 A1 | 4/2023 | Lee et al. |

FOREIGN PATENT DOCUMENTS

| | | |
|---|---|---|
| CA | 2560016 A1 | 10/2005 |
| CN | 106975158 A | 7/2017 |
| CN | 112342241 A | 2/2021 |
| EP | 1964610 A2 | 9/2008 |
| EP | 2682469 B1 | 12/2018 |
| WO | 2013185892 A1 | 12/2013 |
| WO | 2015041219 A1 | 3/2015 |
| WO | 2015086818 A1 | 6/2015 |
| WO | 2020231707 A1 | 11/2020 |
| WO | 2023004031 A1 | 1/2023 |
| WO | 2023235815 A1 | 12/2023 |
| WO | WO-2024119096 A1 | 6/2024 |

OTHER PUBLICATIONS

Liu et al., "Assessing cell-based animal proteins", Science, (Feb. 22, 2019), vol. 363, Issue 6429, pp. 825-827.
Dolgin, "Lab-grown meat gets rare funding boost", Nature, (2019), vol. 566 (7743) pp. 161-162.
Ledford, "Quest to Use CRISPR Gene Editing to Fight Disease Gains Ground", Nature, (Jan. 9, 2020), vol. 577, p. 156.
Stadtmauer et al., "CRISPR-engineered T cells in patients with refractory cancer", Science, (2020), vol. 367, (14 pages).
Xu et al., "CRISPR-Edited Stem Cells in a Patient with HIV and Acute Lymphocytic Leukemia", N. Engl. J. Med., (Sep. 26, 2019), vol. 381, No. 13, pp. 1240-1247.
Anzalone et al., "Search-and-replace genome editing without double-strand breaks or donor DNA", Nature, (Dec. 5, 2019), vol. 576, pp. 149-157.
Kleinstiver et al., "High-fidelity CRISPR-Cas9 nucleases with no detectable genome-wide off-target effects", Nature, (Jan. 28, 2016), vol. 529, pp. 490-495.

(Continued)

*Primary Examiner* — Kara D Johnson
*Assistant Examiner* — Constantina E Stavrou
(74) *Attorney, Agent, or Firm* — Venable LLP; Henry J. Daley

(57) ABSTRACT

The present invention relates to the field of stem cells. More specifically, the present invention provides compositions and methods for using optogenetics to sustain the pluripotency of stem cells. In one embodiment, a vector comprises a nucleotide sequencing encoding a fusion protein comprising the intracellular domain of fibroblast growth factor 1 receptor (FGFR1) and a photoactivatable domain.

17 Claims, 39 Drawing Sheets

Specification includes a Sequence Listing.

(56) References Cited

OTHER PUBLICATIONS

Ran et al., "Double Nicking by RNA-Guided CRISPR Cas9 for Enhanced Genome Editing Specificity", Cell, (2013), vol. 154, pp. 1380-1389.

Dakhore et al.,"Human Pluripotent Stern Cell Culture: Current Status, Challenges, and Advancement", Stem Cells International, (2018), vol. 2018, Article ID 7396905 (18 pages).

Ingles-Prieto et al., "Light-assisted small-molecule screening against protein kinases", Nature Chemical Biology., (Dec. 2015), vol. 11, pp. 952-954.

Reichhart et al., "A Phytochrome Sensory Domain Permits Receptor Activation by Red Light", Angewandte Chemie International Edition., (2016), vol. 55, pp. 6339-6342.

Repina et al., "At Light Speed: Advances in Optogenetic systems for Regulating Cell Signaling and Behavior", Annual Review of Chemical and Biomolecular Engineering., (2017), vol. 8, pp. 13-39.

Chatelle, C. et al., "A Green-Light-Responsive System for the Control of Transgene Expression in Mammalian and Plant Cells", ACS Synthetic Biology, 2018, vol. 7, pp. 1349-1358.

Choi, Iy et al., "Novel culture system via wirelessly controllable optical stimulation of the FGF signaling pathway for human and pig pluripotency", Biomaterials, 2021, vol. 269, No. 120222, pp. pages.

De Santis, R. et al. "Self-organization of Human Dorsal-ventral Forebrain Structures by Light Induced SHH", Nature Communications, 2021, vol. 12, No. 6768, pp. 1-11.

Follain, G. et al., "Seeing is believing: multi-scale spatio-temporal imaging towards in vivo cell biology", Journal of Cell Science, 2016, vol. 130, pp. 1-16.

Golonka, D. et al., "Deconstructing and repurposing the light-regulated interplay between *Arabidopsis phytochromes* and interacting factors", Communications Biology, 2019, vol. 2, No. 448, pp. 1-12.

Gramazio, S. et al., "Light-induced fermenter production of derivatives of the sweet protein monellin is maximized in prestationary *Saccharomyces cerevisiae* cultures", Biotechnology Journal, 2022, vol. 17, No. 2100676, pp. 1-10.

Huang, D. et al., "Temporal Induction of Lhx8 by Optogenetic Control System for Efficient Bone Regeneration", Stem Cell Research & Therapy, 2021, vol. 12, No. 339, pp. 1-14.

Kamm, R. et al., "Perspective: The Promise of Multi-Cellular Engineered Living Systems", APL Bioengineering, Dec. 1, 2018, vol. 2, No. 4, pp. 040901-1-040901-21.

Kupfer, M. et al., "Advanced imaging approaches for regenerative medicine: Emerging technologies for monitoring stem cell fate in vitro and in vivo", Biotechnology Journal, 2015, vol. 10, pp. 1515-1528.

Lee, G., "Establishment of Light-inducible control of stem cell fate", Institute for Cell Engineering Department of Neurology & Neuroscience, Johns Hopkins University School of Medicine, 2018 System IMBA IMP Austria 2018 Vienna Conference (27 pages).

Motta-Mena, L.B. et al., "An optogenetic gene expression system with rapid activation and deactivation kinetics", Nat Chem Biol, 2014, vol. 10, No. 3, pp. 196-202.

Muller, K. et al., "Orthogonal Optogenetic Triple-gene Control in Mammalian Cells", ACS Synthetic Biology, Nov. 21, 2014, vol. 3, No. 11, pp. 796-801.

Polstein, L. et al., "An Engineered Optogenetic Switch for Spatiotemporal Control of Gene Expression, Cell Differentiation, and Tissue Morphogenesis", ACS Synthetic Biology, 2017, vol. 6, 17 pages.

Pomeroy, J.E. et al., "Genetically Encoded Photoactuators and Photosensors for Characterization and Manipulation of Pluripotent Stem Cells", Theranostics, 2017, vol. 7, No. 14, pp. 3539-3558.

Repina, N.A. et al., "Engineered Illumination Devices for Optogenetic Control of Cellular Signaling Dynamics", Cell Reports, 2020, vol. 31, No. 107737, 17 pages.

Repina, N.A. et al., "Optogenetic Control of Wnt Signaling for Modeling Early Embryogneic Patterning With Human Pluripotent Stem Cells", bioRxiv, 2019, pp. 1-61.

Rost, B.R. et al., "Optogenetic Tools for Subcellular Applications in Neuroscience", Neuron, 2017, vol. 96, No. 3, pp. 572-603.

Seale, P. et al., "PRDM16 Controls a Brown Fat/Skeletal Muscle Switch", Nature, 2008, vol. 454, No. 7207, pp. 961-967.

Sokolik, C. et al., "Transcription Factor Competition Allows Embryonic Stem Cells to Distinguish Authentic Signals from Noise", Cell Systems, 2015, vol. 1, pp. 117-129.

Stroh, A. et al., "Tracking Stem Cell Differentiation in the Setting of Automated Optogenetic Stimulation", Stem Cells, 2011, vol. 29, No. 1, pp. 78-88.

Swartz, E.W. et al., "Establishment of a Human Induced Pluripotent Stem Cell-Derived Neuromuscular Co-Culture Under Optogenetic Control", bioRxiv, 2020, 49 pages.

Tang, B. et al., "A Flexible Reporter System for Direct Observation and Isolation of Cancer Stem Cells", Stem Cell Reports, 2015, vol. 4, pp. 155-169.

Vater, C. et al., "Culture media for the differentiation of mesenchymal stromal cells", Acta Biomaterialia, 2011, vol. 7, pp. 463-477.

Vizoso, M. et al., "A Doxycycline- and Light-inducible Cre Recombinase Mouse Model for Optogenetic Genome Editing", Nature Communications, Oct. 28, 2022, vol. 13, No. 1, pp. 1-15.

Walker, E.J. et al., "Transcriptomic changes during TGF-β-mediated differentiation of airway fibroblasts to myofibroblasts", Scientific Reports, 2019, vol. 9, No. 20377, pp. 1-14.

Wang, H. et al., "Mini Photobioreactors for in Vivo Real Time Characterization and Evolutionary Tuning of Bacterial Optogenetic Circuit", ACS Synth Biol., 2017, vol. 6, No. 9, 14 pages.

Weinberg, B.H. et al., "High-Performance Chemical- And Light-Inducible Recombinases in Mammalian Cells and Mice", Nature Communications, Oct. 24, 2019, vol. 10, No. 1, pp. 1-10.

Wu, J.Y. et al., "Directed Differentiation of Human iPSCs Into Mesenchymal Lineages by Optogenetic Control of TGF-β Signaling", Cell Reports, May 20, 2023, vol. 42, No. 5, 24 pages.

Zhao, E.M. et al., "Optogenetic Regulation of Engineered Cellular Metabolism for Microbial Chemical Production", Nature, Mar. 29, 2018, vol. 555, No. 7698, 34 pages.

Nagel et al., "Channelrhodopsin-1: A Light-Gated Proton Channel in Green Algae", Science, (Jun. 28, 2002), vol. 296, pp. 2395-2398.

Deisseroth et al., "Next-Generation Optical Technologies for Illuminating Genetically Targeted Brain Circuits", J. Neurosci., (Oct. 11, 2006), vol. 26, No. 41, pp. 10380-10386.

Fenno et al., "The Development and Application of Optogenetics", Annu. Rev. Neurosci., (2011), vol. 34, pp. 389-412.

Yazawa et al., "Induction of protein-protein interactions in live cells using light", Nat. Biotechnol., (Oct. 2009), vol. 27, No. 10, pp. 941-945.

Wu, et al., "A genetically encoded photoactivatable Rac controls the motility of living cells", Nature, (Sep. 3, 2009), vol. 461, pp. 104-108.

Levskaya et al., "Spatiotemporal control of cell signalling using a light-switchable protein interaction", Nature, (2009), vol. 461, pp. 997-1001.

Shimizu-Sato et al., "A light-switchable gene promoter system", Nat. Biotechnol., (Oct. 2002), vol. 20, pp. 1041-1044.

Kennedy et al., "Rapid blue-light-mediated induction of protein interactions in living cells", Nat. Methods, (Dec. 2010), vol. 7, No. 12, pp. 973-975.

Zhang et al., "Optogenetic control of intracellular signaling pathways", Trends Biotechnol., (Feb. 2015), vol. 33, No. 2, pp. 92-100.

Tischer et al. "Illuminating cell signalling with optogenetic tools", Nat. Rev. Mol. Cell Biol., (Aug. 2014), vol. 5, pp. 551-558.

Bugaj et al., Optogenetic protein clustering and signaling activation in mammalian cells, Nat. Methods, (Mar. 2013), vol. 10, No. 3, pp. 249-252.

Furue et al., "Heparin promotes the growth of human embryonic stem cells in a defined serum-free medium", Proc. Natl. Acad. Sci. U.S.A., (2008), vol. 105, No. 46, pp. 13409-13414.

Tesar et al., "New cell lines from mouse epiblast share defining features with human embryonic stem cells", Nature, (Jul. 12, 2007), vol. 448, pp. 196-199.

Takahashi et al., "Induction of Pluripotent Stem Cells from Adult Human Fibroblasts by Defined Factors", Cell, (Nov. 30, 2007), vol. 131, pp. 861-872.

(56) References Cited

OTHER PUBLICATIONS

Levenstein et al., "Basic Fibroblast Growth Factor Support of Human Embryonic Stem Cell Self-Renewal", Stem Cell., (2006), vol. 24, No. 3, pp. 568-574.
Thomson et al., "Embryonic Stem Cell Lines Derived from Human Blastocysts", Science, (Nov. 6, 1998), vol. 282, pp. 1145-1147.
West et al., "Porcine Induced Pluripotent Stem Cells Produce Chimeric Offspring", Stem Cells Dev., (2010), vol. 19, No. 8, pp. 1211-1220.
Ezashi et al., "Derivation of induced pluripotent stem cells from pig somatic cells", Proc. Natl. Acad. Sci. U.S.A., (Jul. 7, 2009), vol. 106, No. 27, pp. 10993-10998.
Amit et al., "Clonally Derived Human Embryonic Stem Cell Lines Maintain Pluripotency and Proliferative Potential for Prolonged Periods of Culture", Dev. Biol., (2000), vol. 227, pp. 271-278.
Itoh et al., "Evolution of the Fgf and Fgfr gene families", Trends Genet., (Nov. 2004), vol. 20, No. 11, pp. 563-569.
Beer et al., "Fibroblast Growth Factor (FGF) Receptor 1-IIIb is a Naturally Occurring Functional Receptor for FGFs That is Preferentially Expressed in the Skin and the Brain", J. Biol. Chem., (May 26, 2000), vol. 275, No. 21, pp. 16091-16097.
Urakawa et al., "Klotho converts canonical FGF receptor into a specific receptor for FGF23", Nature, (Dec. 7, 2006), vol. 444, pp. 770-774.
Ornitz et al., "Heparin is Required for Cell-Free Binding of Basic Fibroblast Growth Factor to a Soluble Receptor and for Mitogenesis in Whole Cells", Mol. Cell Biol., (Jan. 1992), vol. 12, pp. 240-247.
Mohammadi et al., "Identification of Six Novel Autophosphorylation Sites on Fibroblast Growth Factor Receptor 1 and Elucidation of Their Importance in Receptor Activation and Signal Transduction", Mol. Cell Biol., (Mar. 1996), vol. 16, No. 3, pp. 977-989.
Chen et al., "Thermal Stability of Fibroblast Growth Factor Protein is a Determinant Factor in Regulating Self-Renewal, Differentiation, and Reprogramming in Human Pluripotent Stem Cells", Stem Cell., (2012), vol. 30, pp. 623-630.
Choi et al., "Concordant but Phenotypes among Duchenne Muscular Dystrophy Patient-Specific Myoblasts Derived using a Human iPSC-Based Model", Cell Rep., (Jun. 7, 2016), vol. 15, pp. 2301-2312.
Mali et al., "RNA-Guided Human Genome Engineering via Cas9", Science, (Feb. 15, 2013), vol. 339, pp. 823-826.
Choi et al., "Transcriptional landscape of myogenesis from human pluripotent stem cells reveals a key role of TWIST1 in maintenance of skeletal muscle progenitors", Elife, (2020) 9, (27 pages).
Lim et al., "Profiling Individual Human Embryonic Stem Cells by Quantitative RT-PCR", J. Vis. Exp., (May 29, 2014), Issue 87, (6 pages).
Kriks et al., "Dopamine neurons derived from human ES cells efficiently engraft in animal models of Parkinson's disease", Nature, (Dec. 29, 2011), vol. 480, pp. 547-551.
Grusch et al., "Spatio-temporally precise activation of engineered receptor tyrosine kinases by light", EMBO J., (2014), vol. 33, No. 15, pp. 1713-1726.
Huang et al., "Isolation and characterization of a Chlamydomonas gene that encodes a putative blue-light photoreceptor of the phototropin family", Physiol. Plant, (2002), vol. 115, pp. 613-622.
Kinoshita et al., "phot1 and phot2 mediate blue light regulation of stomatal opening", Nature, (Dec. 6, 2001), vol. 414, pp. 656-660.
Takahashi et al., "Aureochome, a photoreceptor required for photomorphogenesis in stramenopiles", Proc. Natl. Acad. Sci. U.S. A., (Dec. 4, 2007), vol. 104, No. 49, p. 19625-19630.
Toyooka et al., "Photoreactions of Aureochrome-1", Biophys. J., (Jun. 2011), vol. 100, pp. 2801-2809.
Oh et al., "Functional Coupling with Cardiac Muscle Promotes Maturation of hPSC-Derived Sympathetic Neurons", Cell Stem Cell, (Jul. 7, 2016), vol. 19, pp. 95-106.
Cong et al., "Multiplex Genome Engineering Using CRISPR/Cas systems", Science, (Feb. 15, 2013), vol. 339, pp. 819-823.
Lotz et al., "Sustained Levels of FGF2 Maintain Undifferentiated Stem Cell Cultures with Biweekly Feeding", PloS One, (Feb. 2013), vol. 8, Issue. 2, (10 pages).
Xie et al., "Optimization of a CRISPR/Cas9-mediated Knock-in Strategy at the Porcine Rosa26 Locus in Porcine Foetal Fibroblasts", Sci. Rep., (2017), vol. 7, (12 pages).
Kim et al., "Spatiotemporal Control of Fibroblast Growth Factor Receptor Signals by Blue Light", Chem Biol., (Jul. 17, 2014), vol. 21, pp. 903-912.
Ll et al., "Spatiotemporal Control of TGF-beta Signaling with Light", ACS Synth. Biol., (2018), vol. 7, pp. 443-451.
Johnson et al., "The Spatiotemporal Limits of Developmental Erk Signaling", Dev. Cell, (2017), vol. 40, pp. 185-192.
Sako et al., "Optogenetic Control of Nodal Signaling Reveals a Temporal Pattern of Nodal Signaling Regulating Cell Fate Specification During Gastrulation", Cell Rep., (2016), vol. 16, pp. 866-877.
Zhang et al. "Heat shock protein 27 promotes cell proliferation through activator protein-1 in lung cancer", Oncol. Lett., (2015), vol. 9, pp. 2572-2576.
Reyes et al., "Activation of mitogen- and stress-activated kinase 1 is required for proliferation of breast cancer cells in response to estrogens or progestins", Oncogene, (2014), vol. 33, pp. 1570-1580.
Gentile et al., "VEGF-mediated phosphorylation of eNOS regulates angioblast and embryonic endothelial cell proliferation", Dev. Biol., (2013), vol. 373, pp. 163-175.
Liu et al., "Photoexcited CRY2 Interacts with CIB1 to Regulate Transcription and Floral Initiation in *Arabidopsis*", Science, (Dec. 5, 2008), vol. 322, pp. 1535-1539.
Gao et al., "Establishment of porcine and human expanded potential stem cells", Nat. Cell Biol., (Jun. 2019), vol. 21, pp. 687-699.
Chen et al., "Chemically defined conditions for human iPSC derivation and culture", Nat. Methods, (May 2011), vol. 8, No. 5, pp. 424-429.
Stockley et al., "Surpassing light-induced cell damage in vitro with novel cell culture media", Sci. Rep., (Apr. 12, 2017), vol. 7, (11 pages).
Porrello et al., "A symphony of stem cells in Vienna—looking to the future, 2018", The Company of Biologists, (2018), vol. 145, (6 pages).
Cui et al., Exosomes from adipose-derived mesenchymal stem cells protect the myocardium against ischemia/reperfusion injury through Wnt/β-catenin signaling pathway. J Cardiovasc Pharmacol 70(4):225-231 (2017).
Hellwarth, Peter et al. Optogenetic-mediated cardiovascular differentiation and patterning of human pluripotent stem cells. Advanced genetics (Hoboken) 2(3):1-9 (2021).
Humphreys, Paul et al. Optogenetic Control of the BMP Signaling Pathway. ACS Synthetic Biology 9(11):3067-3078 (2020).
Kainrath, Stephanie et al. Green-Light-Induced Inactivation of Receptor Signaling Using Cobalamin-Binding Domains. Angewandte Chemie 56(16): 4608-4611 (2017).
Karlin, Samuel et al. Applications and Statistics for Multiple High-scoring Segments in Molecular Sequences. PNAS USA 90(12):5873-5877 (1993).
Kim, et al., Spatiotemporal control of fibroblast growth factor receptor signals by blue light. Chemistry & Biology 21(7):806-808 (2014).
Krishnamurthy, Vishnu et al. A Generalizable Optogenetic Strategy to Regulate Receptor Tyrosine Kinases during Vertebrate Embryonic Development. Journal of Molecular Biology (10):3149-3158 (2020).
Leopold, Anna et al. Bacterial Phytochrome as a Scaffold for Engineering of Receptor Tyrosine Kinases Controlled with Near-Infrared Light. Journal of Molecular Biology 432(13):3749-3760 (2020).
Mildmay-White et al., Cell surface markers on adipose-derived stem cells: a systematic review. Curr Stem Cell Res Ther. 12(6):484-492 (2017).
UniProtKB Accession No. A0A3Q1LUE0. Fibroblast growth factor receptor (FGFR1). Record created Apr. 10, 2019. 9 pages. Retrieved Mar. 22, 2024 at URL: https://www.uniprot.org/uniprotkb/A0A3Q1LUE0/entry.

(56) References Cited

OTHER PUBLICATIONS

UniProtKB Accession No. A8QW55. Aureochrome1 (AUREO1). Record created Jan. 15, 2008. 5 pages. Retrieved Mar. 22, 2024 at URL: https://www.uniprot.org/uniprotkb/A8QW55/entry.
Vieira et al., Isolation-characterization-and-differentiation-potential-of-canine-adipose-derived-stem-cells. Cell Transplantation 19(3):279-289 (2010).

* cited by examiner

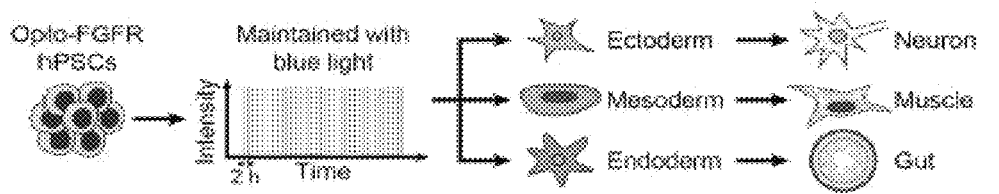
FIG. 3A
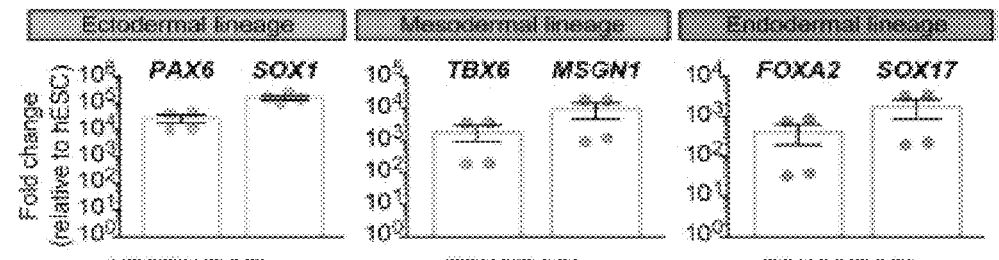
FIG. 3B
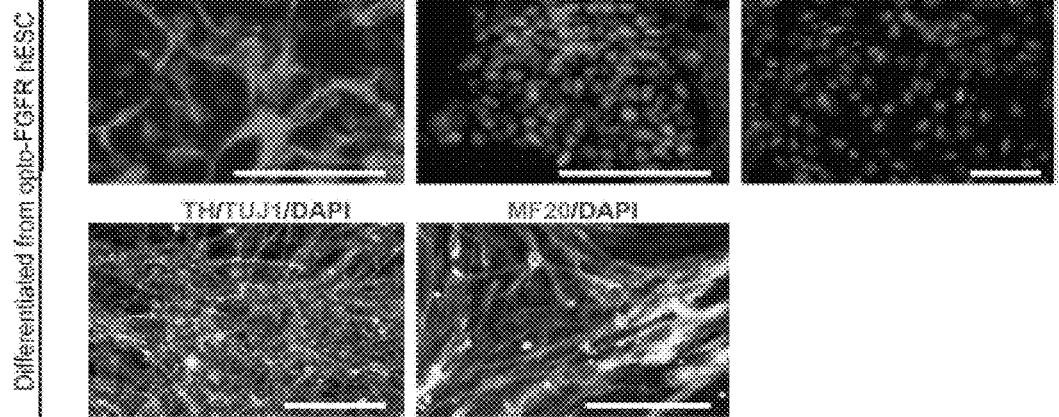
FIG. 3C
FIG. 3D
FIG. 3E
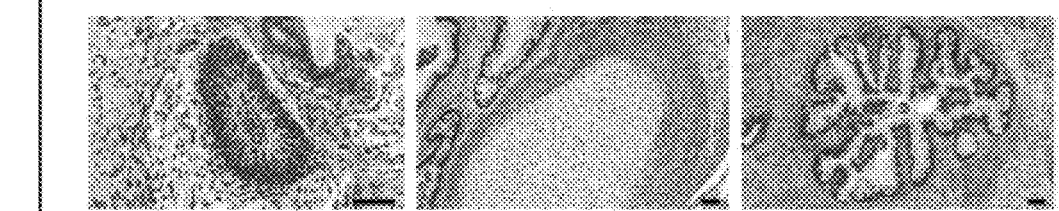
FIG. 3F
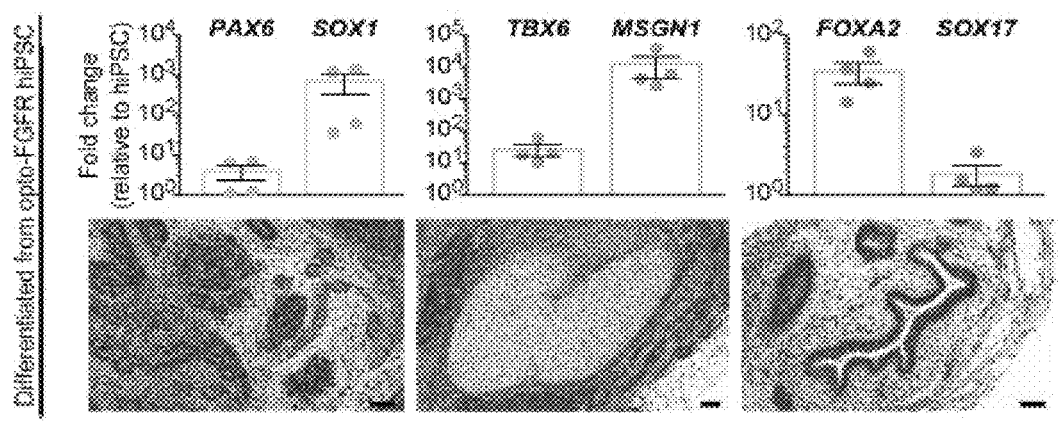
FIG. 3G

| gRNA | No. of transfected cells | No. of colonies after selection |
|---|---|---|
| #1 | 8 million | 6 |
| #91 | 4 million | 7 |
FIG. 13A
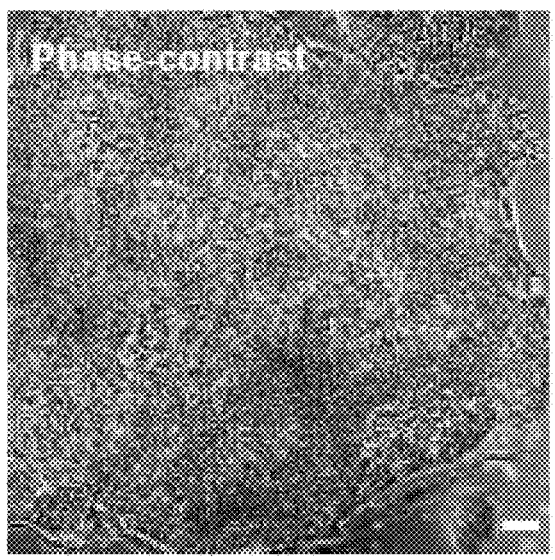
FIG. 13B
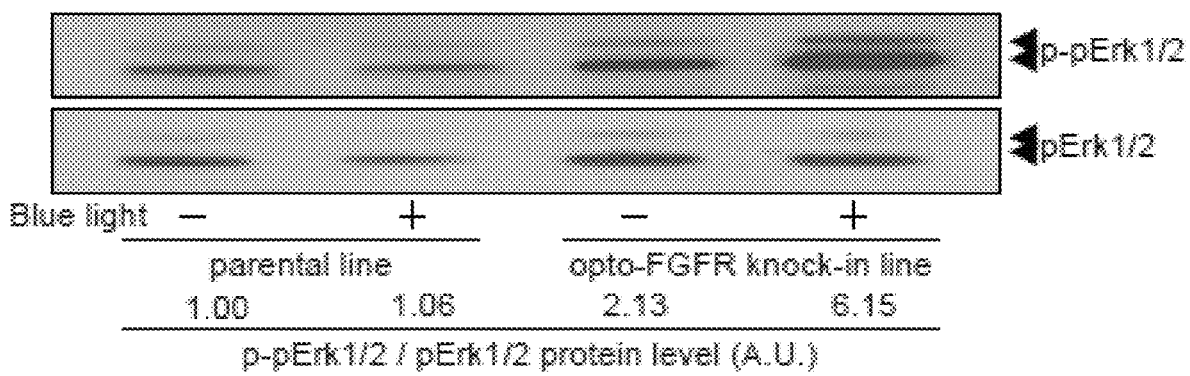
FIG. 13C

OPTICALLY CONTROLLABLE FGFR STIMULATION USING WIRELESS CONTROLLED CELLULAR LIGHTING SYSTEM

CROSS-REFERENCE TO RELATED APPLICATIONS

This application claims the benefit of U.S. Provisional Application No. 62/962,246, filed Jan. 17, 2020, which is incorporated herein by reference in its entirety.

GOVERNMENT SUPPORT CLAUSE

This invention was made with government support under grant nos. NS093213 and AR070751 awarded by the National Institutes of Health, and grant no. 1547515 awarded by the National Science Foundation. The government has certain rights in the invention.

FIELD OF THE INVENTION

The present invention relates to the field of stem cells. More specifically, the present invention provides compositions and methods for using optogenetics to sustain the pluripotency of stem cells.

INCORPORATION-BY-REFERENCE OF MATERIAL SUBMITTED ELECTRONICALLY

This application contains a sequence listing. It has been submitted electronically via EFS-Web as an ASCII text file entitled "P15986-02_ST25.txt." The sequence listing is 26,756 bytes in size, and was created on Jan. 19, 2021. It is hereby incorporated by reference in its entirety.

BACKGROUND OF THE INVENTION

Identification of channel rhodopsins as light-gated ion channels in algal system [1], followed by various sensory photoreceptors, has opened a new chapter of optogenetics [2] in biological processes. Optogenetics utilized key properties of sensory photoreceptors by sophisticated modulation of molecular targets with high spatial and temporal control, which certainly overcomes many drawbacks of conventional approaches. Current application of optogenetics is mostly limited to neuroscience field relying on ion channels and light-driven ion pumps [3], but there should be plenty of other applications in many biology and medicine.

Previous pioneering studies have discovered several photoactivatable proteins, such as LOV (light-oxygen-voltage-sensing) domain [4,5], phytochrome B (PhyB) [6,7], and cryptochrome 2 (Cry2) [8]. Such photoactivatable proteins are key players for the optogenetic control of intracellular signal transduction because, by absorbing energy from the photons in excitation light, they can undergo conformational changes, rearrange inter- or intra-protein contacts, and modulate inter-or intra-protein interactions [9]. Such changes in photoactivable proteins can mimic the dimerization of a signaling pathway, simply by light illumination at a certain wavelength. For example, a photosensitive protein Cry2 homo-oligomerizes, and LOV domain homo-dimerizes, both within seconds when illuminated with stimulatory light (~470 nm) [9,10]. Therefore, photoactivatable proteins are enticing light-sensing modules for use in optogenetic studies of intracellular signaling in mammalian systems [11] because they have rapid responsiveness with high temporal (sub-second time resolution) and spatial (sub-cellular spatial resolution) precision, and they do not need exogenous cofactors or signaling peptides.

Fibroblast growth factor 2 (FGF2) is a key component that promotes self-renewal and inhibits spontaneous differentiation of mammalian pluripotent stem cells (PSCs), including human PSC (hPSC) and porcine induced PSC (piPSC) [12-19]. The human FGF family consists of 22 members (FGF1 to 23, except FGF15), which are structurally related signaling molecules and subdivided into 7 subfamilies [20]. The mammalian FGF receptor (FGFR) family, however, has only 4 highly conserved receptor tyrosine kinases (FGFR1 to 4) [7]. Among them, FGFR1 predominantly interacts with FGF1 and FGF2 [21-23]. Like other receptor tyrosine kinases, FGFR1 dimerizes and trans-autophosphorylates a large number of tyrosine residues upon binding with FGF2, consequently activating downstream signaling pathways [24].

PSCs can be proliferated indefinitely and have the potential to differentiate into many different cell types with promising applications. The establishment of a high-quality, high-precision culture system is necessary for PSC applications; the existing culture protocols are completely dependent on recombinant proteins that are critical culture medium components for the maintenance of PSCs [12-16, 19]. However, high cost, thermal instability [25], and random distribution of the recombinant proteins impede large-scale manufacturing. Here, we have developed a novel culture system for PSCs using optical induction of the FGF signaling pathway. Our system maintained pluripotency of PSCs similar to the conventional culture system. Furthermore, the optically maintained PSCs displayed the ability to differentiate into three germ layers, demonstrating that the optical culture system can sustain the pluripotency of PSCs without exogenous FGF2 protein supplementation.

SUMMARY OF THE INVENTION

The present invention provides one or more fusion protein embodiments having a cytoplasmic region of the FGF receptor-1 and a light-oxygen-voltage domain, which creates a tunable, blue light-dependent activation of FGF signaling in human and porcine pluripotent stem cells (PSCs). The present invention also provides a novel PSC culture system which can include a wired or wirelessly controllable optical activation of the fibroblast growth factor (FGF) signaling pathway in the cells in culture without the need for daily supplementation of recombinant FGF2 protein, a key molecule for maintaining pluripotency of PSCs. The present invention provides a highly controllable optical stimulation of the FGF signaling pathway sufficient for long-term maintenance of PSCs, without the loss of differentiation potential into three germ layers. These embodiments allow for culture systems that are a cost-effective platform for human clinical trials and animal cellular agriculture Therefore, in accordance with an embodiment, the present invention provides a synthetic polynucleotide comprising a sequence encoding the intracellular domain of the fibroblast growth factor 1 receptor (FGFR1) fused to a sequence encoding a photoactivatable light-oxygen-voltage sensing (LOV) domain.

In accordance with another embodiment, the present invention provides a synthetic polynucleotide comprising a sequence encoding the intracellular domain of the fibroblast growth factor 1 receptor (FGFR1) fused to a sequence encoding a photoactivatable light-oxygen-voltage sensing (LOV) domain comprising the nucleotide sequence of SEQ ID NO:6.

In accordance with an embodiment, the present invention provides a synthetic polynucleotide comprising a sequence encoding the intracellular domain of the fibroblast growth factor 1 receptor (FGFR1) fused to a sequence encoding a photoactivatable light-oxygen-voltage sensing (LOV) domain, a promoter sequence and a sequence encoding a myristolation signal peptide (Myr).

In accordance with an embodiment, the present invention provides an expression vector comprising synthetic polynucleotide comprising a sequence encoding the intracellular domain of the fibroblast growth factor 1 receptor (FGFRT) fused to a sequence encoding a photoactivatable light-oxygen-voltage sensing (LOV) domain.

In accordance with an embodiment, the present invention provides an expression vector comprising synthetic polynucleotide comprising a sequence encoding the intracellular domain of the fibroblast growth factor 1 receptor (FGFRT) fused to a sequence encoding a photoactivatable light-oxygen-voltage sensing (LOV) domain.

In accordance with another embodiment, the present invention provides a an expression vector comprising synthetic polynucleotide comprising a sequence encoding the intracellular domain of the fibroblast growth factor 1 receptor (FGFR1) fused to a sequence encoding a photoactivatable light-oxygen-voltage sensing (LOV) domain, a promoter sequence and a sequence encoding a myristolation signal peptide (Myr).

In accordance with another embodiment, the present invention provides a an expression vector comprising synthetic polynucleotide comprising a sequence encoding the intracellular domain of the fibroblast growth factor 1 receptor (FGFR1) fused to a sequence encoding a photoactivatable light-oxygen-voltage sensing (LOV) domain, a promoter sequence and a sequence encoding a myristolation signal peptide (Myr) comprising the nucleotide sequence of SEQ ID NO:1.

In accordance with an embodiment, the present invention provides expression vectors comprising the synthetic polynucleotides described herein.

In accordance with an embodiment, the present invention provides a transformant transformed by the vectors described herein, including, for example, mammalian cells, and specifically, pluripotent stem cells.

In accordance with an embodiment, the present invention provides a fibroblast growth factor free pluripotent stem cell culture system comprising one or more transformed cells as described herein and an illumination source.

In accordance with an embodiment, the present invention provides a method for maintaining a pluripotent stem cell line in culture comprising: a) a plurality of pluripotent stem cells in a fibroblast growth factor free culture medium, wherein said are transformed with the expression vectors described herein; b) said transformed cells are maintained in the cell culture system as described herein; and c) periodically illuminating the cells of b) at a wavelength of about 470 nm for a sufficient time and intensity such that the cells maintain their pluripotent capability.

Accordingly, in one aspect, the present invention provides a vector. In one embodiment, a vector comprises a nucleotide sequencing encoding a fusion protein comprising the intracellular domain of fibroblast growth factor 1 receptor (FGFR1) and a photoactivatable domain. In another embodiment, the fusion protein further comprises a signal peptide. In a specific embodiment, the signal peptide comprises a myristolation signal peptide (Myr). In a more specific embodiment, the Myr comprises the amino acid sequence of SEQ ID NO:4.

In another specific embodiment, the intracellular domain of FGFR1 comprises the amino acid sequence of SEQ ID NO:6. In particular embodiments, the photoactivatable domain comprises a light-oxygen-voltage sensing (LOV) domain. In a specific embodiment, the LOV domain comprises the amino acid sequence of SEQ ID NO:8. In yet another embodiment, the vector comprises the nucleotide sequence of SEQ ID NO:1. In certain embodiments, the present invention provides a pluripotent stem cell (PSC) comprising a vector described herein.

In another aspect, the present invention provides a modified pluripotent stem cell. In one embodiment, the present invention provides a PSC whose genome comprises a nucleotide sequence encoding a fusion protein comprising the intracellular domain of FGFR1 and a photoactivatable domain. In another embodiment, the present invention provides a PSC that expresses a fusion protein comprising the intracellular domain of fibroblast growth factor 1 receptor (FGFRT) and a photoactivatable domain.

In another embodiment, the fusion protein further comprises a signal peptide. In a specific embodiment, the signal peptide comprises a myristolation signal peptide (Myr). In a more specific embodiment, the Myr comprises the amino acid sequence of SEQ ID NO:4. In another specific embodiment, the intracellular domain of FGFR1 comprises the amino acid sequence of SEQ ID NO:6. In particular embodiments, the photoactivatable domain comprises a light-oxygen-voltage sensing (LOV) domain. In a specific embodiment, the LOV domain comprises the amino acid sequence of SEQ ID NO:8.

In a further aspect, the present invention provides a fibroblast growth factor 2 (FGF2) free PSC culture system. In one embodiment, the culture system comprises a PSC described herein and a cell culture illumination source capable of illuminating the PSC with a selected wavelength and intensity of light. In specific embodiments, the cell culture illumination source comprises a cell culture substrate, an upper and lower enclosure, one or more illumination sources, one or more circuit boards, and a microcontroller.

In particular embodiments, the illumination source can vary the wavelength of the illumination. In a specific embodiment, the illumination source emits light at a wavelength of about 470 nm. In other embodiments, the illumination source comprises one or more light emitting diodes (LEDs). In a specific embodiment, the illumination source continuously illuminates the cells for a period of time between about 1 minute and about 120 minutes. In another specific embodiment, the illumination source illuminates the cells in a time interval of between about 30 minutes to about 4 hours. In certain embodiments, the illumination source illuminates the cells at an intensity of between about 0.1 µW/mm2 to about 25 µW/mm2. In particular embodiments, the microcontroller is controlled through a computer server via either a wireless or wired computer client.

In a further aspect, the present invention provides methods for maintaining the pluripotency of PSCs without exogenous FGF2 supplementation. In a specific embodiment, the method comprises the step of illuminating a PSC described herein with a light having a wavelength of about 470 nm.

BRIEF DESCRIPTION OF THE FIGURES

FIG. 1A, 1B: A schematic illustration of the FGF signaling pathway by (FIG. 1A) FGF ligand-elicited activation or by (FIG. 1B) an opto-FGFR activation via blue light illumination. FIG. 1C: A schematic illustration of the AAVS1 locus targeting using homologous recombination enhanced by the CRISPR/Cas9 system. P1-P4 indicate the PCR primer locations. Myr, myristoylation signal peptide; cytoFGFRT, the cytoplasmic region of FGFRT. FIG. 1D: A schematic illustration of Opto-FGFR PSC maintenance (+F, 10 ng/mL FGF2 protein treatment, daily; +L, 1 µW/mm$^2$ at 470 nm for 5 min. every 2 h). FIG. 1E: Representative colony morphologies of Opto-FGFR hESCs maintained in either +L condition for 54 weeks (left) or dark for 2 weeks (right). FIG. 1F, 1G: qRT-PCR results of Opto-FGFR hPSCs cultured for 3 weeks (FIG. 1F, hESCs) or 12 weeks (FIG. 1G, iPSCs) in either +F or +L condition (n=4; ns, not significant; unpaired t-test). All error bars represent mean±s.e.m. FIG. 1H: Representative images of Opto-FGFR hiPSCs maintained in +L condition for 12 weeks showed undifferentiated colony morphology (left) and expression of pluripotency markers TRA-1-81 (middle) and NANOG (right). Scale bars, 100 µm.

FIG. 2A: A schematic illustration of Opto-FGFR hESCs maintenance (+F, 10 ng/mL FGF2 protein treatment supplied daily; +L, 1 µW/mm$^2$ at 470 nm for 1-10 min. every 2 h; Diff. Ctrl, hESC-derived myotubes). FIG. 2B, 2C: Heat maps showing expression levels, (FIG. 2B) in log 2(FPKM) or (FIG. 2C) in FPKM, of specific genes in Opto-FGFR hESCs cultured in either +F, +L, or Diff Ctrl condition for 3 weeks. FPKM, fragments per kilobase of transcript per million mapped reads. FIG. 2D: A weighted Venn diagram between +F and +L groups, showing overlap of significantly differentially expressed genes compared to the Diff Ctrl group. FIG. 2E, 2F: Gene ontology (GO) analyses of (FIG. 2E) significantly upregulated genes and (FIG. 2F) downregulated genes in the +L group compared to the Diff Ctrl group.

FIG. 3A-3G. In vitro and in vivo differentiation abilities of Opto-FGFR hPSCs maintained with blue light illumination into three germ layers. FIG. 3A: A schematic illustration of the differentiation of optically maintained Opto-FGFR hPSCs (1 µW/mm$^2$ at 470 nm for 5 min. every 2 h) into three germ layers. FIG. 3B-3G: Germ layer differentiation of Opto-FGFR (FIG. 3B-3E, hESCs; f, g, hiPSCs) in which cells were cultured with blue light illumination. FIG. 3B, 3F: qRT-PCR results of the Opto-FGFR hPSCs, which were cultured with blue light illumination for 6 weeks and then differentiated into three germ layers (n=4). All error bars represent mean±s.e.m. FIG. 3C: Representative images of the Opto-FGFR hESCs, which were optically maintained for 10 weeks and then differentiated into three germ layers and immunostained with the indicated antibodies. FIG. 3D: Representative images of the Opto-FGFR hESCs, which were cultured with blue light illumination for 13 weeks, differentiated into dopaminergic neurons (left) and skeletal muscles (right), and immunostained with the indicated antibodies. FIG. 3E, 3G: Representative images of Opto-FGFR hPSC-derived tissues of three germ layers in in vivo teratoma assay. Scale bars, 100 µm.

FIG. 4A; A schematic illustration of the pRosa26 locus targeting using homologous recombination enhanced by the CRISPR/Cas9 system. cytoFGFR1, the cytoplasmic region of the FGFR1. FIG. 4B: A schematic illustration of Opto-FGFR piPSCs maintenance (+F, 10 ng/mL FGF2 protein treatment, daily; +L, 1 µW/mm$^2$ at 470 nm for 5 min. every 2 h). FIG. 4C: Representative colony morphologies of Opto-FGFR piPSCs maintained in either +L condition (left) or dark (right) for 3 weeks. FIG. 4D: A representative image of the Opto-FGFR piPSCs immunostained with OCT4 antibody after 3 weeks maintenance in +L condition. FIG. 4E: qRT-PCR results of Opto-FGFR piPSCs cultured in either +F or +L condition for 1 week (n=4; **, p value<0.01; *, p value<0.05; n.s., not significant; unpaired t-test). FIG. 4F: A schematic illustration of the differentiation of optically maintained Opto-FGFR piPSCs in +L condition into three germ layers. FIG. 4G: qRT-PCR results of the Opto-FGFR piPSCs, which were maintained in +L condition for 3 weeks and then differentiated into three germ layers (n=6). All error bars represent mean±s.e.m. Scale bars, 100 µm.

FIG. 5A: A blown-out diagram of the LED illuminating device, consisting of the base casing, the microcontroller board (Arduino Uno), the LED circuit boards, and the top casing, with a standard 6-well tissue culture plate. FIG. 5B: Wire diagram between Arduino Uno and LED circuit boards. FIG. 5C: A fully-assembled LED illuminating device for 6-well plates. FIG. 5D: Schematic overview of the wireless optogenetic system. FIG. 5E: The server computer's user interface (UI) where users can control the phases of illumination and LED intensity and view current status of LED illumination. FIG. 5F: The mobile client's UI where users can wirelessly control phases of illumination and LED intensity and view current status of LED illumination.

FIG. 6A: Validation of opto-FGFR gene cassette knock-in in hPSCs. Genomic DNA from the parental hESCs, Opto-FGFR hESCs, and Opto-FGFR hiPSCs was amplified using the indicated primer pairs (Endogenous, P1 and P2; Left Arm, P1 and P3; Right Arm, P4 and P2; primer pair locations are shown in FIG. 1c). FIG. 6B, 6C: Representative colony morphologies and NANOG expression of opto-FGFR knock-in (FIG. 6B) hESCs and (FIG. 6C) hiPSCs. FIG. 6D: PSC culture plates for FGF ligand treatment (left) and blue light illumination (right). FIG. 6E, 6F: The phosphorylation kinetics of (FIG. 6E) ERK1/2 and (FIG. 6F) MEK in the Opto-FGFR hESCs treated with FGF2 protein (red circles, n=4) or blue light (blue squares, n=4). All error bars represent mean±s.e.m. Scale bars, 100 µm.

FIG. 7A, 7B: The effect of duration (a, 1 µW/mm$^2$ at 470 nm for 0-10 min) and intensity (b, 0-1 µW/mm$^2$ at 470 nm for 5 min) of illumination on ERK1/2 phosphorylation (n=4; **, p value<0.01; *, p value<0.05; n.s., not significant; unpaired t-test). All error bars represent mean±s.e.m.

FIG. 8A: The heatmap shows comparable levels of phosphorylation in multiple protein substrates in the FGF signaling pathway activated by FGF2 protein treatment (FGF, 10 ng/mL for 30 min; n=4) and blue light illumination (Opto, 1 µW/mm$^2$ at 470 nm for 30 min; n=4). FIG. 8B: The relative value of phosphorylation in the blue light illumination and FGF2 protein treated groups. FIG. 8C: The ratio of phosphorylated versus non-phosphorylated proteins in the blue light illumination and FGF2 protein treated groups. All error bars represent mean±s.e.m.

FIG. 9A: A schematic illustration of Opto-FGFR hESCs maintenance (+F, 10 ng/mL FGF2 protein treatment supplied daily; +L, 1

µW/mm² at 470 nm for 5 min. every 2 h; Untreated, maintained without FGF2 protein or blue light). FIG. 9B: Quantification of FACS analyses of SSEA4⁺ cells from Opto-FGFR hESCs maintained in +F, +L, and Untreated conditions for 1 week (passage 1) or 3 weeks (passage 3) (n=3; ***, p value<0.001; ns, not significant; unpaired t-test). The colored lines indicate each mean value. FIG. 9C: Representative FACS plots of OCT4::EGFP+ cells from Opto-FGFR hESCs cultured in either +F or +L condition for 3 weeks. FIG. 9D, 9E: Representative images of the Opto-FGFR hESCs immunostained with the indicated antibodies after (FIG. 9D) 6 weeks or (FIG. 9E) 54 weeks maintenance in +L condition. FIG. 9F: A karyotype of Opto-FGFR hESCs cultured with blue light for 4 weeks showed no aneuploidy and no structural rearrangements. Scale bars, 100 µm.

FIG. 10A: A schematic illustration of the freezing and thawing procedure of optically maintained hESCs (1 µW/mm² at 470 nm for 5 min. every 2 h). Opto-FGFR hESCs cultured with blue light illumination for 2 passages (2 weeks) were frozen into stock vials (stored in LN₂ tank for 2 weeks) then thawed and maintained for 3 weeks with blue light illumination. FIG. 10B: A representative morphology of the resulting Opto-FGFR hESC colony (left) and the expression of NANOG (right). Scale bars, 100 µm.

FIG. 11A: A schematic illustration of Opto-FGFR hESC maintenance (+F, 10 ng/mL FGF2 protein treatment supplied daily; +L, 1 µW/mm² at 470 nm for 5 min. every 2 h) and their single-cell qRT-PCR. OCT4::EGFP+ single-cells were captured by FACS sorting into a 96-well plate for qRTPCR. FIG. 11B: qRT-PCR results of Opto-FGFR hESCs cultured in either +F or +L condition for 45 weeks (n=78 for +F, n=88 for +L; n.s., not significant; unpaired t-test). For box and whisker plots, the black line across the box represents the median, the box represents interquartile range and the whiskers represent the minimum and maximum.

FIG. 12A: A schematic illustration of Opto-FGFR hESCs maintenance (+F, 10 ng/mL FGF2 protein treatment supplied daily; +L, 1 µW/mm² at 470 nm for 1 min. every 2 h). FIG. 12B: Scatter plot of global transcriptome changes between +F and +L conditions. The log 2 expression levels of genes from RNA-seq data are plotted. FPKM, fragments per kilobase of transcript per million mapped reads. FIG. 12C: Volcano plot of global transcriptome changes between +F and +L conditions. The log 2 (fold change) expression levels (+F vs +L) and $-\log_{10}$(p value) of genes from RNA-seq data are plotted.

FIG. 13A-13F. The generation of opto-FGFR knock-in piPSCs. FIG. 13A: The number of transfected cells and colonies formed after puromycin selection in each trial. FIG. 13B: Representative colony morphology of opto-FGFR knock-in piPSCs. FIG. 13C: Phosphorylation of pErk1/2 in Opto-FGFR piPSCs in response to blue light illumination (1 µW/mm² at 470 nm for 5 min). A.U., arbitrary unit. FIG. 13D: A schematic illustration of Opto-FGFR piPSCs maintenance (+L, 1 µW/mm² at 470 nm for 5 min. every 2 h). FIG. 13E: A representative image of alkaline phosphatase staining of undifferentiated piPSCs maintained with blue light illumination for 1 week. FIG. 13F: A karyotype of Opto-FGFR piPSC cultured with blue light for 3 weeks showed no aneuploidy and no structural rearrangements. Scale bars, 100 µm.

FIG. 14A-14C: Representative images of optically maintained Opto-FGFR hESCs (1 µW/mm² at 470 nm for 5 min. every 2 h) without feeder cells for 3 weeks showed (FIG. 14A) undifferentiated colony morphology and expression of pluripotency markers (FIG. 14B) OCT4 and (FIG. 14C) NANOG. FIG. 14D, 14E: Representative images of optically maintained Opto-FGFR hESCs (1 µW/mm² at 470 nm for 5 min. every 2 h) without feeder cells for 8 weeks showed (FIG. 14D) undifferentiated colony morphology and (FIG. 14E) no aneuploidy and no structural rearrangements in their karyotype. Scale bars, 100 µm.

FIG. 15A: Phosphorylation of ERK1/2 in response to blue light illumination (3.4-34 µW/mm² at 470 nm for 1 min. every 10 min. for 3 cycles) in human embryonic kidney cells (293T) transiently transfected with Cry2 PHR-based opto-FGFR. PD173074 (0.2 µM) was used as an FGF signaling inhibitor. FIG. 15B: A representative image of hESCs transiently transfected with Cry2 PHR-based opto-FGFR. FIG. 15C: Phosphorylation of ERK1/2 in response to blue light illumination (34 µW/mm² at 470 nm for 1 min. every 10 min. for 3 cycles) in hESCs transiently transfected with Cry2 PHR-based opto-FGFR. A.U., arbitrary unit. Scale bars, 100 µm.

DETAILED DESCRIPTION OF THE INVENTION

Figures 1A, 1B:
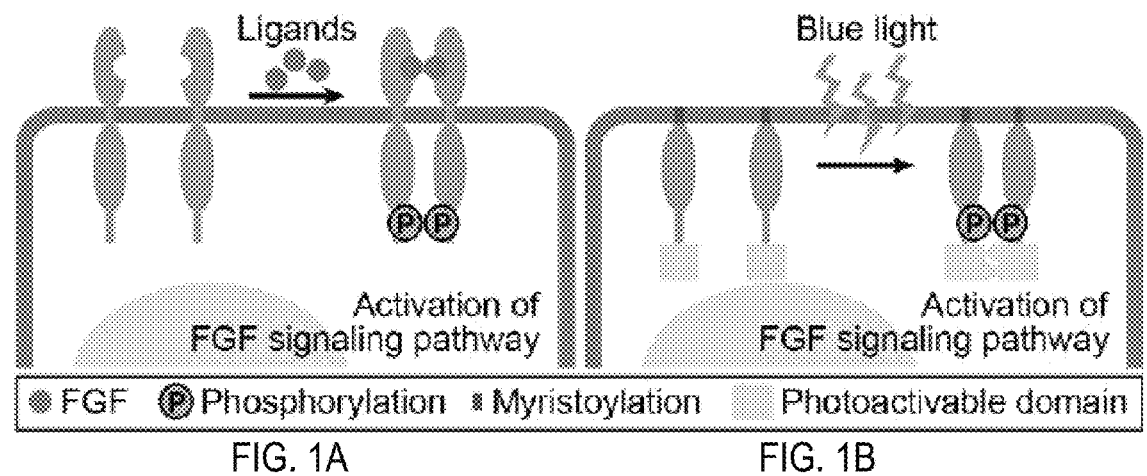
FIG. 1A-1H. Establishment of a novel and efficient FGF2-free hPSC culture system.

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

The present inventors have now developed a novel culture system for PSCs using optical induction of the FGF signaling pathway. The inventive fusion protein and illumination system maintained pluripotency of PSCs similar to the conventional culture system. Furthermore, the optically maintained PSCs displayed the ability to differentiate into three germ layers, demonstrating that the optical culture system can sustain the pluripotency of PSCs without exogenous FGF2 protein supplementation.

Previous reports have demonstrated the optical activation of receptor tyrosine kinases in immortalized cell lines and developing embryos as an initial step in evolving such optical technologies. Although a study using the optical control of ERK phosphorylation reported a perturbation of patterning and morphogenesis in *Drosophila* embryos, other studies did not report any biologically relevant phenotypes; therefore, translating these approaches for use with PSCs has remained challenging.

The present inventors have now extended the approach to human and porcine PSCs and provide clear evidence that the inventive opto-FGFR PSCs are sufficiently maintained by blue light illumination and without the need for FGF2 protein supplementation. Since there is no need to supplement FGF2 protein, the media does not need to be changed on a daily basis in the optical PSC culture system. In feeder-free culture systems, very high concentrations of FGF2 (up to 100 ng/mL) are required for promoting self-renewal and inhibiting spontaneous differentiation of hPSCs.

Even in a feeder-free culture system, the inventors succeeded in maintaining pluripotency of hESCs using the inventive illuminating culture system (FIG. 14). Moreover, the optically maintained PSCs appeared to retain the normal differentiation potential of traditional PSCs.

Figure 15A:
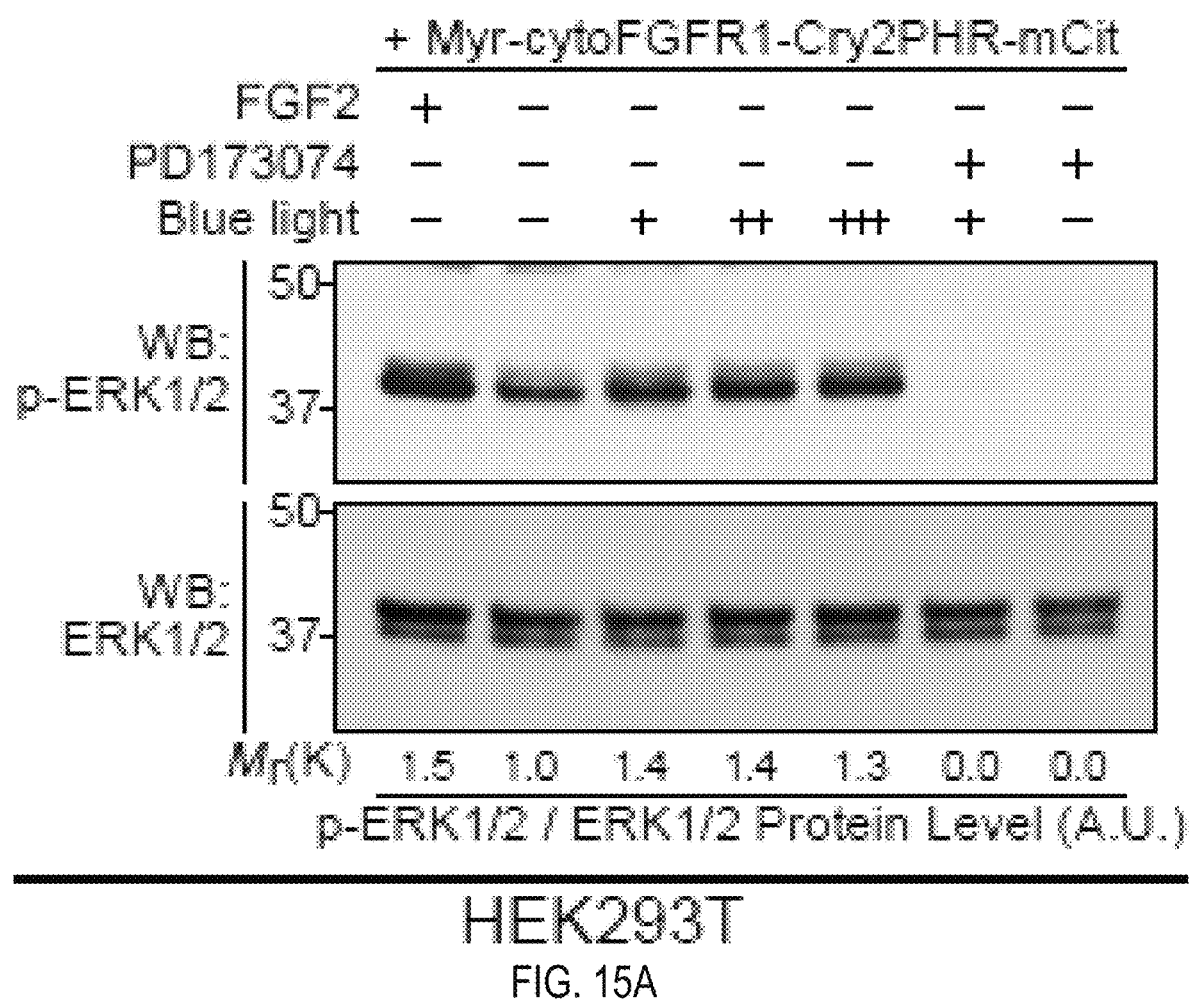
FIG. 15A-15C. Cry2 PHR-based opto-FGFR system.
Figure 15B:
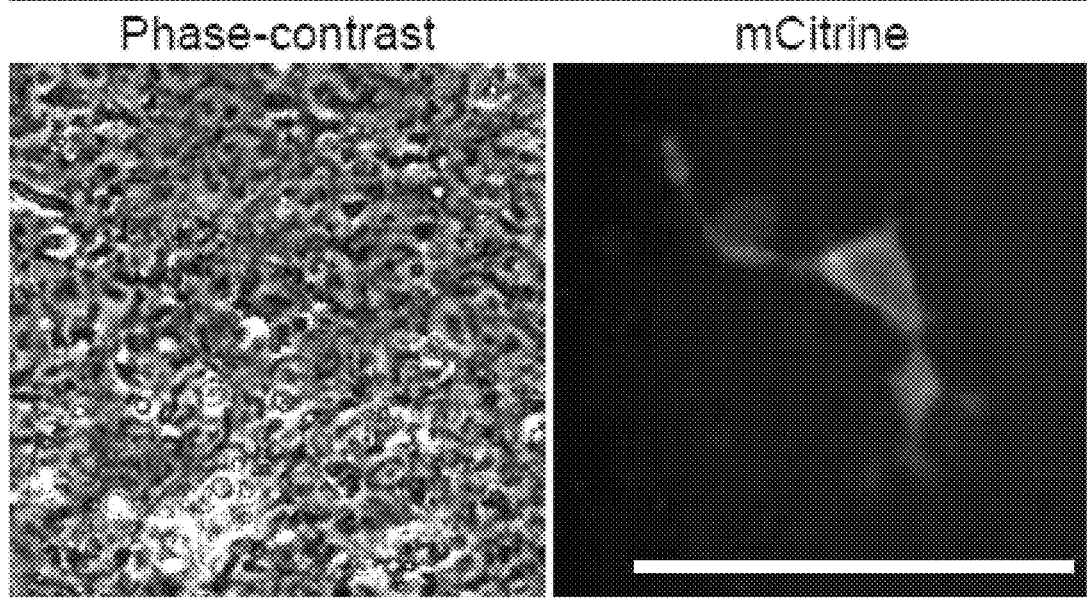
Figure 15C:
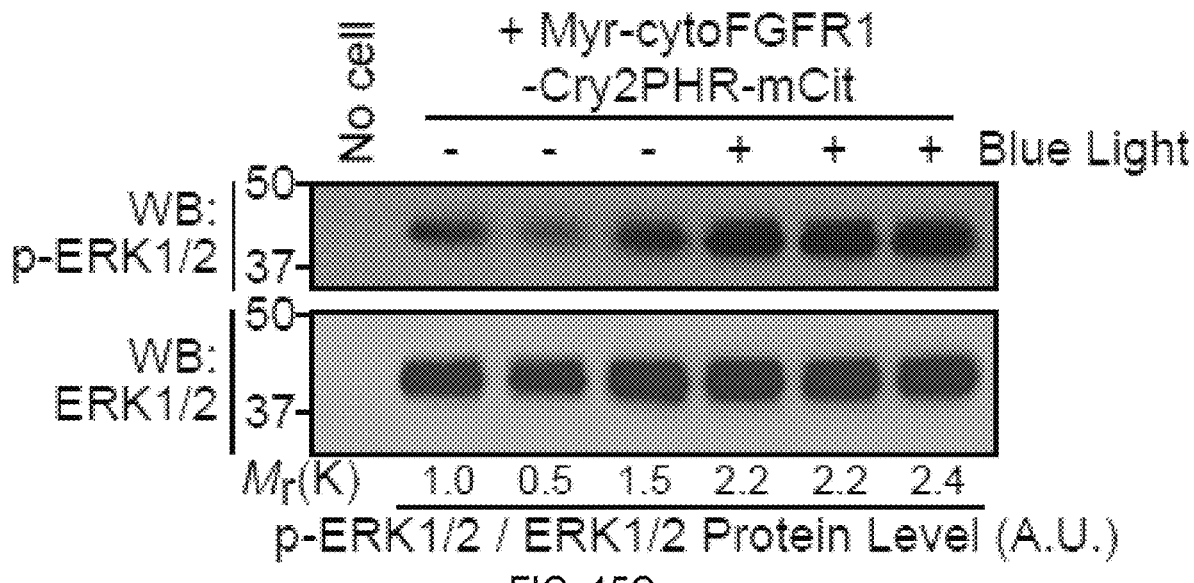

There are various kinds of photoactivatable proteins available for optogenetic approaches. Using the photolyase homology region of the Cry2 protein (Cry2PHR39) and LOV domain. In the present invention, the photosensory LOV domain served as an initiator in the light-induced intermolecular signal transduction cascade of the FGF signaling pathway (termed as opto-FGFR signaling) for maintaining the pluripotency of mammalian PSCs, without FGF2 protein supplementation. Although the inventors showed that they could optically activate FGF signaling in human embryonic kidney cells (HEK293T) and hESCs transiently transfected with the Cry2 PHR-based opto-FGFR (FIG. 15), the LOV domain was selected as a photodimerizable domain because of two reasons: the LOV domain has a shorter length (LOV, 432 bp or 144 aa26 vs Cry2 PHR, 1,506 bp or 502 aa35), which is more favorable for knock-in, and LOV domain has a shorter dissociation time after light withdrawal (LOV $t_{1/2}$=2.5 min vs Cry2 PHR $t_{1/2}$=5-6 min), which is more advantageous for accurate adjustment of the opto-FGFR signaling in PSC, than others. It is important to select an appropriate photosensory domain as the light-sensing actuator module for a given optogenetic modulation system in PSCs.

While it is a widely accepted idea that FGF2 protein directly stimulates PSCs for their self-renewal, there are other possible mechanisms of action of FGF2, such as direct and indirect interaction and association with the IGF pathway. However, until now, there has been no experimental tool to assess this possibility. The present invention herein provides the first direct evidence that the molecular mechanism underlying the daily supplementation with recombinant FGF2 protein to maintain the pluripotency of PSC is solely through the activation of the FGF signaling pathway.

The prior art stem cell culture systems are heavily dependent on random distribution of expensive and thermo-unstable recombinant proteins in a dish, which always can jeopardize future mass production of human stem cells for a population-wide cell therapy. The present inventive opto-FGFR PSCs enable optical activation without any exogenous FGF2 recombinant proteins and offer spatiotemporally precise optical control of stem cell behaviors. Beyond implementing a new technology in the stem cell field, the present experimental data will help lead to the development of a potential therapeutic cure against many human diseases by modulating multiple signaling pathways other than FGF2 and maximizing the potential of human PSCs.

The prior art animal agriculture and husbandry methods cause significant environmental issues such as greenhouse gas emissions, fresh water consumption, and arable land usage. As an alternative, cellular agriculture or 'lab-grown meats' have been introduced and social consent is growing due to ethical and environmentally friendly concepts. However, the production costs and use of animal-derived thermo-unstable recombinant proteins during the cellular agriculture process are barriers to entering the market for mass consumption. Based on the inventors' calculation, recombinant FGF2 protein for 1 billion of PSC culture costs ~$14,000 weekly. In addition, due to thermal and chemo-physical instabilities, FGF2 is recommended to be freshly added into the media and it requires additional labor and miscellaneous fees. In conclusion, the present inventive opto-FGFR system in livestock PSCs can be a realistic solution to decrease these production costs.

Therefore, in accordance with an embodiment, the present invention provides a synthetic polynucleotide comprising a sequence encoding the intracellular domain of the fibroblast growth factor 1 receptor (FGFR1) fused to a sequence encoding a photoactivatable light-oxygen-voltage sensing (LOV) domain.

In an embodiment the LOV domain has the following nucleotide sequence (SEQ ID NO:7):

```
CCTGACTACAGTCTCGTGAAGGCTCTGCAAATGGCACAACAGAATTT

TGTCATTACAGACGCCTCCCTCCCAGACAACCCTATCGTCTACGCCA

GTAGAGGGTTTCTGACACTGACAGGCTATTCTCTCGACCAGATCCTG

GGCAGGAACTGCAGGTTTCTGCAAGGGCCAGAAACAGACCCAAGAGC

TGTGGATAAGATCAGGAATGCCATCACCAAAGGCGTTGATACCAGTG
```

-continued
```
TCTGTCTGCTGAATTATAGACAGGATGGCACAACCTTCTGGAATCTC

TTCTTCGTGGCTGGACTCAGAGATTCTAAGGGCAATATTGTCAACTA

CGTCGGAGTGCAGTCAAAGGTGAGCGAAGATTATGCCAAGCTGCTGG

TCAACGAGCAGAACATTGAGTACAAAGGTGTGCGCACCAGTAACATG

CTGCGCAGAAAG.
```

In accordance with another embodiment, the present invention provides a synthetic polynucleotide comprising a sequence encoding the intracellular domain of the fibroblast growth factor 1 receptor (FGFR1) fused to a sequence encoding a photoactivatable light-oxygen-voltage sensing (LOV) domain comprising the nucleotide sequence of SEQ ID NO:6.

The term "chimeric" or "fusion" polypeptide or protein refers to a composition comprising at least one polypeptide or peptide sequence or domain that is chemically bound in a linear fashion with a second polypeptide or peptide domain. One embodiment of this invention is an isolated or recombinant nucleic acid molecule encoding a fusion protein comprising at least two domains, wherein the first domain comprises a polypeptide encoding FGFR1 protein, and the second domain comprising a polypeptide encoding a LOV protein.

In some embodiments, the fusion protein is designed for human PSCs.

In some alternative embodiments, the fusion protein is designed for porcine induced PSCs.

In accordance with an embodiment, the present invention provides a synthetic polynucleotide comprising a sequence encoding the intracellular domain of the fibroblast growth factor 1 receptor (FGFR1) fused to a sequence encoding a photoactivatable light-oxygen-voltage sensing (LOV) domain, a promoter sequence and a sequence encoding a myristolation signal peptide (Myr).

In accordance with an embodiment, the present invention provides an expression vector comprising synthetic polynucleotide comprising a sequence encoding the intracellular domain of the fibroblast growth factor 1 receptor (FGFR1) fused to a sequence encoding a photoactivatable proteins, including cryptochrome 2 (CRY2), light, oxygen, and voltage (LOV) domains, phytochrome B (PhyB) and UV-resistance locus 8 (UVR8) and its derivatives.

In some embodiments, the expression vector can be a plasmid.

In accordance with an embodiment, the present invention provides an expression vector comprising synthetic polynucleotide comprising a sequence encoding the intracellular domain of the fibroblast growth factor 1 receptor (FGFR1) fused to a sequence encoding a photoactivatable light-oxygen-voltage sensing (LOV) domain comprising the nucleotide sequence of SEQ ID NO:6.

In accordance with another embodiment, the present invention provides a synthetic polynucleotide comprising a sequence encoding the intracellular domain of the fibroblast growth factor 1 receptor (FGFR1) fused to a sequence encoding a photoactivatable light-oxygen-voltage sensing (LOV) domain, a promoter sequence and a sequence encoding a myristolation signal peptide (Myr). In an embodiment, the AAV-Myr-opto-FGFR-LOV comprising the nucleotide sequence of SEQ ID NO: 1:

```
tgctttctctgaccagcattctctccctgggcctgtgccgctttctgtctgcagcttgtg gcctgggtcacctctacggctgggcccagatccttccctgccgcctccttcaggttccgtct tcctccactccctcttcccttgctctctgctgtgttgctgcccaaggatgctctttccgg agcacttccttctcggcgctgcaccacgtgatgtcctctgagcggatcctcccccgtgtctg ggtcctctccgggcatctctcctccctcacccaacccatgccgtcttcactcgctgggtt ccctttccttctccttctggggcctgtgccatctctcgtttcttaggatggccttctccg acggatgtctcccttgcgtcccgcctcccttcttgtaggcctgcatcatcaccgttttc tggacaacccaaagtaccccgtctccctggctttagccacctctccatcctcttgctttc tttgcctggacaccccgttctcctgtggattcgggtcacctctcactcctttcatttgggc agctcccctaccccccttacctctctagtctgtgctagctcttccagcccctgtcatggc atcttccaggggtccgagagctcagctagtcttcttcctccaacccgggcccctatgtcca cttcaggacagcatgtttgctgcctccagggatcctgtgtccccgagctgggaccaccta tattcccagggccggttaatgtggctctggttctgggtactttttatctgtcccctccaccc cacagtggggcaagcttctgacctcttctcttcctcccacagggcctcgagagatctggca gcggaGAGGGCAGAGGAAGTCTTCTAACATGCGGTGACGTGGAGGAGAATCCCGGCCCTAG

GCTCGAGATGACCGAGTACAAGCCCACGGTGCGCCTCGCCACCCGCGACGACGTCCCCAGG

GCCGTACGCACCCTCGCCGCCGCGTTCGCCGACTACCCCGCCACGCGCCACACCGTCGATC

CGGACCGCCACATCGAGCGGGTCACCGAGCTGCAAGAACTCTTCCTCACGCGCGTCGGGCT

CGACATCGGCAAGGTGTGGGTCGCGGACGACGGCGCCGCGGTGGCGGTCTGGACCACGCCG

GAGAGCGTCGAAGCGGGGGCGGTGTTCGCCGAGATCGGCCCGCGCATGGCCGAGTTGAGCG
```

-continued

```
GTTCCCGGCTGGCCGCGCAGCAACAGATGGAAGGCCTCCTGGCGCCGCACCGGCCCAAGGA
GCCCGCGTGGTTCCTGGCCACCGTCGGCGTCTCGCCCGACCACCAGGGCAAGGGTCTGGGC
AGCGCCGTCGTGCTCCCCGGAGTGGAGGCGGCCGAGCGCGCCGGGGTGCCCGCCTTCCTGG
AGACCTCCGCGCCCCGCAACCTCCCCTTCTACGAGCGGCTCGGCTTCACCGTCACCGCCGA
CGTCGAGGTGCCCGAAGGACCGCGCACCTGGTGCATGACCCGCAAGCCCGGTGCCtgatct
agagggcccgtttaaacccgctgatcagcctcgactgtgccttctagttgccagccatctg
ttgtttgcccctccccgtgccttccttgaccctggaaggtgccactcccactgtcctttc
ctaataaaatgaggaaattgcatcgcattgtctgagtaggtgtcattctattctgggggt
ggggggggcaggacagcaaggggaggattgggaagacaatagcaggcatgctgggatgc
ggtgggctctatgggtctcgacattgattattgactagttattaatagtaatcaattacgg
ggtcattagttcatagcccatatatggagttccgcgttacataacttacggtaaatggccc
gcctggctgaccgcccaacgacccccgcccattgacgtcaataatgacgtatgttcccata
gtaacgccaatagggactttccattgacgtcaatgggtggagtatttacggtaaactgccc
acttggcagtacatcaagtgtatcatatgccaagtacgccccctattgacgtcaatgacgg
taaatggcccgcctggcattatgcccagtacatgaccttatgggactttcctacttggcag
tacatctacgtattagtcatcgctattaccatggtgatgcggttttggcagtacatcaatg
ggcgtggatagcggtttgactcacggggatttccaagtctccacccattgacgtcaatgg
gagtttgttttggcaccaaaatcaacgggactttccaaaatgtcgtaacaactccgcccca
ttgacgcaaatgggcggtaggcgtgtacggtgggaggtctatataagcagagctctctggc
taactagagaacccactgcttactggcttatcgaaattaatacgactcactatagggagac
acaagctggctagcgtttaaacgggccctctagactcgagcggccgcggccaccATGGGGA
GTAGCAAGAGCAAGCCTAAGGACCCCAGCCAGCGCCTCGACATGAAGAGCGGCACCAAGAA
GAGCGACTTCCATAGCCAGATGGCTGTGCACAAGCTGGCCAAGAGCATCCCTCTGCGCAGA
CAGGTAACAGTGTCAGCTGACTCCAGTGCATCCATGAACTCTGGGGTTCTCCTGGTTCGGC
CCTCACGGCTCTCCTCCAGCGGGACCCCCATGCTGGCTGGAGTCTCCGAATATGAGCTCCC
TGAGGATCCCCGCTGGGAGCTGCCACGAGACAGACTGGTCTTAGGCAAACCACTTGGCGAG
GGCTGCTTCGGGCAGGTGGTGTTGGCTGAGGCCATCGGGCTGGATAAGGACAAACCCAAC
CGTGTGACCAAAGTGGCCGTGAAGATGTTGAAGTCCGACGCAACGGAGAAGGACCTGTCG
GATCTGATCTCGGAGATGGAGATGATGAAAATGATTGGGAAGCACAAGAATATCATCAACC
TTCTGGGAGCGTGCACACAGGATGGTCCTCTTTATGTCATTGTGGAGTACGCCTCCAAAGG
CAATCTCCGGGAGTATCTACAGGCCCGGAGGCCTCCTGGGCTGGAGTACTGCTATAACCCC
AGCCACAACCCCGAGGAACAGCTGTCTTCCAAAGATCTGGTATCCTGTGCCTATCAGGTGG
CTCGGGGCATGGAGTATCTTGCCTCTAAGAAGTGTATACACCGAGACCTGGCTGCTAGGAA
CGTCCTGGTGACCGAGGATAACGTAATGAAGATCGCAGACTTTGGCTTAGCTCGAGACATT
CATCATATCGACTACTACAAGAAAACCACCAACGGCCGGCTGCCTGTGAAGTGGATGGCCC
CTGAGGCGTTGTTTGACCGGATCTACACACACCAGAGCGATGTGTGGTCTTTTGGAGTGCT
CTTGTGGGAGATCTTCACTCTGGGTGGCTCCCCATACCCCGGTGTGCCTGTGGAGGAACTT
TTCAAGCTGCTGAAGGAGGGTCATCGAATGGACAAGCCCAGTAACTGTACCAATGAGCTGT
ACATGATGATGCGGGACTGCTGGCATGCAGTGCCCTCTCAGAGACCTACGTTCAAGCAGTT
GGTGGAAGACCTGGACCGCATTGTGGCCTTGACCTCCAACCAGGAGTATCTGGACCTGTCC
ATACCGCTGGACCAGTACTCACCCAGCTTTCCCGACACACGGAGCTCCACCTGCTCCTCAG
```

-continued

```
GGGAGGACTCTGTCTTCTCTCATGAGCCGTTACCTGAGGAGCCCTGTCTGCCTCGACACCC

CACCCAGCTTGCCAACAGTGGACTCAAACGGCGCGTCGAGACCGGTCCTGACTACAGTCTC

GTGAAGGCTCTGCAAATGGCACAACAGAATTTTGTCATTACAGACGCCTCCCTCCCAGACA

ACCCTATCGTCTACGCCAGTAGAGGGTTTCTGACACTGACAGGCTATTCTCTCGACCAGAT

CCTGGGCAGGAACTGCAGGTTTCTGCAAGGGCCAGAAACAGACCCAAGAGCTGTGGATAAG

ATCAGGAATGCCATCACCAAAGGCGTTGATACCAGTGTCTGTCTGCTGAATTATAGACAGG

ATGGCACAACCTTCTGGAATCTCTTCTTCGTGGCTGGACTCAGAGATTCTAAGGGCAATAT

TGTCAACTACGTCGGAGTGCAGTCAAAGGTGAGCGAAGATTATGCCAAGCTGCTGGTCAAC

GAGCAGAACATTGAGTACAAAGGTGTGCGCACCAGTAACATGCTGCGCAGAAAGCCCGGTG

GATCCGGAGTCGACTATCCGTACGACGTACCAGACTACGCACTCGACtaagaattccacca cactggactagtggatccgagctcggtaccaagcttaagactagggacaggattggtgaca gaaaagccccatccttaggcctcctccttcctagtctcctgatattgggtctaacccccac ctcctgttaggcagattccttatctggtgacacaccccatttcctggagccatctctctc cttgccagaacctctaaggtttgcttacgatggagccagagaggatcctgggagggagagc ttggcagggggggagggaaggggggggatgcgtgacctgcccggttctcagtggccaccct gcgctaccctctcccagaacctgagctgctctgacgcggctgtctggtgcgtttcactgat cctggtgctgcagcttccttacacttcccaagaggagaagcagtttggaaaaacaaaatca gaataagttggtcctgagttctaactttggctcttcacctttctagtccccaatttatatt gttcctccgtgcgtcagttttacctgtgagataaggccagtagccagccccgtcctggcag ggctgtggtgaggaggggggtgtccgtgtggaaaactcccttttgtgagaatggtgcgtcct aggtgttcaccaggtcgtggccgcctctactccctttctctttctccatccttctttcctt aaagagtccccagtgctatctgggacatattcctccgcccagagcagggtcccgcttccct aaggccctgctctgggcttctgggtttgagtccttggcaagcccaggagaggcgctcaggc ttccctgtcccccttcctcgtccaccatctcatgcccctggctctcctgccccttccctac aggggttcctggctctgctct.
```

In some embodiments, the plasmid comprises a AAV-CAGGS-eGFP vector where the eGFP region was replaced by a region of the opto-FGFR1 domain from mFGFR1-LOV vector to create a AAV-opto-FGFR.

It will be understood by those of ordinary skill in the art that in one or more embodiments, one can knock-in the AAV-Myr-opto-FGFR-LOV plasmid into the AAV1 locus (safe harbor area with constitutively expressed gene). It will also be understood that in other embodiments, the plasmid can be incorporated into the genetically active loci of stem cells, including human stem cells.

As used herein, the term FGFRF1 means the protein encoded by the FGFR1 gene, and which is a member of the fibroblast growth factor receptor (FGFR) family. The amino acid sequence is highly conserved between members and throughout evolution. FGFR family members differ from one another in their ligand affinities and tissue distribution. A full-length representative protein would consist of an extracellular region, composed of three immunoglobulin-like domains, a single hydrophobic membrane-spanning segment and a cytoplasmic tyrosine kinase domain. The extracellular portion of the protein interacts with fibroblast growth factors, setting in motion a cascade of downstream signals, ultimately influencing mitogenesis and differentiation. A marked difference between this gene product and the other family members is its lack of a cytoplasmic tyrosine kinase domain. The result is a transmembrane receptor that could interact with other family members and potentially inhibit signaling. Multiple alternatively spliced transcript variants encoding the same isoform have been found for this gene N-myristoylation is the attachment of a 14-carbon fatty acid, myristate, onto the N-terminal glycine residue of target proteins, catalyzed by N-myristoyltransferase (NMT), a ubiquitous and essential enzyme in eukaryotes. Many of the target proteins of NMT are crucial components of signalling pathways, and myristoylation typically promotes membrane binding that is essential for proper protein localization or biological function.

The term "variants" as used herein, means that the wild type amino acid sequences comprising the polypeptides of the compositions, may include substituted amino acids.

The term, "amino acid" includes the residues of the natural α-amino acids (e.g., Ala, Arg, Asn, Asp, Cys, Glu, Gln, Gly, His, Lys, Ile, Leu, Met, Phe, Pro, Ser, Thr, Trp, Tyr, and Val) in D or L form, as well as β-amino acids, synthetic and unnatural amino acids. Many types of amino acid residues are useful in the polypeptides and the invention is not limited to natural, genetically-encoded amino acids. Examples of amino acids that can be utilized in the peptides described herein can be found, for example, in Fasman, 1989, CRC Practical Handbook of Biochemistry and Molecular Biology, CRC Press, Inc., and the reference cited therein. Another source of a wide array of amino acid residues is provided by the website of RSP Amino Acids LLC.

The term "peptide" as used herein, includes a sequence of from four to sixteen amino acid residues in which the α-carboxyl group of one amino acid is joined by an amide bond to the main chain (α- or β-) amino group of the adjacent amino acid. The peptides provided herein for use in the described and claimed methods and compositions can be cyclic.

In reference to the fusion polypeptide composition of the present invention, the functional portion can comprise, for instance, about 90%, 95%, or more, of the FGFR1 and/or LOV polypeptide.

The functional portion of the fusion polypeptide composition of the present invention can comprise additional amino acids at the amino or carboxy terminus of the portion, or at both termini, which additional amino acids are not found in the amino acid sequence of either of the wild type FGFR1 and/or LOV polypeptides. Desirably, the additional amino acids do not interfere with the biological function of the functional portion.

Included in the scope of the invention are functional variants of the inventive polypeptides, and proteins described herein. The term "functional variant" as used herein refers to either the FGFR1 and/or LOV polypeptide, or fusion protein having substantial or significant sequence identity or similarity to the FGFR1 and/or LOV polypeptide, or fusion protein, which functional variant retains the biological activity of the FGFR1 and/or LOV polypeptide, or fusion protein of which it is a variant. In reference to the original FGFR1 and/or LOV polypeptide, or protein, the functional variant can, for instance, be at least about 30%, 50%, 75%, 80%, 90%, 98% or more identical in amino acid sequence to the FGFR1 and/or LOV polypeptide, or protein.

The functional variant can, for example, comprise the amino acid sequence of the FGFR1 and/or LOV polypeptide fusion protein with at least one or more conservative amino acid substitutions. Conservative amino acid substitutions are known in the art, and include amino acid substitutions in which one amino acid having certain physical and/or chemical properties is exchanged for another amino acid that has the same chemical or physical properties. For instance, the conservative amino acid substitution can be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc.

Functional variants can also include extensions of the FGFR1 and/or LOV polypeptide fusion protein. For example, a functional variant of the FGFR1 and/or LOV polypeptide fusion protein can include 1, 2, 3, 4 and 5 additional amino acids from either the N-terminal or C-terminal end of the FGFR1 and/or LOV polypeptide fusion protein.

Alternatively or additionally, the functional variants can comprise the amino acid sequence of the FGFR1 and/or LOV polypeptide fusion protein with at least one non-conservative amino acid substitution. In this case, it is preferable for the non-conservative amino acid substitution to not interfere with or inhibit the biological activity of the functional variant. Preferably, the non-conservative amino acid substitution enhances the biological activity of the functional variant, such that the biological activity of the functional variant is increased as compared to the FGFR1 and/or LOV polypeptide fusion protein.

The FGFR1 and/or LOV polypeptide fusion protein can consist essentially of the specified amino acid sequence or sequences described herein, such that other components of the functional variant, e.g., other amino acids, do not materially change the biological activity of the functional variant.

It will be understood by those of ordinary skill in the art that the orientation of the two proteins in the fusion protein construct can be reversed, i.e., the N-terminal protein can comprise the LOV protein and the C-terminal protein can comprise the FGFR1 protein.

Analogs and mimetics include molecules which include molecules which contain non-naturally occurring amino acids or which do not contain amino acids but nevertheless behave functionally the same as the peptide. Natural product screening is one useful strategy for identifying analogs and mimetics.

Examples of incorporating non-natural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, omithine, sarcosine, 4-amino-3-hydroxy-6-methylheptanoic acid, 2-thienyl alanine and/or D-isomers of amino acids. A partial list of known non-natural amino acid contemplated herein is shown in Table 1.

TABLE 1

Non-natural Amino Acids

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbomyl-carboxylate | Norb | L-N-methylglutamine | Nmgln |
|  |  | L-N-methylglutamic acid | Nmglu |
| cyclohexylalanine |  | Chexa L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |

TABLE 1-continued

Non-natural Amino Acids

| Non-conventional amino acid | Code | Non-conventional amino acid | Code |
|---|---|---|---|
| D-α-methylalanine | Dmala | α-methylcyclohexylalanine | Mchexa |
| D-α-methylarginine | Dmarg | α-methyl-cylcopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methyl-phenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylaspartate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl))glycine | Nser |
| D-N-methylisoleucine | Dnmile | N-(imidazolylethyl)glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methyl-aminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methyl-phenylalanine | Mphe | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomophenylalanine | Nmhphe |
| N-(N-(2,2-diphenylethyl)carbamylmethyl)glycine | Nnbhm | N-(N-(3,3-diphenylpropyl)carbamylmethyl)glycine | Nnbhe |
| 1-carboxy-1-(2,2-diphenyl-ethylamino)cyclopropane | Nmbc | | |

Analogs of the subject peptides contemplated herein include modifications to side chains, incorporation of non-natural amino acids and/or their derivatives during peptide synthesis and the use of crosslinkers and other methods which impose conformational constraints on the peptide molecule or their analogs.

Examples of side chain modifications contemplated by the present invention include modifications of amino groups such as by reductive alkylation by reaction with an aldehyde followed by reduction with $NaBH_4$; amidination with methylacetimidate; acylation with acetic anhydride; carbamoylation of amino groups with cyanate; trinitrobenzylation of amino groups with 2, 4, 6-trinitrobenzene sulphonic acid (TNBS); acylation of amino groups with succinic anhydride and tetrahydrophthalic anhydride; and pyridoxylation of lysine with pyridoxal-5-phosphate followed by reduction with $NaBH_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitization, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Crosslinkers can be used, for example, to stabilize 3D conformations, using homo-bifunctional crosslinkers such as the bifunctional imido esters having $(CH2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH). In addition, peptides can be conformationally constrained by, for example, incorporation of $C_\alpha$ and $N_\alpha$-methylamino acids, introduction of double bonds between $C_\alpha$ and $C_\beta$ atoms of amino acids and the formation of cyclic peptides or analogues by introducing covalent bonds such as forming an amide bond between the N and C termini, between two side chains or between a side chain and the N or C terminus.

In some embodiments, the FGFR1 protein in the fusion protein is mammalian. In certain embodiments, the FGFR1 protein can be murine, porcine, ovine, bovine, human, or combinations thereof.

In accordance with an embodiment, the present invention provides a composition comprising a polypeptide encoding human FGFR1 protein, or a functional portion or fragment, or variant thereof, linked to a polypeptide encoding LOV protein, or a functional portion or fragment, or variant thereof.

In accordance with an embodiment, the present invention provides expression vectors comprising the synthetic polynucleotides described herein. In one embodiment, the present invention provides an expression cassette specific for use with the CRISPR/Cas9 system. In an embodiment, a gRNA sequence (GTCCCCTCCACCCCACAGTG) (SEQ ID NO:9) is used to target AAVS1 locus.

A "CRISPR," "CRISPR system," or "CRISPR nuclease system" and their grammatical equivalents can include a non-coding RNA molecule (e.g., guide RNA) that binds to DNA and Cas proteins (e.g., Cas9) with nuclease functionality (e.g., two nuclease domains). See, e.g., Sander, J. D., et al., "CRISPR-Cas systems for editing, regulating and targeting genomes," Nature Biotechnology, 32:347-355 (2014); see also e.g., Hsu, P. D., et al., "Development and applications of CRISPR-Cas9 for genome engineering," Cell 157(6):1262-1278 (2014).

The term "gene editing" and its grammatical equivalents as used herein can refer to genetic engineering in which one or more nucleotides are inserted, replaced, or removed from a genome. Gene editing can be performed using a nuclease (e.g., a natural-existing nuclease or an artificially engineered nuclease).

The term "safe harbor" and "immune safe harbor", and their grammatical equivalents as used herein can refer to a location within a genome that can be used for integrating exogenous nucleic acids wherein the integration does not cause any significant effect on the growth of the host cell by the addition of the nucleic acid alone. Non-limiting examples of safe harbors can include HPRT, AAVS SITE (e.g., AAVS1, AAVS2, etc.), CCR5, or Rosa26.

Site specific gene editing can be achieved using non-viral gene editing such as CRISPR, TALEN (see U.S. patent application Ser. No. 14/193,037), transposon-based, ZEN, meganuclease, or Mega-TAL, or Transposon-based system. For example, PiggyBac (see Moriarty, B. S., et al., "Modular assembly of transposon integratable multigene vectors using RecWay assembly," Nucleic Acids Research (8):e92 (2013) or sleeping beauty (see Aronovich, E. L, et al., "The Sleeping Beauty transposon system: a non-viral vector for gene therapy," Hum. Mol. Genet., 20(Rl): R14-R20. (2011) transposon systems can be used.

Site specific gene editing can also be achieved without homologous recombination. An exogenous polynucleic acid can be introduced into a cell genome without the use of homologous recombination. In some cases, a transgene can be flanked by engineered sites that are complementary to a targeted double strand break region in a genome. A transgene can be excised from a polynucleic acid so it can be inserted at a double strand break region without homologous recombination.

CRISPR System

Methods described herein can take advantage of a CRISPR system. There are at least five types of CRISPR systems which all incorporate RNAs and Cas proteins. Types I, III, and IV assemble a multi-Cas protein complex that is capable of cleaving nucleic acids that are complementary to the crRNA. Types I and III both require pre-crRNA processing prior to assembling the processed crRNA into the multi-Cas protein complex. Types II and V CRISPR systems comprise a single Cas protein complexed with at least one guiding RNA.

The general mechanism and recent advances of CRISPR system is discussed in Cong, L. et al., "Multiplex genome engineering using CRISPR systems," Science, 339(6121): 819-823 (2013); Fu, et al., "High-frequency off-target mutagenesis induced by CRISPR-Cas nucleases in human cells," Nature Biotechnology, 31, 822-826 (2013); Chu, V T et al. "Increasing the efficiency of homology-directed repair for CRISPR-Cas9-induced precise gene editing in mammalian cells," Nature Biotechnology 33, 543-548 (2015); Shmakov, S. et al., "Discovery and functional characterization of diverse Class 2 CRISPR-Cas systems," Molecular Cell, 60, 1-13 (2015); Makarova, K S et al., "An updated evolutionary classification of CRISPR-Cas systems,", Nature Reviews Microbiology, 13, 1-15 (2015). Site-specific cleavage of a target DNA occurs at locations determined by both 1) base-pairing complementarity between the guide RNA and the target DNA (also called a protospacer) and 2) a short motif in the target DNA referred to as the protospacer adjacent motif (PAM). For example, an engineered cell can be generated using a CRISPR system, e.g., a type II CRISPR system. A Cas enzyme used in the methods disclosed herein can be Cas9, which catalyzes DNA cleavage. Enzymatic action by Cas9 derived from *Streptococcus pyogenes* or any closely related Cas9 can generate double stranded breaks at target site sequences which hybridize to 20 nucleotides of a guide sequence and that have a protospacer-adjacent motif (PAM) following the 20 nucleotides of the target sequence.

Cas Protein

A vector can be operably linked to an enzyme-coding sequence encoding a CRISPR enzyme, such as a Cas protein (CRISPR-associated protein). Non-limiting examples of Cas proteins can include Cas l, Cas lB, Cas2, Cas3, Cas4, Cas5, Cas6, Cas7, Cas8, Cas9 (also known as Csn l or Csx12), Cas lO, Csyl, Csy2, Csy3, Cse l, Cse2, Csc l, Csc2, Csa5, Csn2, Csm2, Csm3, Csm4, Csm5, Csm6, Cmrl, Cmr3, Cmr4, Cmr5, Cmr6, Csb 1, Csb2, Csb3, Csxl 7, Csxl4, CsxlO, Csxl6, CsaX, Csx3, Csxl, CsxlS, Csfl, Csf2, CsO, Csf4, Cpfl, c2c 1, c2c3, Cas9HiFi, homologues thereof, or modified versions thereof An unmodified CRISPR enzyme can have DNA cleavage activity, such as Cas9. A CRISPR enzyme can direct cleavage of one or both strands at a target sequence, such as within a target sequence and/or within a complement of a target sequence. For example, a CRISPR enzyme can direct cleavage of one or both strands within or within about 1, 2, 3, 4, 5, 6, 7, 8, 9, 10, 15, 20, 25, 50, 100, 200, 500, or more base pairs from the first or last nucleotide of a target sequence. A vector that encodes a CRISPR enzyme that is mutated with respect to a corresponding wild-type enzyme such that the mutated CRISPR enzyme lacks the ability to cleave one or both strands of a target polynucleotide containing a target sequence can be used. A Cas protein can be a high fidelity cas protein such as Cas9HiFi.

A vector that encodes a CRISPR enzyme comprising one or more nuclear localization sequences (NLSs), such as more than or more than about 1, 2, 3, 4, 5, 6, 7, 8, 9, 10, NLSs can be used. For example, a CRISPR enzyme can comprise more than or more than about 1, 2, 3, 4, 5, 6, 7, 8, 9, 10, NLSs at or near the ammo-terminus, more than or more than about 1, 2, 3, 4, 5, 6, 7, 8, 9, 10, NLSs at or near the carboxyl-terminus, or any combination of these (e.g., one or more NLS at the ammo-terminus and one or more NLS at the carboxyl terminus). When more than one NLS is present, each can be selected independently of others, such that a single NLS can be present in more than one copy and/or in combination with one or more other NLSs present in one or more copies.

Cas9 can refer to a polypeptide with at least or at least about 50%, 60%, 70%, 80%, 90%, 100% sequence identity and/or sequence similarity to a wild type exemplary Cas9 polypeptide (e.g., Cas9 from *S. pyogenes*). Cas9 can refer to a polypeptide with at most or at most about 50%, 60%, 70%, 80%, 90%, 100% sequence identity and/or sequence similarity to a wild type exemplary Cas9 polypeptide (e.g., from *S. pyogenes*). Cas9 can refer to the wild type or a modified form of the Cas9 protein that can comprise an amino acid change such as a deletion, insertion, substitution, variant, mutation, fusion, chimera, or any combination thereof.

A polynucleotide encoding an endonuclease (e.g., a Cas protein such as Cas9) can be codon optimized for expression in particular cells, such as eukaryotic cells. This type of optimization can entail the mutation of foreign-derived (e.g., recombinant) DNA to mimic the codon preferences of the intended host organism or cell while encoding the same protein.

CRISPR enzymes used in the methods can comprise NLSs. The NLS can be located anywhere within the polypeptide chain, e.g., near the N- or C-terminus. For example, the NLS can be within or within about 1, 2, 3, 4, 5, 10, 15, 20, 25, 30, 40, 50 amino acids along a polypeptide chain from the N- or C-terminus. Sometimes the NLS can be within or within about 50 amino acids or more, e.g., 100, 200, 300, 400, 500, 600, 700, 800, 900, or 1000 amino acids from the N- or C-terminus.

An endonuclease can comprise an amino acid sequence having at least or at least about 50%, 60%, 70%, 75%, 80%, 85%, 90%, 95%, 99%, or 100%, amino acid sequence identity to the nuclease domain of a wild type exemplary site-directed polypeptide (e.g., Cas9 from *S. pyogenes*).

While *S. pyogenes* Cas9 (SpCas9) is commonly used as a CRISPR endonuclease for genome engineering, it may not be the best endonuclease for every target excision site. For example, the PAM sequence for SpCas9 (5' NGG 3') is abundant throughout the human genome, but a NGG sequence may not be positioned correctly to target a desired gene for modification. In some cases, a different endonuclease may be used to target certain genomic targets. In some cases, synthetic SpCas9-derived variants with non-NGG PAM sequences may be used. Additionally, other Cas9 orthologues from various species have been identified and these "non-SpCas9s" bind a variety of PAM sequences that could also be useful for the present invention. For example, the relatively large size of SpCas9 (approximately 4 kb coding sequence) means that plasmids carrying the SpCas9 cDNA may not be efficiently expressed in a cell. Conversely, the coding sequence for *Staphylococcus aureus* Cas9 (SaCas9) is approximately 1 kilobase shorter than SpCas9, possibly allowing it to be efficiently expressed in a cell. Similar to SpCas9, the SaCas9 endonuclease is capable of modifying target genes in mammalian cells in vitro and in mice in vivo.

Alternatives to *S. pyogenes* Cas9 may include RNA-guided endonucleases from the Cpf1 family that display cleavage activity in mammalian cells. Unlike Cas9 nucleases, the result of Cpf1-mediated DNA cleavage is a double-strand break with a short 3' overhang. Cpf1's staggered cleavage pattern may open up the possibility of directional gene transfer, analogous to traditional restriction enzyme cloning, which may increase the efficiency of gene editing. Like the Cas9 variants and orthologues described above, Cpf1 may also expand the number of sites that can be targeted by CRISPR to AT-rich regions or AT-rich genomes that lack the NGG PAM sites favored by SpCas9.

Any functional concentration of Cas protein can be introduced to a cell. For example, 15 micrograms of Cas mRNA can be introduced to a cell. In other cases, a Cas mRNA can be introduced from 0.5 micrograms to 100 micrograms. A Cas mRNA can be introduced from 0.5, 5, 10, 15, 20, 25, 30, 35, 40, 45, 50, 55, 60, 65, 70, 75, 80, 85, 90, 95, or 100 micrograms.

GuideRNA

As used herein, the term "guide RNA (gRNA)", and its grammatical equivalents can refer to an RNA which can be specific for a target DNA and can form a complex with a Cas protein. A guide RNA can comprise a guide sequence, or spacer sequence, that specifies a target site and guides an RNA/Cas complex to a specified target DNA for cleavage. For example, FIG. 15, demonstrates that guide RNA can target a CRISPR complex to three genes and perform a targeted double strand break. Site-specific cleavage of a target DNA occurs at locations determined by both 1) base-pairing complementarity between a guide RNA and a target DNA (also called a protospacer) and 2) a short motif in a target DNA referred to as a protospacer adjacent motif (PAM).

A method disclosed herein also can comprise introducing into a cell or embryo at least one guide RNA or nucleic acid, e.g., DNA encoding at least one guide RNA. A guide RNA can interact with a RNA-guided endonuclease to direct the endonuclease to a specific target site, at which site the 5' end of the guide RNA base pairs with a specific protospacer sequence in a chromosomal sequence.

A guide RNA can comprise two RNAs, e.g., CRISPR RNA (crRNA) and transactivating crRNA (tracrRNA). A guide RNA can sometimes comprise a single-guide RNA (sgRNA) formed by fusion of a portion (e.g., a functional portion) of crRNA and tracrRNA. A guide RNA can also be a dual RNA comprising a crRNA and a tracrRNA. A guide RNA can comprise a crRNA and lack a tracrRNA. Furthermore, a crRNA can hybridize with a target DNA or protospacer sequence.

As discussed above, a guide RNA can be an expression product. For example, a DNA that encodes a guide RNA can be a vector comprising a sequence coding for the guide RNA. A guide RNA can be transferred into a cell or organism by transfecting the cell or organism with an isolated guide RNA or plasmid DNA comprising a sequence coding for the guide RNA and a promoter. A guide RNA can also be transferred into a cell or organism in other way, such as using virus-mediated gene delivery.

A guide RNA can be isolated. For example, a guide RNA can be transfected in the form of an isolated RNA into a cell or organism. A guide RNA can be prepared by in vitro transcription using any in vitro transcription system. A guide RNA can be transferred to a cell in the form of isolated RNA rather than in the form of plasmid comprising encoding sequence for a guide RNA.

A guide RNA can comprise a DNA-targeting segment and a protein binding segment. A DNA-targeting segment (or DNA-targeting sequence, or spacer sequence) comprises a nucleotide sequence that can be complementary to a specific sequence within a target DNA (e.g., a protospacer). A protein-binding segment (or protein-binding sequence) can interact with a site-directed modifying polypeptide, e.g., an RNA-guided endonuclease such as a Cas protein. By "segment" it is meant a segment/section/region of a molecule, e.g., a contiguous stretch of nucleotides in an RNA. A segment can also mean a region/section of a complex such that a segment may comprise regions of more than one molecule. For example, in some cases a protein-binding segment of a DNA-targeting RNA is one RNA molecule and the protein-binding segment therefore comprises a region of that RNA molecule. In other cases, the protein-binding segment of a DNA-targeting RNA comprises two separate molecules that are hybridized along a region of complementarity.

A guide RNA can comprise two separate RNA molecules or a single RNA molecule. An exemplary single molecule guide RNA comprises both a DNA-targeting segment and a protein-binding segment.

An exemplary two-molecule DNA-targeting RNA can comprise a crRNA-like ("CRISPR RNA" or "targeter-RNA" or "crRNA" or "crRNA repeat") molecule and a corresponding tracrRNA-like ("trans-acting CRISPR RNA" or "activator-RNA" or "tracrRNA") molecule. A first RNA molecule can be a crRNA-like molecule (targeter-RNA), that can comprise a DNA-targeting segment (e.g., spacer) and a stretch of nucleotides that can form one half of a double-stranded RNA (dsRNA) duplex comprising the protein-binding segment of a guide RNA. A second RNA molecule can be a corresponding tracrRNA-like molecule (activator-RNA) that can comprise a stretch of nucleotides that can form the other half of a dsRNA duplex of a protein-binding segment of a guide RNA. In other words, a stretch of nucleotides of a crRNA-like molecule can be complementary to and can hybridize with a stretch of nucleotides of a tracrRNA-like molecule to form a dsRNA duplex of a protein-binding domain of a guide RNA. As such, each crRNA-like molecule can be said to have a corresponding tracrRNA-like molecule. A crRNA-like molecule additionally can provide a single stranded DNA-targeting segment, or spacer sequence. Thus, a crRNA-like and a tracrRNA-like molecule (as a corresponding pair) can hybridize to form a guide RNA. A subject two-molecule guide RNA can comprise any corresponding crRNA and tracrRNA pair.

A DNA-targeting segment or spacer sequence of a guide RNA can be complementary to sequence at a target site in a chromosomal sequence, e.g., protospacer sequence) such that the DNA-targeting segment of the guide RNA can base pair with the target site or protospacer. In some cases, a DNA-targeting segment of a guide RNA can comprise from or from about 10 nucleotides to from or from about 25 nucleotides or more. For example, a region of base pairing between a first region of a guide RNA and a target site in a chromosomal sequence can be or can be about 10, 11, 12, 13, 14, 15, 16, 17, 18, 19, 20, 22, 23, 24, 25, or more than 25 nucleotides in length. Sometimes, a first region of a guide RNA can be or can be about 19, 20, or 21 nucleotides in length.

A guide RNA can target a nucleic acid sequence of or of about 20 nucleotides. A target nucleic acid can be less than or less than about 20 nucleotides. A target nucleic acid can be at least or at least about 5, 10, 15, 16, 17, 18, 19, 20, 21, 22, 23, 24, 25, 30 or more nucleotides. A target nucleic acid can be at most or at most about 5, 10, 15, 16, 17, 18, 19, 20, 21, 22, 23, 24, 25, 30 or more nucleotides. A target nucleic acid sequence can be or can be about 20 bases immediately 5' of the first nucleotide of the PAM. A guide RNA can target the nucleic acid sequence.

A guide nucleic acid, for example, a guide RNA, can refer to a nucleic acid that can hybridize to another nucleic acid, for example, the target nucleic acid or protospacer in a genome of a cell. A guide nucleic acid can be RNA. A guide nucleic acid can be DNA. The guide nucleic acid can be programmed or designed to bind to a sequence of nucleic acid site-specifically. A guide nucleic acid can comprise a polynucleotide chain and can be called a single guide nucleic acid. A guide nucleic acid can comprise two polynucleotide chains and can be called a double guide nucleic acid.

A guide nucleic acid can comprise one or more modifications to provide a nucleic acid with a new or enhanced feature. A guide nucleic acid can comprise a nucleic acid affinity tag. A guide nucleic acid can comprise synthetic nucleotide, synthetic nucleotide analog, nucleotide derivatives, and/or modified nucleotides.

A guide nucleic acid can comprise a nucleotide sequence (e.g., a spacer), for example, at or near the 5' end or 3' end, that can hybridize to a sequence in a target nucleic acid (e.g., a protospacer). A spacer of a guide nucleic acid can interact with a target nucleic acid in a sequence-specific manner via hybridization (i.e., base pairing). A spacer sequence can hybridize to a target nucleic acid that is located 5' or 3' of a protospacer adjacent motif (PAM). The length of a spacer sequence can be at least or at least about 5, 10, 15, 16, 17, 18, 19, 20, 21, 22, 23, 24, 25, 30 or more nucleotides. The length of a spacer sequence can be at most or at most about 5, 10, 15, 16, 17, 18, 19, 20, 21, 22, 23, 24, 25, 30 or more nucleotides.

A guide RNA can also comprises a dsRNA duplex region that forms a secondary structure. For example, a secondary structure formed by a guide RNA can comprise a stem (or hairpin) and a loop. A length of a loop and a stem can vary. For example, a loop can range from about 3 to about 10 nucleotides in length, and a stem can range from about 6 to about 20 base pairs in length. A stem can comprise one or more bulges of 1 to about 10 nucleotides. The overall length of a second region can range from about 16 to about 60 nucleotides in length. For example, a loop can be or can be about 4 nucleotides in length and a stem can be or can be about 12 base pairs. A dsRNA duplex region can comprise a protein-binding segment that can form a complex with an RNA-binding protein, such as a RNA-guided endonuclease, e.g., Cas protein.

A guide RNA can also comprise a tail region at the 5' or 3' end that can be essentially single-stranded. For example, a tail region is sometimes not complementarity to any chromosomal sequence in a cell of interest and is sometimes not complementarity to the rest of a guide RNA. Further, the length of a tail region can vary. A tail region can be more than or more than about 4 nucleotides in length. For example, the length of a tail region can range from or from about 5 to from or from about 60 nucleotides in length.

A guide RNA can be introduced into a cell or embryo as an RNA molecule. For example, a RNA molecule can be transcribed in vitro and/or can be chemically synthesized. A guide RNA can then be introduced into a cell or embryo as an RNA molecule. A guide RNA can also be introduced into a cell or embryo in the form of a non-RNA nucleic acid molecule, e.g., DNA molecule. For example, a DNA encoding a guide RNA can be operably linked to promoter control sequence for expression of the guide RNA in a cell or embryo of interest. A RNA coding sequence can be operably linked to a promoter sequence that is recognized by RNA polymerase III (Pol III).

A DNA molecule encoding a guide RNA can also be linear. A DNA molecule encoding a guide RNA can also be circular.

A DNA sequence encoding a guide RNA can also be part of a vector. Some examples of vectors can include plasmid vectors, phagemids, cosmids, artificial/mini-chromosomes, transposons, and viral vectors. For example, a DNA encoding a RNA-guided endonuclease is present in a plasmid vector. Other non-limiting examples of suitable plasmid vectors include pUC, pBR322, pET, pBluescript, and variants thereof. Further, a vector can comprise additional expression control sequences (e.g., enhancer sequences, Kozak sequences, polyadenylation sequences, transcriptional termination sequences, etc.), selectable marker sequences (e.g., antibiotic resistance genes), origins of replication, and the like.

When both a RNA-guided endonuclease and a guide RNA are introduced into a cell as DNA molecules, each can be part of a separate molecule (e.g., one vector containing fusion protein coding sequence and a second vector containing guide RNA coding sequence) or both can be part of a same molecule (e.g., one vector containing coding (and regulatory) sequence for both a fusion protein and a guide RNA).

A Cas protein, such as a Cas9 protein or any derivative thereof, can be pre-complexed with a guide RNA to form a ribonucleoprotein (RNP) complex. The RNP complex can be introduced into primary immune cells. Introduction of the RNP complex can be timed. The cell can be synchronized with other cells at G1, S, and/or M phases of the cell cycle. The RNP complex can be delivered at a cell phase such that HDR is enhanced. The RNP complex can facilitate homology directed repair.

A guide RNA can also be modified. The modifications can comprise chemical alterations, synthetic modifications, nucleotide additions, and/or nucleotide subtractions. The modifications can also enhance CRISPR genome engineering. A modification can alter chirality of a gRNA. In some cases, chirality may be uniform or stereopure after a modification. A guide RNA can be synthesized. The synthesized guide RNA can enhance CRISPR genome engineering. A guide RNA can also be truncated. Truncation can be used to reduce undesired off-target mutagenesis. The truncation can comprise any number of nucleotide deletions. For example, the truncation can comprise 1, 2, 3, 4, 5, 10, 15, 20, 25, 30, 40, 50 or more nucleotides. A guide RNA can comprise a region of target complementarity of any length. For example, a region of target complementarity can be less than 20 nucleotides in length. A region of target complementarity can be more than 20 nucleotides in length.

In some cases, a dual nickase approach may be used to introduce a double stranded break. Cas proteins can be mutated at known amino acids within either nuclease domains, thereby deleting activity of one nuclease domain and generating a nickase Cas protein capable of generating a single strand break. A nickase along with two distinct guide RNAs targeting opposite strands may be utilized to generate a DSB within a target site (often referred to as a "double nick" or "dual nickase" CRISPR system). This approach may dramatically increase target specificity, since it is unlikely that two off-target nicks will be generated within close enough proximity to cause a DSB.

In some cases, a GUIDE-Seq analysis can be performed to determine the specificity of engineered guide RNAs. The general mechanism and protocol of GUIDE-Seq profiling of off-target cleavage by CRISPR system nucleases is discussed in Tsai, S. et al., "GUIDE-Seq enables genome-wide profiling of off-target cleavage by CRISPR system nucleases," Nature, 33: 187-197 (2015).

A gRNA can be introduced at any functional concentration. For example, a gRNA can be introduced to a cell at 10 micrograms. In other cases, a gRNA can be introduced from 0.5 micrograms to 100 micrograms. A gRNA can be introduced from 0.5, 5, 10, 15, 20, 25, 30, 35, 40, 45, 50, 55, 60, 65, 70, 75, 80, 85, 90, 95, or 100 micrograms.

In some cases, a method can comprise an endonuclease selected from the group consisting of Cas 1, Cas 1B, Cas2, Cas3, Cas4, Cas5, Cas6, Cas7, Cas8, Cas9, Cas 10, Csy 1, Csy2, Csy3, Cse1, Cse2, Cscl, Csc2, Csa5, Csn2, Csm2, Csm3, Csm4, Csm5, Csm6, Cmrl, Cmr3, Cmr4, Cmr5, Cmr6, Csb 1, Csb2, Csb3, Csxl 7, Csxl4, CsxlO, Csxl6, CsaX, Csx3, Csxl, CsxlS, Csfl, Csf2, Cs0, Csf4, Cpfl, c2cl, c2c3, Cas9HiFi, homologues thereof or modified versions thereof Δ Cas protein can be Cas9. In some cases, a method can further comprise at least one guide RNA (gRNA). A gRNA can comprise at least one modification. An exogenous TCR can bind a cancer neo-antigen.

Disclosed herein is a method of making an engineered cell comprising: introducing at least one polynucleic acid encoding at least one exogenous LOV receptor sequence; introducing at least one guide RNA (gRNA) comprising at least one modification; and introducing at least one endonuclease; wherein the gRNA comprises at least one sequence complementary to at least one endogenous genome. In some cases, a modification is on a 5' end, a 3' end, from a 5' end to a 3' end, a single base modification, a 2'-ribose modification, or any combination thereof Δ modification can be selected from a group consisting of base substitutions, insertions, deletions, chemical modifications, physical modifications, stabilization, purification, and any combination thereof.

In accordance with an embodiment, the present invention provides a transformant transformed by the vectors described herein, including, for example, mammalian cells, and specifically, pluripotent stem cells.

In some embodiments, the transformant is a stem cell. In other embodiments, the transformant is a human derived stem cell.

In further embodiments, the transformant is a stem cell from a mammal, such as a pig, cow, sheep, goat, chicken or other livestock animal.

The invention further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae. The host cell can be a cultured cell or a primary cell, i.e., isolated directly from an organism, e.g., a human or pig. The host cell can be an adherent cell or a suspended cell, i.e., a cell that grows in suspension. Suitable host cells are known in the art and include, for instance, stem cells. In some preferred embodiments, the host cells are pluripotent stem cells of human or porcine derivation.

Also provided by the invention is a population of cells comprising at least one host cell described herein. The population of cells can be a substantially homogeneous population, in which the population comprises mainly of host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

The host referred to in the inventive methods can be any host. Preferably, the host is a mammal. As used herein, the term "mammal" refers to any mammal, including, but not limited to, mammals of the order Rodentia, such as mice and hamsters, and mammals of the order Lagomorpha, such as rabbits. It is preferred that the mammals are from the order Carnivora, including Felines (cats) and Canines (dogs). It is more preferred that the mammals are from the order Artiodactyla, including Bovine (cows) and Swine (pigs) or of the order Perssodactyla, including Equine (horses). It is most preferred that the mammals are of the order Primates, Ceboids, or Simoids (monkeys) or of the order Anthropoids (humans and apes). An especially preferred mammal is the pig.

Stem cells for use in the methods disclosed herein are not limited in any way and may be obtained from any source. Preferably the stem cells are pluripotent stem cells that are obtained from a mammalian source.

The term "nucleic acid" as used herein, includes "polynucleotide," "oligonucleotide," and "nucleic acid molecule," and generally means an isolated or purified polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. In some embodiments, the nucleic acid does not comprise any insertions, deletions, inversions, and/or substitutions. However, it may be suitable in some instances, as discussed herein, for the nucleic acid to comprise one or more insertions, deletions, inversions, and/or substitutions.

Preferably, the nucleic acids of the invention are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The nucleic acids can be constructed based on chemical synthesis and/or enzymatic ligation reactions using procedures known in the art. See, for example, Sambrook et al., Molecular Cloning: A Laboratory Manual, $3^{rd}$ ed., Cold Spring Harbor Press, Cold Spring Harbor, N Y 2001; and Ausubel et al., Current Protocols in Molecular Biology, Greene Publishing Associates and John Wiley & Sons, N Y, 1994. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxy acetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, CO) and Synthegen (Houston, TX).

The invention also provides an isolated or purified nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The term "isolated" as used herein means having been removed from its natural environment. The term "purified" as used herein means having been increased in purity, wherein "purity" is a relative term, and not to be necessarily construed as absolute purity. For example, the purity can be at least about 50%, can be greater than 60%, 70% or 80%, or can be 100%.

The term "primer" refers to an oligonucleotide, whether natural or synthetic, capable of acting as a point of initiation of DNA synthesis under conditions in which synthesis of a primer extension product complementary to a nucleic acid strand is induced, i.e., in the presence of four different nucleoside triphosphates and an agent for polymerization (i.e., DNA polymerase or reverse transcriptase) in an appropriate buffer and at a suitable temperature. A primer is preferably a single-stranded oligodeoxyribonucleotide. The appropriate length of a primer depends on the intended use of the primer but typically ranges from about 10 to about 30 nucleotides. Short primer molecules generally require cooler temperatures to form sufficiently stable hybrid complexes with the template. A primer need not reflect the exact sequence of the template but must be sufficiently complementary to specifically hybridize with a template. When primer pairs are referred to herein, the pair is meant to include one forward primer which is capable of hybridizing to the sense strand of a double-stranded target nucleic acid (the "sense primer") and one reverse primer which is capable of hybridizing to the antisense strand of a double-stranded target nucleic acid (the "antisense primer").

"Probe" refers to an oligonucleotide which binds through complementary base pairing to a sub-sequence of a target nucleic acid. A primer may be a probe. It will be understood by one of skill in the art that probes will typically substantially bind target sequences lacking complete complementarity with the probe sequence depending upon the stringency of the hybridization conditions. The probes are typically directly labeled (e.g., with isotopes or fluorescent moieties) or indirectly labeled such as with biotin to which a streptavidin complex may later bind. By assaying for the presence or absence of the probe, one can detect the presence or absence of the target, by Southern blot for example.

The recombinant expression vectors of the invention can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColE1, 2μ plasmid, k, SV40, bovine papilloma virus, and the like.

In some exemplary embodiments, the CRISPR system has been used in this system to permanently incorporate the opto-FGFR system into the human stem cells. We specifically target the AAVS1 locus (a safe-harbor region with constitutive expression).

Desirably, the recombinant expression vector comprises regulatory sequences, such as transcription and translation initiation and termination codons, which are specific to the type of host (e.g., bacterium, fungus, plant, or animal) into which the vector is to be introduced, as appropriate and taking into consideration whether the vector is DNA or RNA based.

The recombinant expression vector can include one or more marker genes, which allow for selection of transformed or transfected hosts. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, puromycin resistance genes and ampicillin resistance genes.

The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, the tet-on promoter, or the ubiquitin C promoter, for example. Fibroblast growth factor (FGF) free pluripotent stem cell culture systems.

Currently, there are a few prior art culture optogenetics systems on the market, but these systems are all very expensive. High cost commercial products prevent large volume optogenetics studies and thus, limit the rate of research in this field. There is also a lack of instrumentation that allows for precise control of illumination and remote monitoring of multiple culture plates.

In accordance with some embodiments, the fibroblast growth factor free pluripotent stem cell culture system of the present invention is a hardware, software, and mobile application system capable of precise control and real-time monitoring of cell culture illumination that can serve as an inexpensive alternative to high cost commercial products. The inventive illumination system is designed to be easy-to-assemble, easy-to-use, and low-cost, utilizing 3D printing of thermoplastic materials, programmable open-source electronics, and other readily-available electronic parts. Additionally, the inventive illumination system was designed to be adjustable and be customized to the individual researcher. The 3D models and source code are publicly available to be edited for any specific needs. Additionally, the LED illuminating device of the inventive illumination system can be customized with any color LED to be used with any photosynthetic protein of interest. The inventive illumination system provides the opportunity to apply a flexible optical culture system to cell cultures in any laboratory.

As such, in accordance with an embodiment, the present invention provides a fibroblast growth factor free pluripotent stem cell culture system comprising one or more transformed cells as described herein and an illumination source.

In accordance with an embodiment, the present invention provides a cell culture illumination system comprising a cell culture substrate, an upper and lower enclosure, one or more illumination sources, one or more circuit boards, a power source, and a microcontroller.

Figure 16:
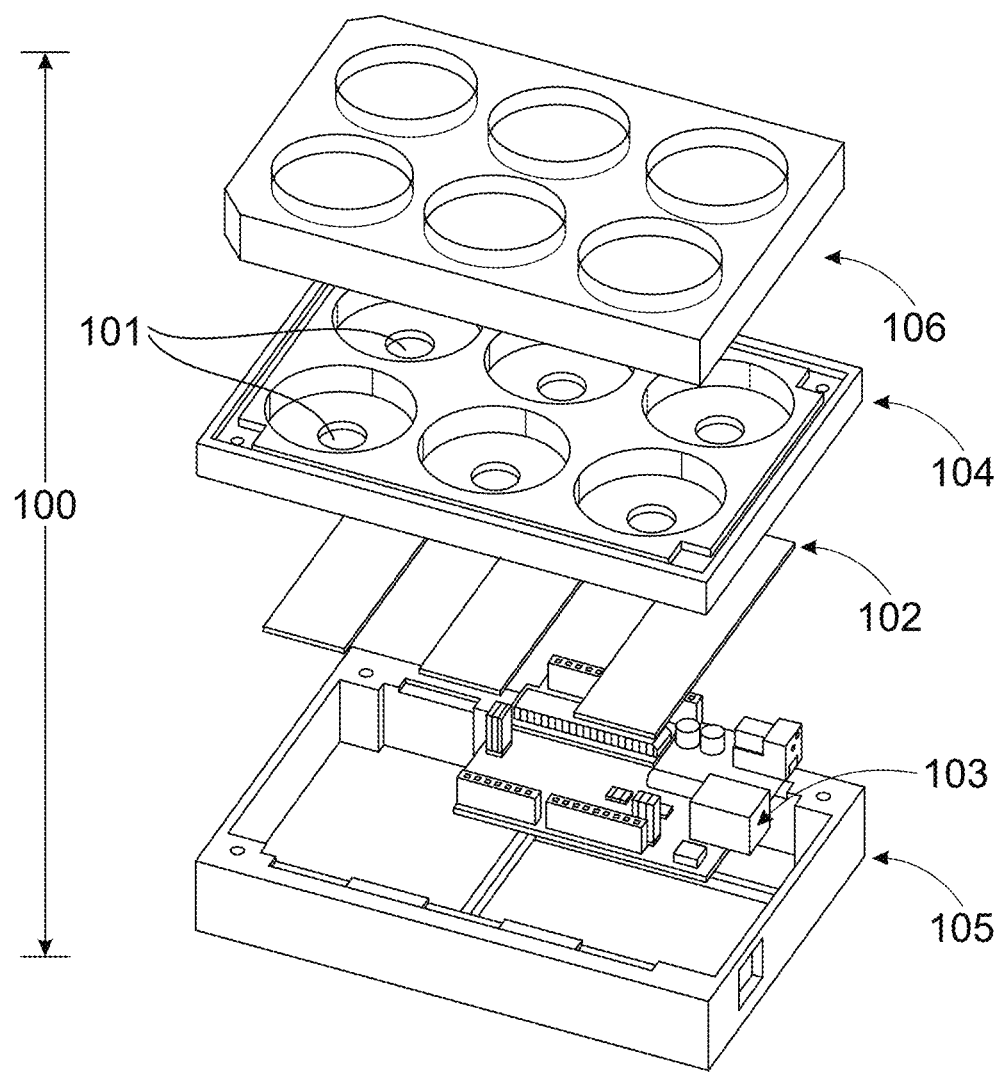
FIG. 16 illustrates a schematic diagram of a general embodiment of the illumination system 100 of the present invention. The illumination system 100 is adapted to illuminate cells, an in particular, transformed PSCs with the vectors of the present invention, to stimulate the FGF pathway and maintain the cells as pluripotent. The illumination system 100 comprises, in one embodiment, LED illumination sources 101 which are embedded in the upper enclosure 104 which is shaped to accommodate a cell culture substrate 106 in which the transformed PSCs are maintained. In an embodiment, the LEDs are individually connected to a printed circuit board 102 which is connected to a microcontroller 103 placed in the lower enclosure 105 and can be fastened together with fasteners.

Referring now to FIG. 16, in general, the cell culture illumination system 100 is designed in such a way that it is easily implemented, for example for use with standard size cell culture plates. The illumination system comprises one or more illumination sources 101 of any type which are capable of irradiating light of a tunable frequency into each well, and to the cells contained within each well of a cell culture plate 106. In some embodiments the illumination source is one or more tunable LEDs. The illumination sources are connected electronically to at least one circuit board 102 and are arranged inside an upper enclosure 104 which is designed to accept the cell culture plate. The circuit board 102 is connected electronically to a microcontroller 103 which controls the light frequency and intensity. The microcontroller 103 and upper enclosure 104 are designed to fit into a lower enclosure 105 and can be held together with fasteners such as screws. The microcontroller 103 is coupled to a power source 107 (see FIG. 17) such as a USB port from a computer. Other power sources could also be used, including for example, wired to a common power outlet or that can be re-chargeable such as a battery.

Figure 17:
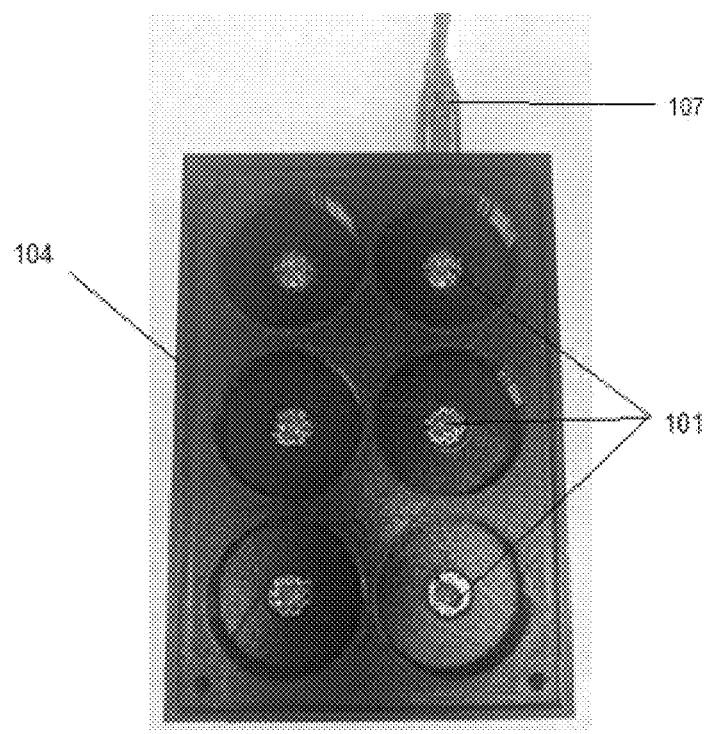
FIG. 17 illustrates a schematic diagram of an embodiment of the circuit board 102 and microcontroller 103 controlling the illumination sources 101 of the present illumination system.
Figure 18:
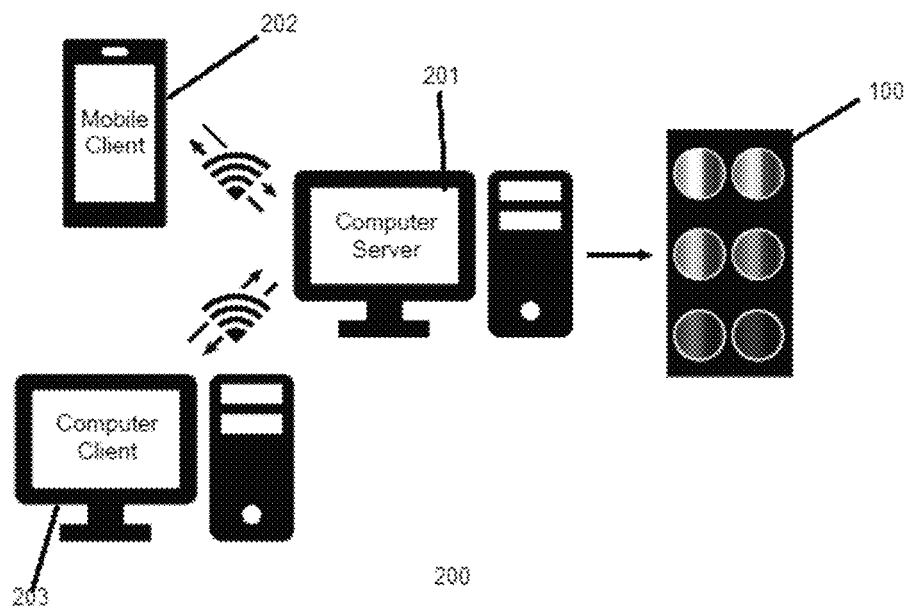
FIG. 18 illustrates a schematic diagram of an embodiment of the fibroblast growth factor free pluripotent stem cell culture system 200. The stem cell culture system 200 comprises at least one illumination device 100 which is connected to a computer server 201 which controls the illumination parameters of the illumination sources 101 of the device 100 via wireless or wired connection to either a mobile client computer 202 or client computer 203 with additional control software.

As shown in FIGS. 16-18, the microcontroller 103 is connected either by wire or wirelessly to a main computer server 200. The main computer server 200 can be programmed with information related to the illumination frequency, intensity and duration.

It should be noted that the microcontroller 103 and the main computer server 200 can all include a computing device such as a microprocessor, hard drive, solid state drive, smartphone or any other suitable computing device known to or conceivable by one of skill in the art. As shown in FIG. 18, the main computer server 200 can be controlled by a computing client device 203, or a smartphone or mobile computing device 202 which is programmed with a non-transitory computer readable medium that is programmed with steps to execute the different illumination frequencies, intensities, and durations of irradiation.

Any such computer application will be fixed on a non-transitory computer readable medium. It should be noted that the computer application is programmed onto a non-transitory computer readable medium that can be read and executed by any of the computing devices mentioned in this application. The non-transitory computer readable medium can take any suitable form known to one of skill in the art. The non-transitory computer readable medium is understood to be any article of manufacture readable by a computer or smartphone. Such non-transitory computer readable media includes, but is not limited to, magnetic media, such as floppy disk, flexible disk, hard, disk, reel-to-reel tape, cartridge tape, cassette tapes or cards, optical media such as CD-ROM, DVD, blu-ray, writable compact discs, magneto-optical media in disc, tape, or card form, and paper media such as punch cards or paper tape. Alternately, the program for executing the method and algorithms of the present invention can reside on a remote server or other networked device. Any databases associated with the present invention can be housed on a central computing device, server(s), in cloud storage, or any other suitable means known to or conceivable by one of skill in the art. All of the information associated with the application is transmitted either wired or wirelessly over a network, via the internet, cellular telephone network, or any other suitable data transmission means known to or conceivable by one of skill in the art.

In accordance with an embodiment, the present invention provides a method for maintaining a pluripotent stem cell line in culture comprising: a) a plurality of pluripotent stem cells in a fibroblast growth factor free culture medium, wherein said are transformed with the expression vectors described herein; b) said transformed cells are maintained in the cell culture system as described herein; and c) periodically irradiating the cells of b) at a wavelength of about 470 nm for a sufficient time and intensity such that the cells maintain their pluripotent capability.

In some exemplary embodiments the intensity at the maximal output in each well of a 6-well plate was between 1 and 23 µW/mm$^2$, with the ability to vary the intensity from 2, 3, 4, 5, 10, 15, 20 or greater µW/mm$^2$. The LEDs can be illuminated for different lengths of time (for example, but without limitation, 0 to 10 min at 1 µW/mm$^2$) and intensity (for example, but without limitation, 0 to 1 µW/mm$^2$ for 5 min). For the long term maintenance of Opto-FGFR hPSCs, the blue light illumination can be repeated 1 min, 5 min, or 10 min or longer in every 1-10 hours, preferably about 2 hours at 1 µW/mm$^2$ during cell culture.

The present inventive approaches defined herein for the optical maintenance of human and porcine PSCs provides new insights for an alternative synthetic approach for the next generation in stem cell research. Furthermore, considering the number of signaling pathways that are crucial for controlling cell specification processes, the opto-FGFR PSCs of the present invention are a proof-of-concept for the optical control over a plethora of mammalian stem cell fates.

The following examples have been included to provide guidance to one of ordinary skill in the art for practicing representative embodiments of the presently disclosed subject matter. In light of the present disclosure and the general level of skill in the art, those of skill can appreciate that the following examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Materials and Methods

Pluripotent cell line culture. The human embryonic stem cells (H9, WiCell) and human induced pluripotent stem cells (induced from GM00024C, fibroblasts from Coriell) were cultured using standard protocols [26]. The hESCs and hiPSCs were cultured on mouse embryonic fibroblasts (MEFs, Applied StemCell) and pre-plated at 12,000 to 15,000 cells/cm2. The medium contained DMEM/F12, 20% knockout serum replacement, 1 mM L-glutamine, 100 µM MEM non-essential amino acids, and 0.1 mM β-mercaptoethanol (Life Technologies). Ten ng/mL of FGF2 (R&D Systems) was added after sterile filtration, and the cells were fed daily and passaged weekly using either 6 U/mL Dispase (Life Technologies) or mechanical means. For feeder-free culture conditions, hPSCs were cultured onto recombinant human Laminin 521 (Life Technologies)-coated plates with StemFit® Basic02 medium (Ajinomoto). The porcine induced pluripotent stem cells (induced from P350-05; PCASMC, porcine coronary artery smooth muscle cells from Sigma-Aldrich) were cultured with mitotically inactivated MEFs in the PSC medium, and the cells were fed daily and passaged weekly using either 6 U/mL Dispase or mechanical means. For routine cell culture, all experiments including passaging were performed in a dark culture room with safelight that does not affect LOV photodimerization.

Plasmid construct. To establish the Opto-FGFR hESC and hiPSC lines, the EGFP region of the AAV-CAGGS-EGFP vector (Addgene plasmid #22212) was replaced by a region of the opto-FGFR1 domain. The PHR domain from the cytoplasmic FGFR1-Cry2 PHR-mCitrine vector and the LOV domain from the mFGFR1-LOV vector (Addgene plasmid #58745) were used for the construction of AAV-opto-FGFR. AAV-opto-FGFRs were then used to establish the opto-FGFR targeted to the AAVS1 region. Two guide RNAs (gRNAs) sequences for opto-FGFR knock-in at the pRosa26 region were chosen to target the first intron of pRosa26 and subcloned into gRNA_Cloning Vector (Addgene plasmid #41824) as described previously [27]. The sequences for pRosa26 gRNA constructs were as follows: pRosa26-gRNA #1, 5'-CCTGGCTTAACCTGATTCTT-3' (SEQ ID NO:10); pRosa26-gRNA #91, 50-GTGAGAGT-TATCTGACCGTA-3' (SEQ ID NO:11). All insert sequences were verified by Sanger DNA sequencing (JHU Synthesis & Sequencing Facility).

TABLE 2

Sequences of Primer Used in This Study

| Genes | Forward | Reverse |
| --- | --- | --- |
| DPPA3 | 5'-TTAATCCAACCTACATCCCAGGG-3' (SEQ ID NO: 12) | 5'-AGGGGAAACAGATTCGCTACTA-3' (SEQ ID NO: 13) |
| ESG1 | 5'-ATATCCCGCCGTGGGTGAAAGTTC-3 (SEQ ID NO: 14) | 5'-ACTCAGCCATGGACTGGAGCATCC-3' (SEQ ID NO: 15) |

TABLE 2-continued

Sequences of Primer Used in This Study

| Genes | Forward | Reverse |
|---|---|---|
| FOXA2 | 5'-CGACTGGAGCAGCTACTATGC-3' (SEQ ID NO: 16) | 5'-TACGTGTTCATGCCGTTCAT-3' (SEQ ID NO: 17) |
| GAPDH | 5'-CGAGATCCCTCCAAAATCAA-3' (SEQ ID NO: 18) | 5'-TTCTAGACGGCAGGTCAGGT-3' (SEQ ID NO: 19) |
| KLF4 | 5'-TCCCATCTTTCTCCACGTTC-3' (SEQ ID NO: 20) | 5'-GGATCGGATAGGTGAAGCTG-3' (SEQ ID NO: 21) |
| MSGN1 | 5'-AGCGAAGGCTGCAGTGTC-3' (SEQ ID NO: 22) | 5'-TGGCCTCTCTGGCTGTAGAC-3' (SEQ ID NO: 23) |
| NANOG | 5'-CATGAGTGTGGATCCAGCTTG-3' (SEQ ID NO: 24) | 5'-CCTGAATAAGCAGATCCATGG-3' (SEQ ID NO: 25) |
| OCT4 | 5'-AGTGAGAGGCAACCTGGAGA-3' (SEQ ID NO: 26) | 5'-ACACTCGGACCACATCCTTC-3' (SEQ ID NO: 27) |
| REX1 | 5'-CAGATCCTAAACAGCTCGCAGAAT-3' (SEQ ID NO: 28) | 5'-GCGTACGCAAATTAAAGTCCAGA-3' (SEQ ID NO: 29) |
| PAX6 | 5'-CTTTGCTTGGGAAATCCGAG-3' (SEQ ID NO: 30) | 5'-AGCCAGGTTGCGAAGAACTC-3' (SEQ ID NO: 31) |
| SOX1 | 5'-CCTCGGATCTCTGGTCAAGT-3' (SEQ ID NO: 32) | 5'-GCAGGTACATGCTGATCATCTC-3' (SEQ ID NO: 33) |
| SOX2 | 5'-GGGAAATGGGAGGGGTGCAAAAGAGG-3' (SEQ ID NO: 34) | 5'-TTGCGTGAGTGTGGATGGGATTGGTG-3' (SEQ ID NO: 35) |
| SOX17 | 5'-CGCACGGAATTTGAACAGTA-3' (SEQ ID NO: 36) | 5'-GGATCAGGGACCTGTCACAC-3' (SEQ ID NO: 37) |
| TBX6 | 5'-AAGTACCAACCCCGCATACA-3' (SEQ ID NO: 38) | 5'-TAGGCTGTCACGGAGATGAA-3' (SEQ ID NO: 39) |
| pGapdh | 5'-CTCAACGGGAAGCTCACTG-3' (SEQ ID NO: 40) | 5'-CCCTGTTGCTGTAGCCAAAT-3' (SEQ ID NO: 41) |
| pGata4 | 5'-GCTTCGCGGGCTCCTACT-3' (SEQ ID NO: 42) | 5'-CCGGTTGATGCCATTCAT-3' (SEQ ID NO: 43) |
| pLin28a | 5'-TGCCGGCATCTGTAAATGGT-3' (SEQ ID NO: 44) | 5'-GCAGTTTGCATTCCTTGGCA-3' (SEQ ID NO: 45) |
| pMsgn1 | 5'-CGCTGGAGTCCTATTCTTCG-3' (SEQ ID NO: 46) | 5'-GTCTGTGAGTTCCCCGATGT-3' (SEQ ID NO: 47) |
| pNanog | 5'-TTGCCCCGAAGCATCCATT-3' (SEQ ID NO: 48) | 5'-CCAGCTCTGATTACCCCACA-3' (SEQ ID NO: 49) |
| pPax6 | 5'-AGTTCTTCGCAACCTGGCTA-3' (SEQ ID NO: 50) | 5'-CATTTGGCCCTTCGATTAGA-3' (SEQ ID NO: 51) |
| pOct4 | 5'-TGAGGCTTTGCAGCTCAGTT-3' (SEQ ID NO: 52) | 5'-ACTGCTTGATCGTTTGCCCT-3' (SEQ ID NO: 53) |
| pSox1 | 5'-CACCCGGATTACAAGTACCG-3' (SEQ ID NO: 54) | 5'-GAGTTGGAGATGGGGCTGTA-3' (SEQ ID NO: 55) |
| pSox2 | 5'-TAAGTACACACTGCCCGGAG-3' (SEQ ID NO: 56) | 5'-CATGGAACCGAGCGTCATGC-3' (SEQ ID NO: 57) |
| pSox17 | 5'-TCGGGGACATGAAGATGAAG-3' (SEQ ID NO: 58) | 5'-GCGGCCGGTACTTGTAGTT-3' (SEQ ID NO: 59) |
| pTbx6 | 5'-AGTATCAGCCCCGCATACAC-3' (SEQ ID NO: 60) | 5'-CTGCTCGGGATCTGACTCTC-3' (SEQ ID NO: 61) |

Gene targeting. The hESC, hiPSC, and piPSC lines were cultured in Rho kinase (ROCK) inhibitor (Calbiochem) for 24 h before nucleofection [28]. The cells were harvested using Accutase® (Innovative Cell Technologies), and 2×106 cells were resuspended in the appropriate reagent (Lonza) with 1 µg Cas9 plasmid (Addgene plasmid #41815), 1 µg guide RNA (Addgene plasmid #41817, for opto-FGFR knock-in at AAVS1 locus; pRosa26-gRNA #1 or #91, for opto-FGFR knock-in at pRosa26 locus), and 1 µg donor plasmid. Nucleofection was performed according to the manufacturer's instructions (Lonza). The cells were subsequently plated on puro-resistant MEFs (Applied StemCell), and puromycin was used for colony selection. The puromycin-resistant colonies were manually picked and expanded.

Blue light illumination. A customized blue light illumination plate (TouchBright W-Series) was designed and manufactured by Live Cell Instrument (Seoul, Korea). This plate contained 42 individual LEDs (70 mW per LED) per well on a 6-well plate. The light intensity was controlled by software (Live Cell Instrument), and the actual light intensity at 470 nm to the cell plate was measured by Laser-Check® (Coherent). The intensity at the maximal output in each well of a 6-well plate was 23 µW/mm2. The LEDs were illuminated for different lengths of time (0-10 min. at 1 µW/mm2) and intensity (0-1 µW/mm2 for 5 min). For the long-term maintenance of Opto-FGFR hPSCs with blue light during the passaging, the blue light illumination was repeated at 1, 5, or 10 min. every 2 h at 1 µW/mm2 during cell culture. The DIY LED illuminating device contained 1 individual LED (60 mW per LED) per well on a 6- or 12-well plate. The maximal output in each well of a 6-well plate was 7 µW/mm2.

Western blot analysis. The phosphorylation status of MEK and ERK1/2 were determined by Western blot analysis. The cells were starved from FGF2 protein for 24 h, and then exposed to either FGF2 protein or blue light illumination. One µg aliquots of whole cell lysates were loaded onto 4-20% gradient SDS-PAGE gels and then transferred to nitrocellulose membranes (Bio-Rad) using the Trans-Blot® Turbo™ Transfer System (Bio-Rad). The detection of phosphorylated ERK1/2 proteins (42 and 44 kDa) was performed using a phospho-ERK1/2 antibody (Cell Signaling), total ERK1/2 expression level was determined using a total phospho-ERK1/2 antibody (Cell Signaling), detection of pMEK protein (45 kDa) was performed using a pMEK1/2 antibody (Cell Signaling), and total MEK expression level was determined using a total MEK1/2 antibody (Cell Signaling). The expression levels are quantified by normalizing to GAPDH expression (Cell Signaling). Following the primary antibody incubation, the membranes were incubated with the appropriate secondary antibodies and subsequently visualized with an ECL kit (Pierce).

Transcriptome analysis. Briefly, total RNA was extracted from cell pellets using TRIzol® Reagent (Life Technologies), and 1 µg of RNA was reverse transcribed using the High Capacity cDNA Reverse Transcription Kit (Applied Biosystems). The qRT-PCR mixtures were prepared with SYBR Green PCR Master Mix (Kapa Biosystem), and the reactions were performed using the Mastercycler ep Realplex2 (Eppendorf). The transcription levels were assessed by normalizing to GAPDH expression. The RNA-seq libraries were constructed using TruSeq Stranded Total RNA RiboZero Gold sample Prep Kit (Illumina) following the manufacturer's protocol. After the sequencing run, the Illumina Real Time Analysis (RTA) module was used to perform image analysis and base calling, and the BCL Converter Software (bcl2fastq v2.17.1.14) was used to generate FASTQ files that contained the sequence reads. The pair-end reads of cDNA sequences were aligned back to the human genome (UCSC hg19 from Illumina iGenome) by the spliced read mapper TopHat (v2.0.9). The sequencing depth is over 90 million (45 million paired-ends) mappable sequencing reads. The alignment statistics and Q/C was achieved by SAMtools (v0.1.18) and RSeQC (v2.3.5) to calculate quality control metrics on the resulting aligned reads; this provides information on the mappability, uniformity of gene body coverage, insert length distributions, and junction annotation. The heatmap from the RNA-seq data was generated followed the manufacturer's instructions (Partek® Genomics Suite®, version 6.6). To create the heatmap, the undifferentiated-experimental and differentiated-control groups were compared to generate the 8132 differentially expressed gene set, which was corrected to a fold change of greater or less than two and a false discovery rate (FDR) with a p value<0.05. Next, a clustering analysis of this heatmap was performed using the hierarchical clustering method with standardized expression normalization (a default process in the Partek® Genomics Suite®, version 6.6). The single-cell qRT-PCR was performed as previously described [29]. Briefly, OCT4::EGFP+ single-cells were isolated by fluorescence-activated cell sorting (FACS) into a 96-well plate containing 10 µg of lysis buffer. These plates were then sealed for single-cell reverse transcription and cDNA amplification using a universal sequence from the adaptor. The final amplified cDNA was used for qRT-PCR.

FACS analysis. The cells were dissociated with Accutase® for flow cytometry and analyzed using BD FACSCalibur™ (Becton Dickinson), and the data was visualized using FlowJo software (Tree Star Inc.).

In vitro differentiation into three germ layers. Opto-FGFR hPSCs cultured with blue light for more than 6 weeks were differentiated into three germ layer lineages following the manufacturer's protocol (STEMdiff™ Trilineage Differentiation Kit, Catalog #05230), and the immunofluorescent staining and RT-PCR for the representative markers of each lineage were performed at the recommended time point.

Directed differentiation of hPSCs. Undifferentiated hPSCs were dissociated into single cells using Accutase® to differentiate into desired cell types. For directed differentiation of hPSC-derived myotubes and hPSC-derived dopaminergic neurons, we followed previously described protocols [26, 30].

Teratoma formation assay. The teratomas were generated by the intramuscular injection of Opto-FGFR hESCs and Opto-FGFR hiPSCs cultured with blue light for more than 8 weeks into NOD SCID mice. In brief, $5 \times 10^6$ cells were harvested and injected into the hindlimb of 6-week-old male NOD SCID mice. Approximately 7 weeks after injection, the tumors were dissected and fixed in 10% formalin (Sigma-Aldrich); the paraffin sections were prepared and stained with hematoxylin/eosin. The differentiated tissues that represent the three embryonic germ layers were identified.

LED illuminating device and software. The LED illuminating device consists of 6 or 12 LED diodes (EDGELEC), a printed circuit board (Elegoo), a microcontroller (Elegoo), and a 3D printed plastic casing. The LEDs were soldered onto the circuit board, which was wired to the microcontroller. The plastic casing was designed using computer-aided design software (AutoCAD) and printed with a 3D plastic printer (Monoprice 3D Select) using polylactic acid plastic (HATCHBOX). The casing was secured together using metal screws (Snug Fastener). The components for the LED illuminating device should be accurately printed and assembled to fix the distance between the cells and the light, among the devices. The software to control the LED illuminating device and the mobile application were developed in Processing 3.5.3.

Statistical analysis. All statistical analyses were performed using Prism 6 (GraphPad). The values were the results of at least three independent experiments, with multiple replicates of each, and reported as the mean±SEM. Differences between two samples were analyzed for significance using the unpaired two-tailed Student's t-test in Prism (GraphPad).

Results

Generation of a Novel FGF2-Free Human PSC Culture System

Figure 1C:
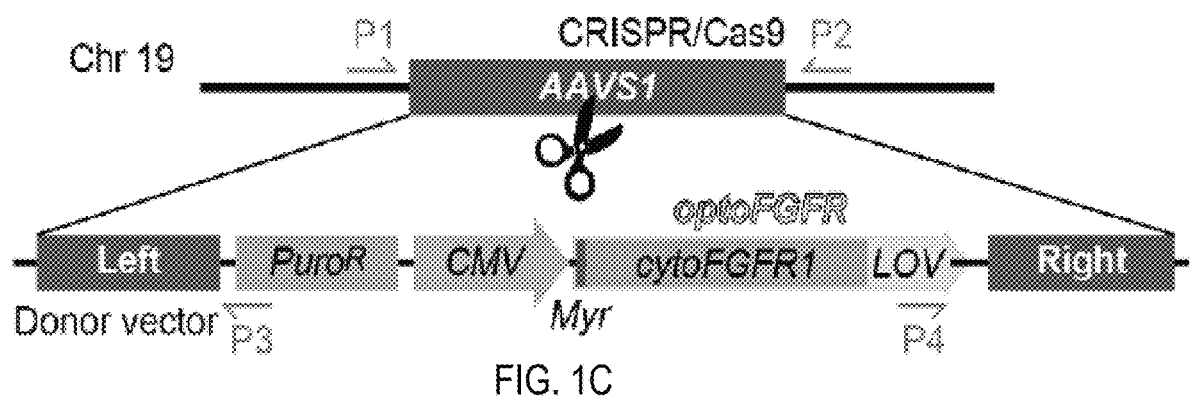
Figure 6A:
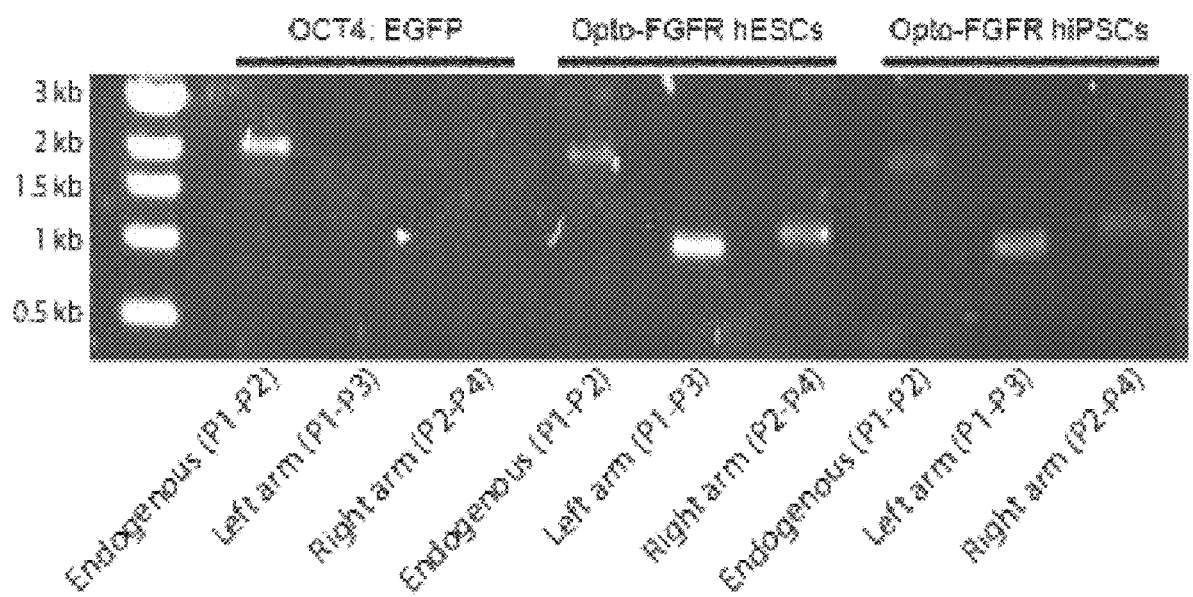
FIG. 6A-6F. The generation of opto-FGFR knock-in hPSCs.
Figure 6B:
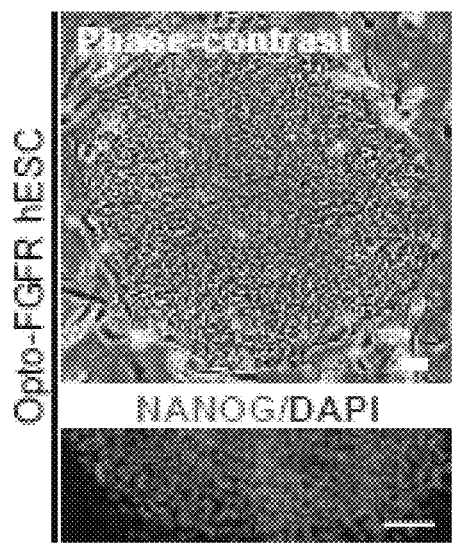
Figure 6C:
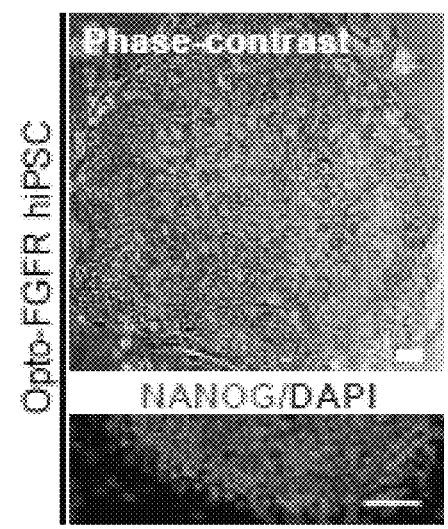
Figure 6D:
Figure 6E:
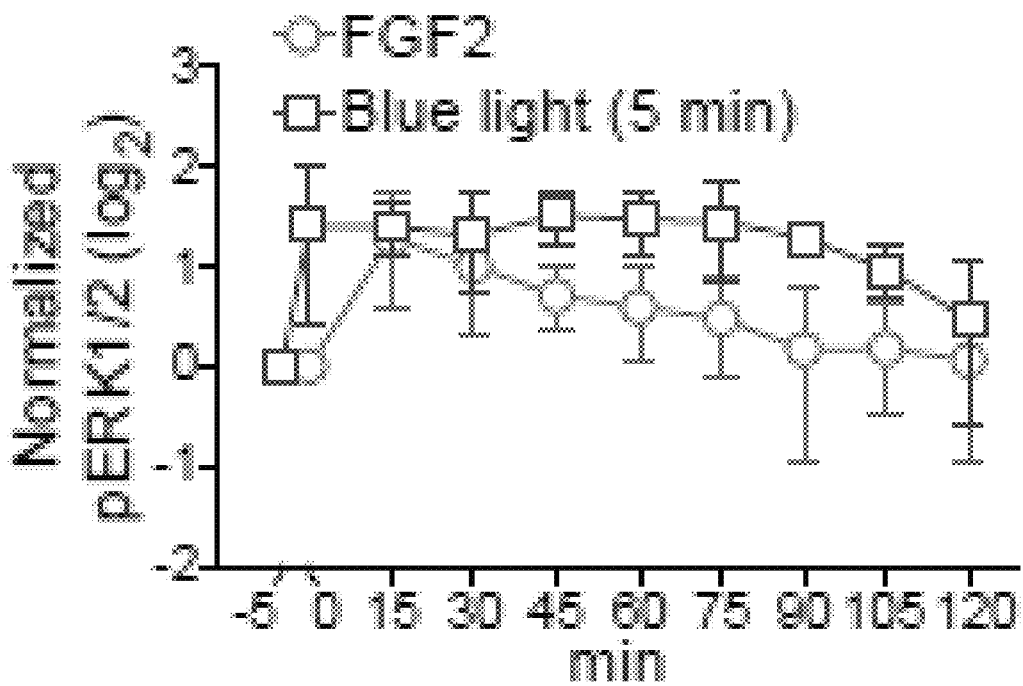
Figure 6F:
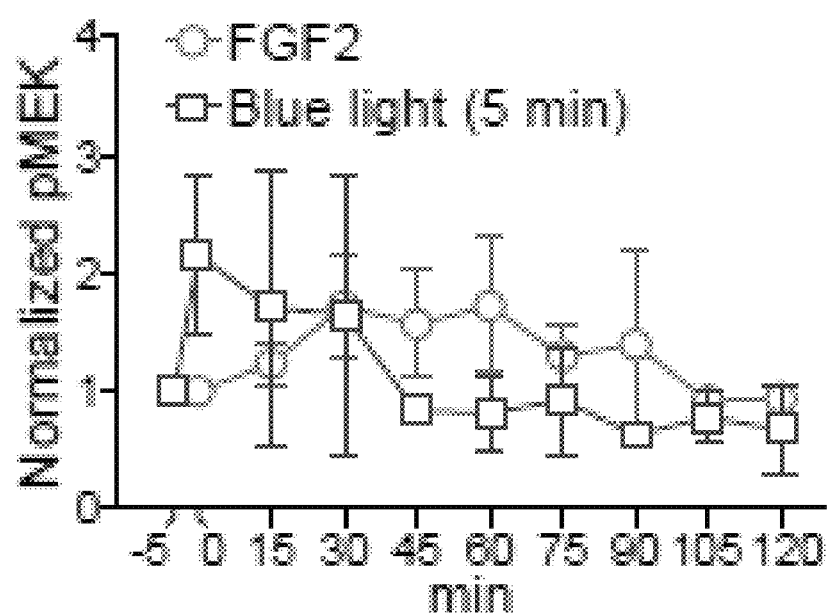

Generation of a light-inducible FGF signaling system. To create a light-inducible FGF signaling system for maintaining the pluripotency of PSCs, the intracellular domain of FGFR1 was fused with a photoactivatable LOV domain (discovered in *Vaucheria fridida*) and a myristoylation signal peptide (Myr) [31-35] (FIGS. 1A and B). This opto-FGFR cassette was inserted into the AAVS1 safe-harbor locus in OCT4::EGFP human embryonic stem cells (hESCs) [36] and human iPSCs (hiPSCs) using the CRISPR/Cas9 system [27,37] (FIG. 1C and FIG. 6A; Opto-FGFR hESC/hiPSC lines). The isolated Opto-FGFR hESC/hiPSC clones exhibited atypical colony morphology and expressed the pluripotency marker NANOG (FIGS. 6B and 6C). To test the effects of blue light illumination on the established Opto-FGFR hPSCs (FIG. 6D), we compared the phosphorylation levels of ERK1/2 and MEK after treatment with FGF2 protein or blue light (470 nm) illumination because phosphorylation of MEK and ERK1/2 are markers for activation of the FGF signaling pathway in hESCs [12,15]. After 24 h of FGF2 protein starvation, the cells were harvested at 15 min. intervals up to 120 min. following 10 ng/mL of FGF2 supplementation. For the blue light illumination, cells were collected at the same time points following 1 $\mu W/mm^2$ of blue light illumination for 5 min. Western blot analyses demonstrated activated FGF signaling in both conditions (FIGS. 6E and 6F).

Figure 7A:
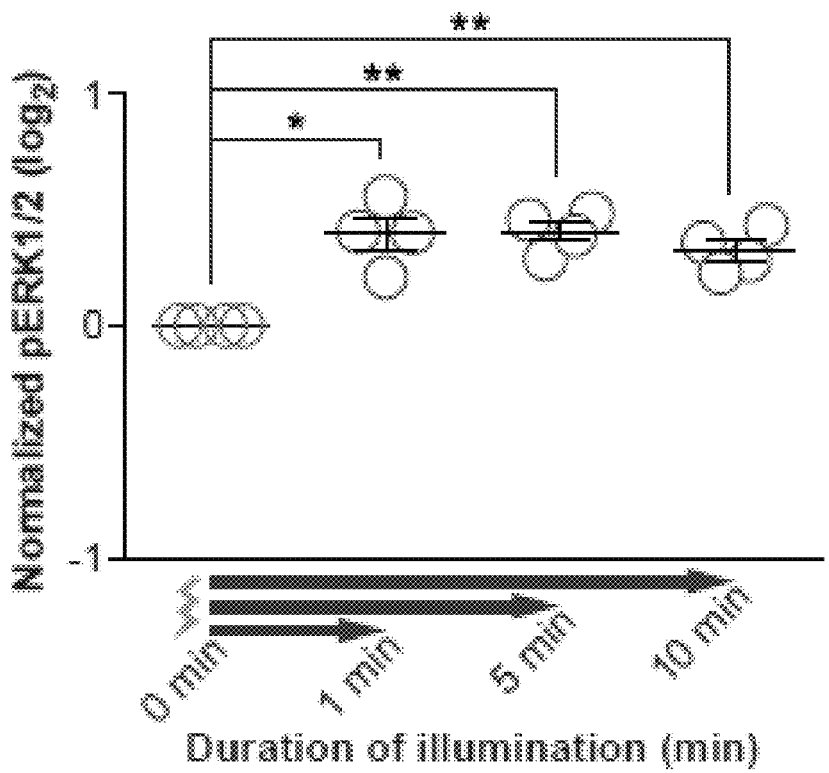
FIG. 7A-7B. Phosphorylation of ERK1/2 in Opto-FGFR hESCs by blue light illumination.
Figure 7B:
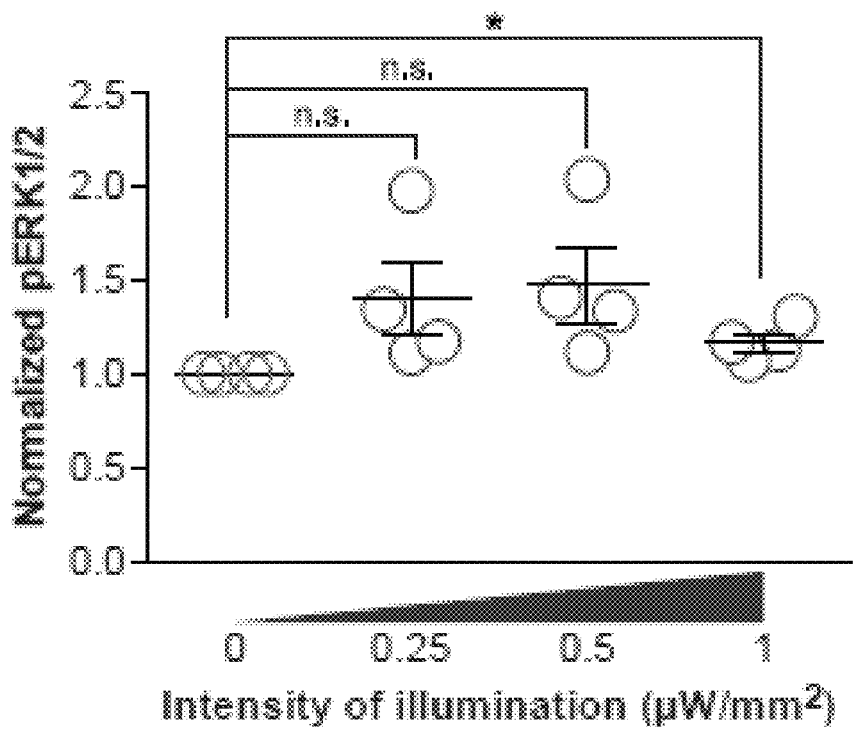
Figure 8A:
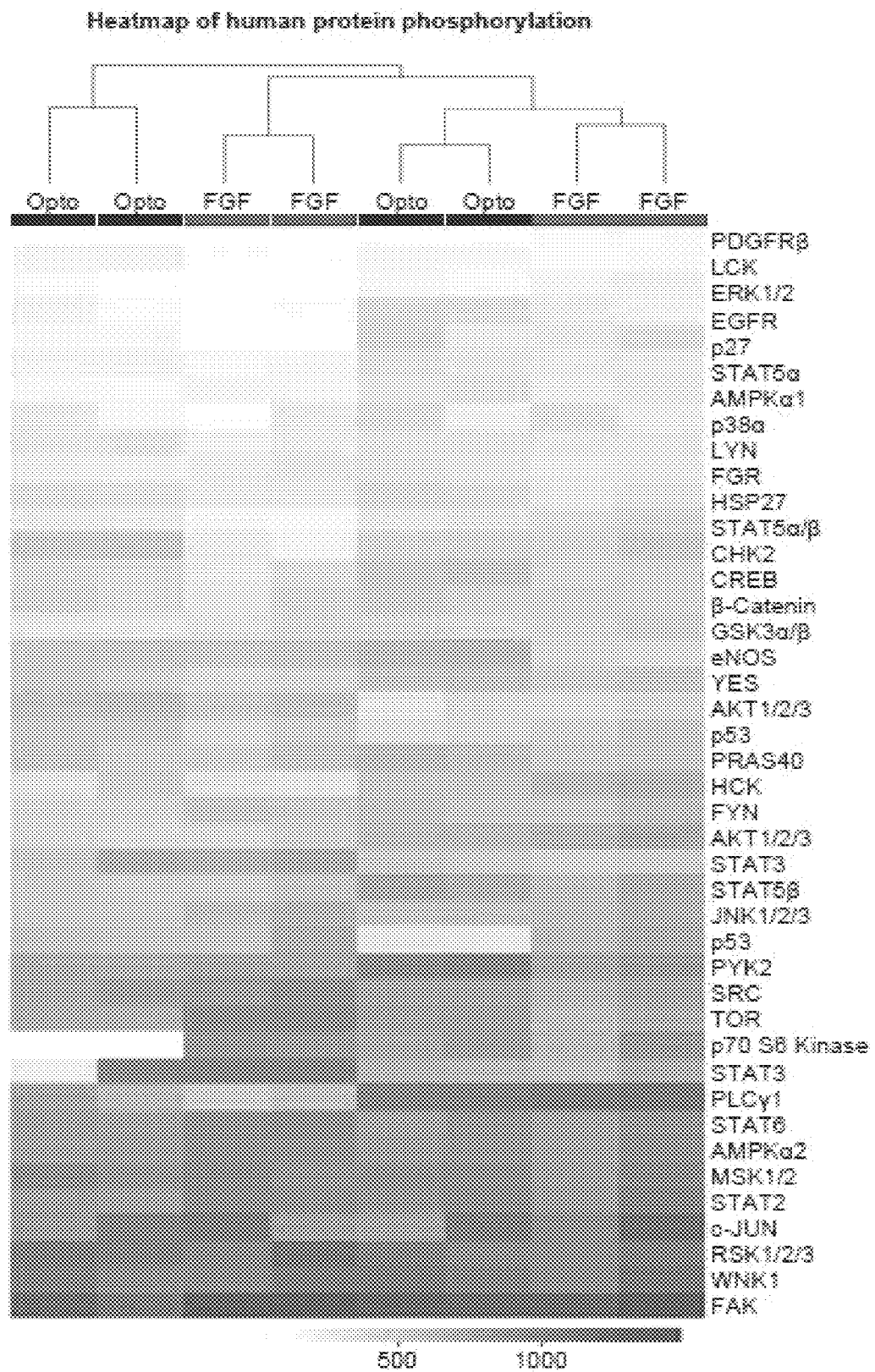
FIG. 8A-8C. Profiles of protein phosphorylation upon activation of the FGF signaling pathway.
Figure 8B:
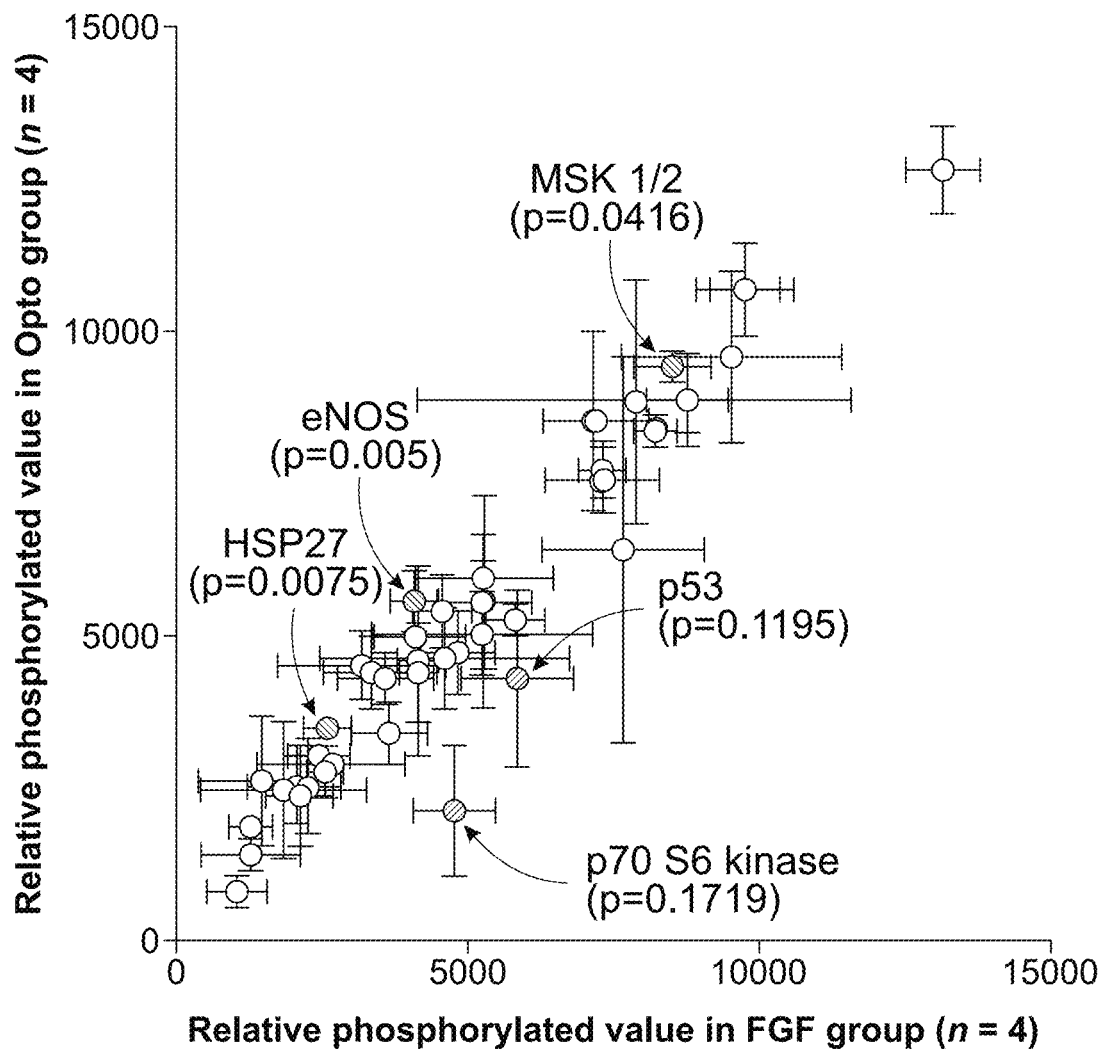
Figure 8C:
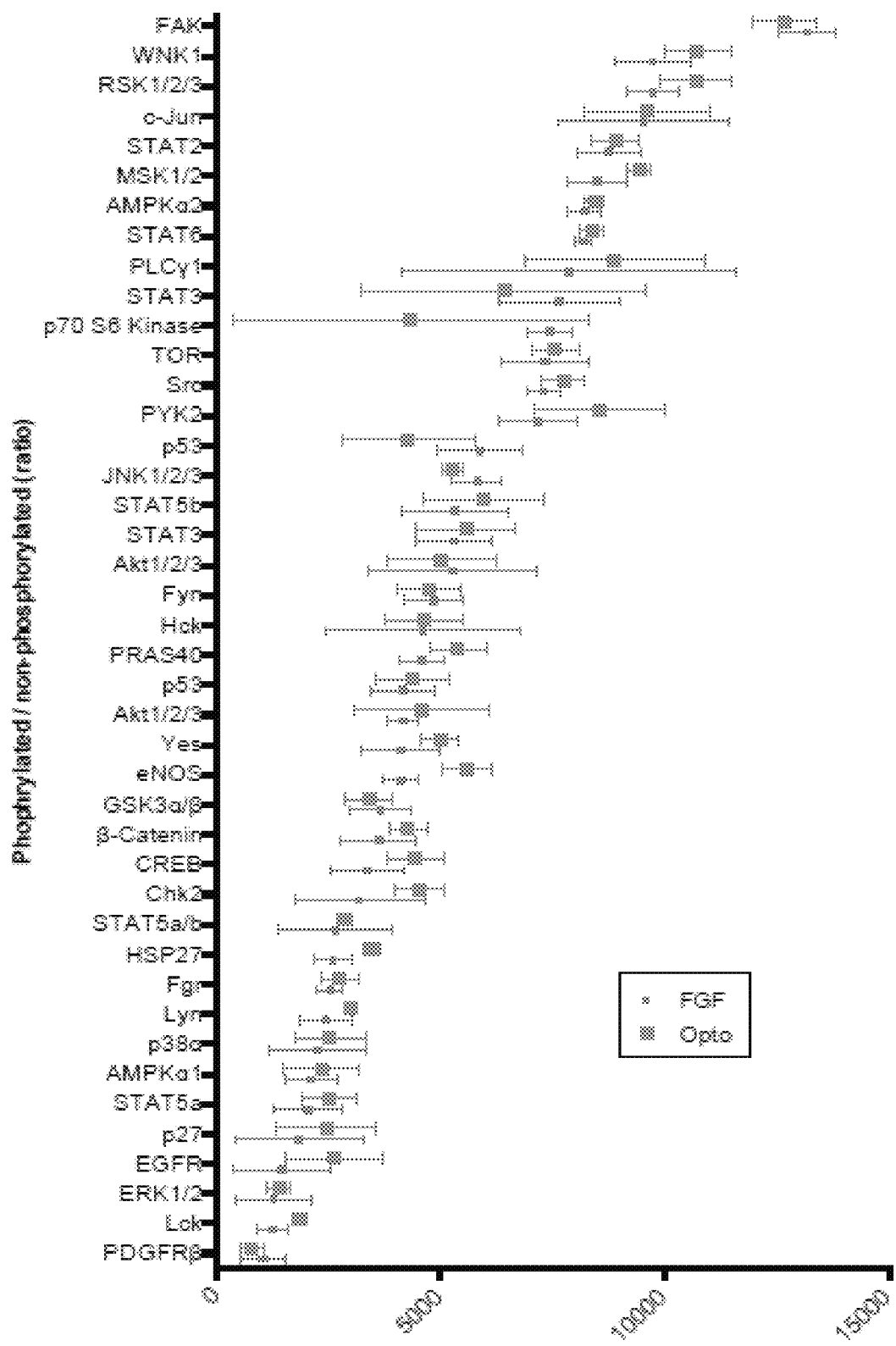
Figure 9A:
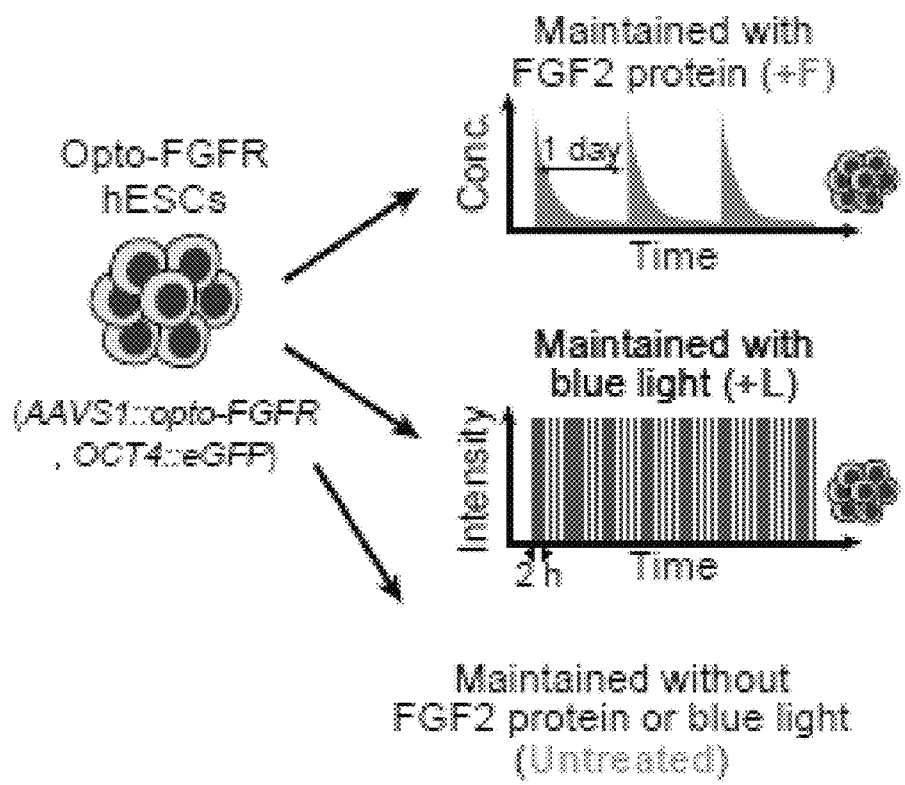
FIG. 9A-9F. Optogenetic activation of FGF signaling is sufficient to maintain pluripotency in hESCs.
Figure 9B:
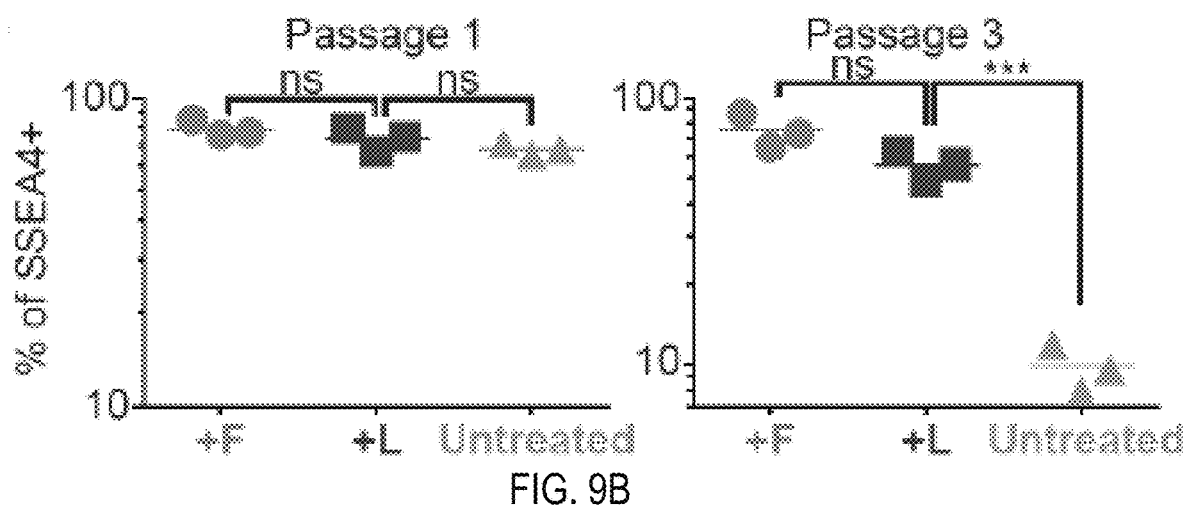
Figure 9C:
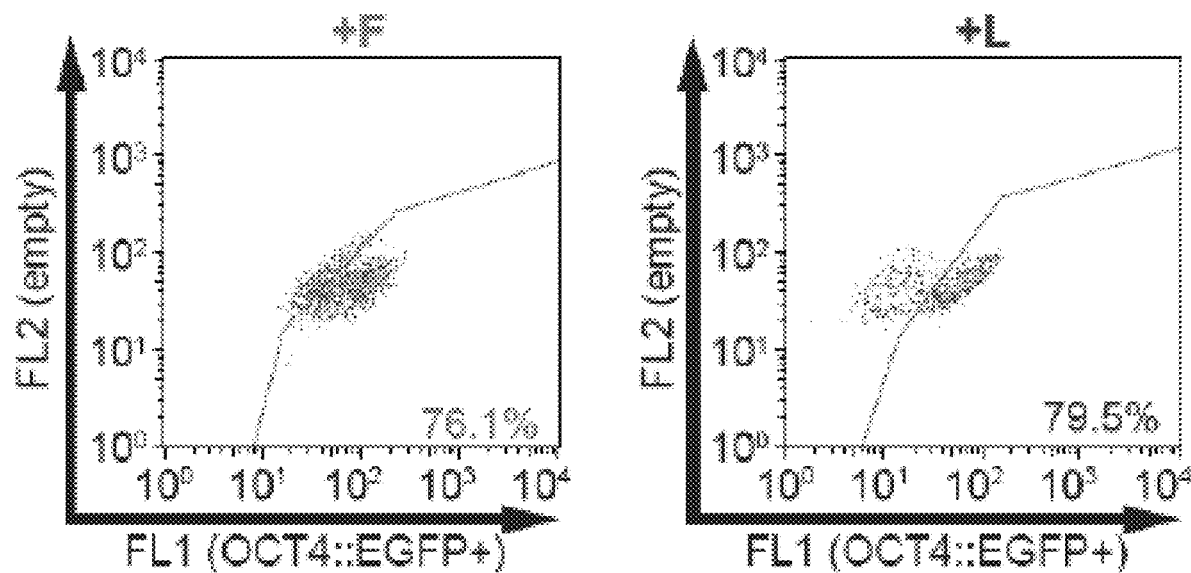
Figure 9D:
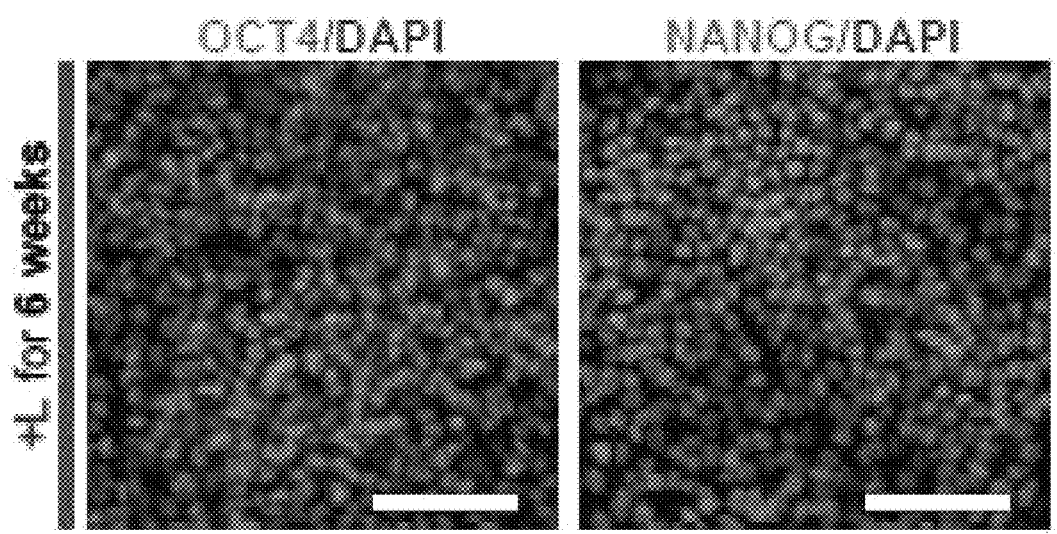
Figure 9E:
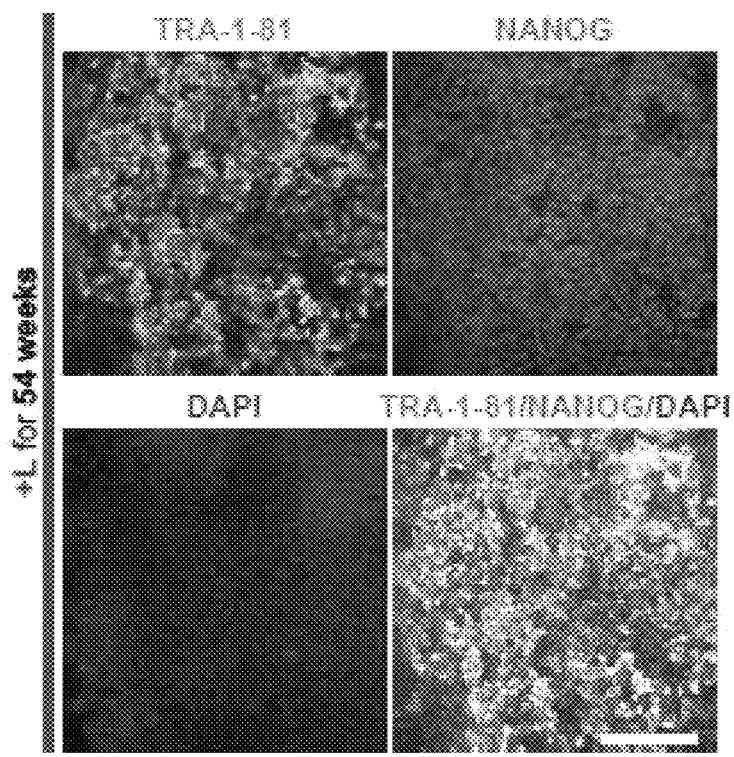
Figure 9F:
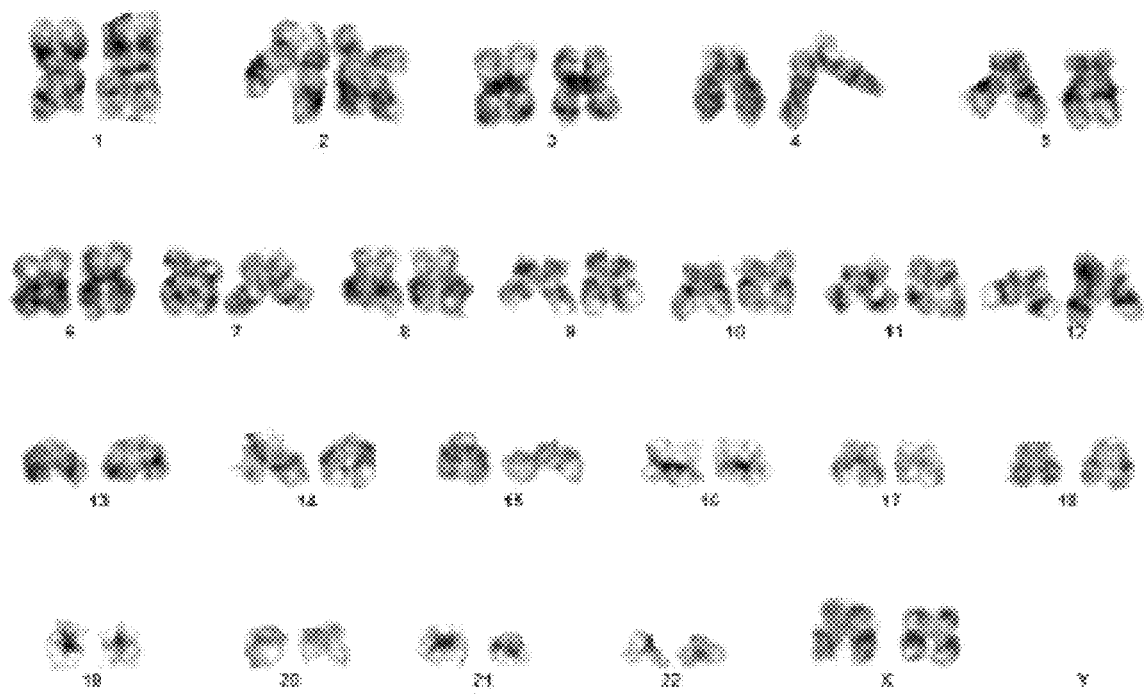

Optimization of the optical induction of FGF signaling. Next, we optimized the light illumination conditions and found that 5 min. of illumination was sufficient to induce FGF signaling, and the blue light exposure resulted in faster activation of FGF signaling than FGF2 supplementation (FIGS. 6E and 6F). The effects of the different exposure times (0-10 min. at 1 $\mu W/mm^2$) and intensities of blue light (0-1 $\mu W/mm^2$ for 5 min) on ERK1/2 phosphorylation were measured, and the results showed the saturation and tunability of blue light in opto-FGFR (FIG. 7). In addition, we found that the blue light illumination-based activation of FGF signaling in Opto-FGFR hESCs showed similar levels of protein phosphorylation in multiple downstream targets as those treated with recombinant FGF2 protein (FIG. 8). These data suggest that the optical induction of FGF signaling via the LOV module has effects comparable to the activation via FGF2 protein supplementation in hPSC culture.

Figure 1D:
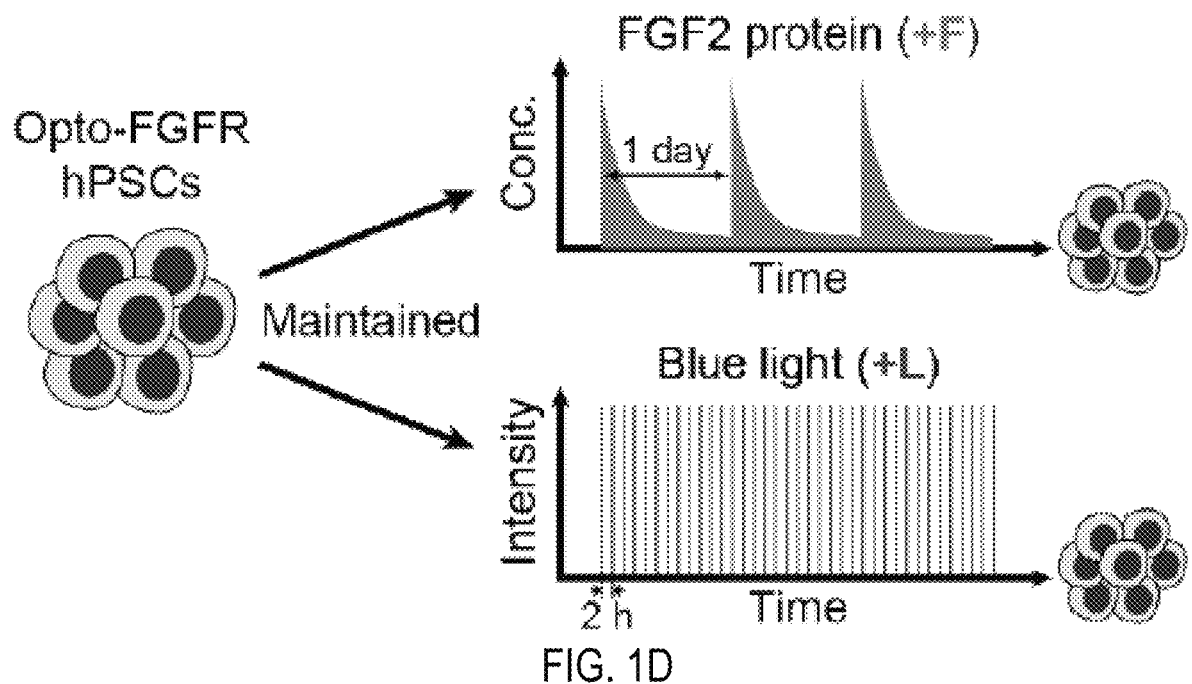
Figure 1E:
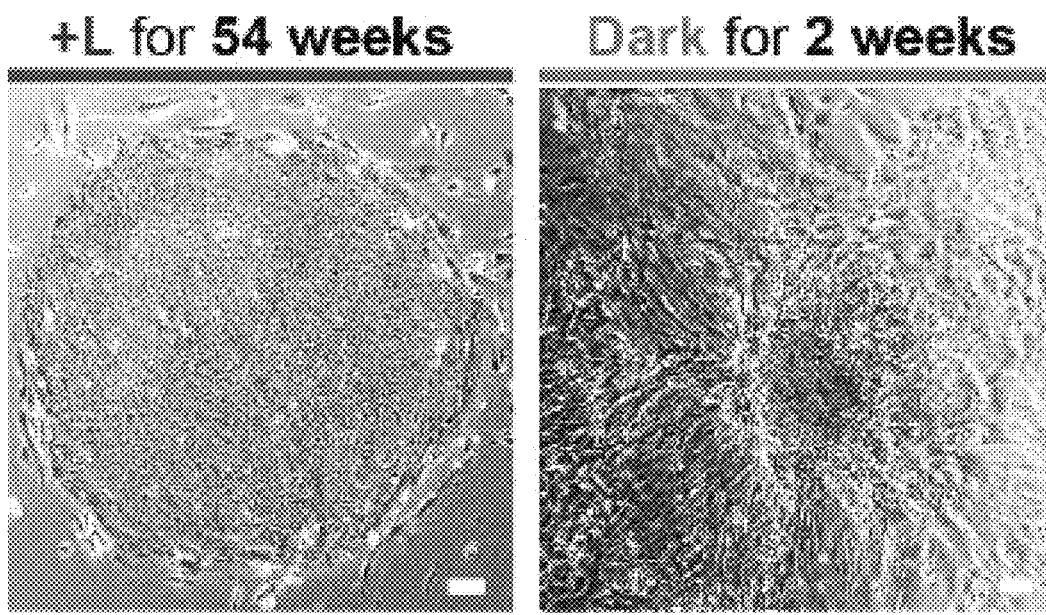
Figure 1F:
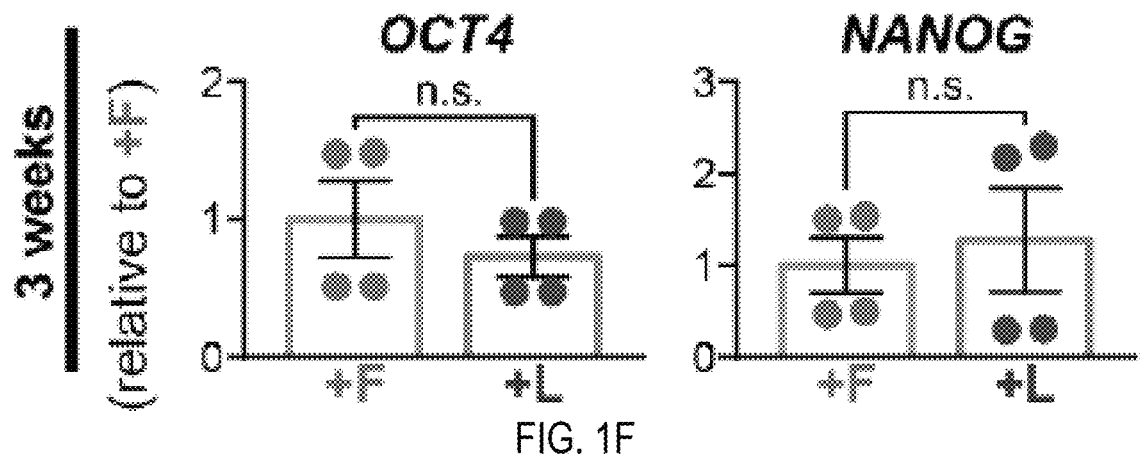
Figure 1G:
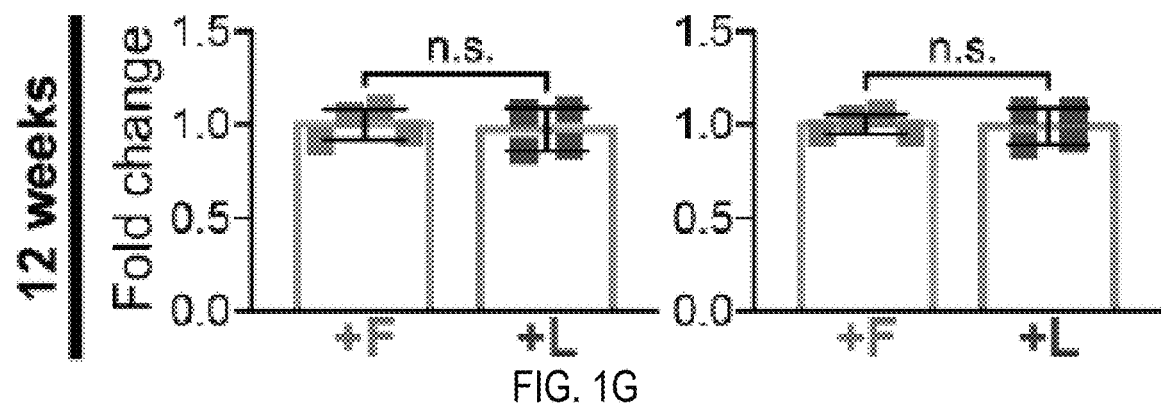
Figure 1H:
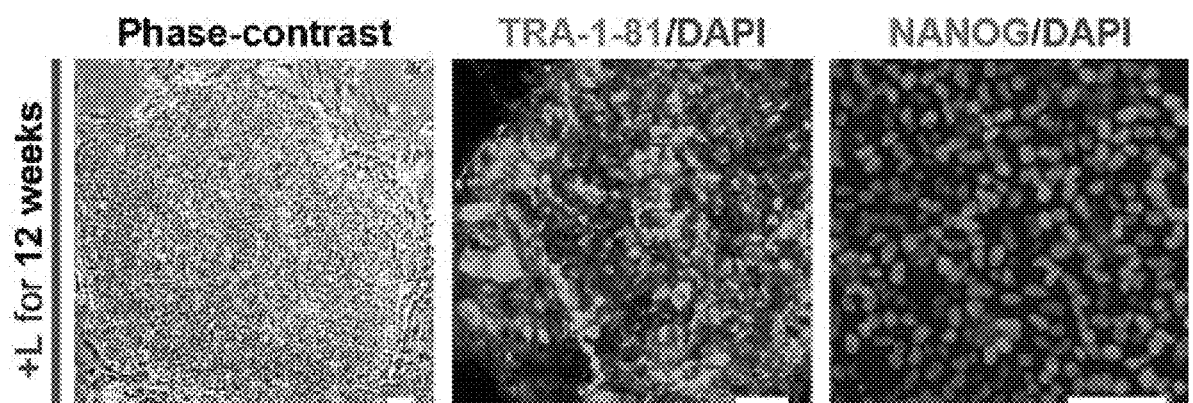
Figure 10A:
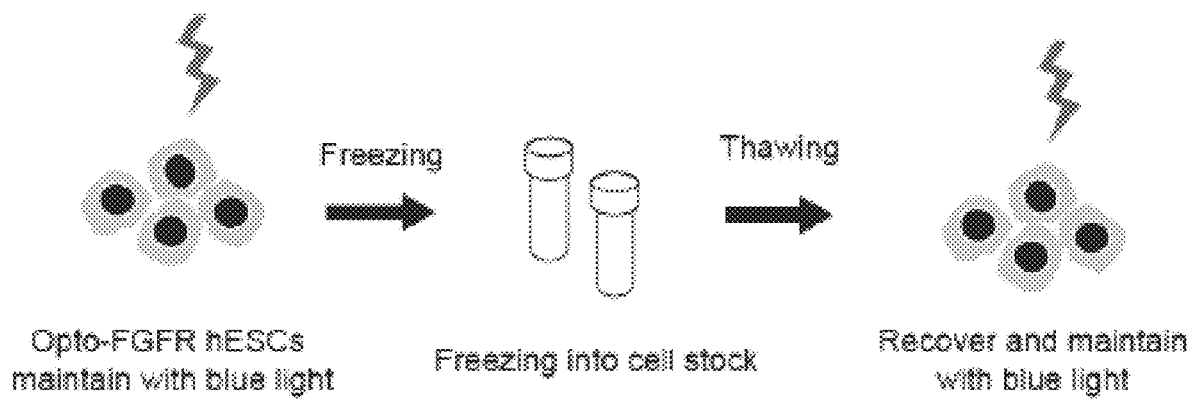
FIG. 10A-10B. The freezing and thawing of Opto-FGFR hESCs cultured with blue light illumination.
Figure 10B:
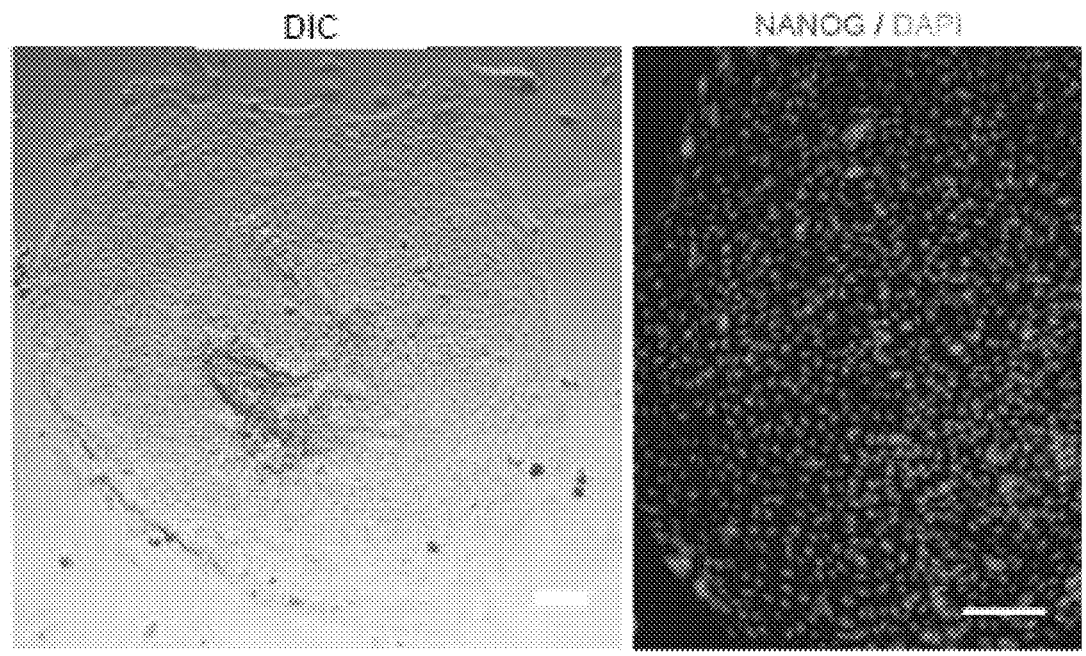
Figure 11A:
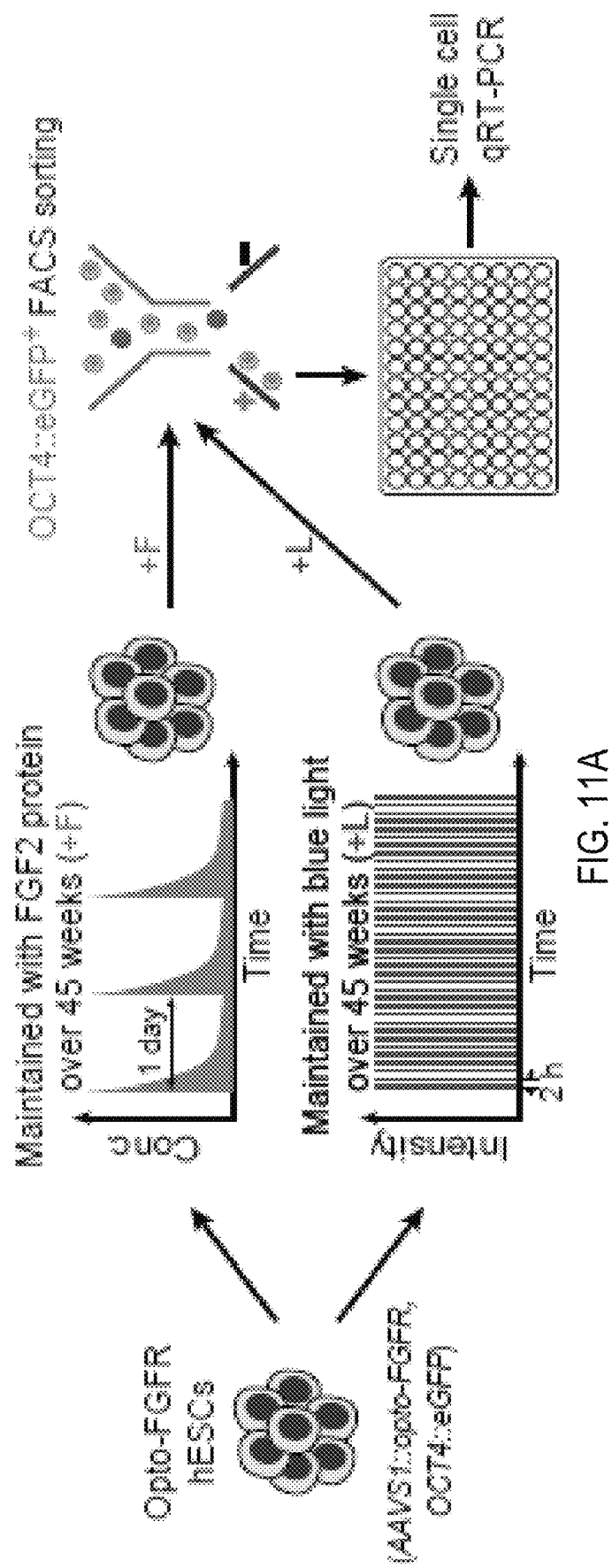
FIG. 11A-11B. Gene expression profiles of pluripotency markers in Opto-FGFR hESCs at a single-cell level.
Figure 11B:
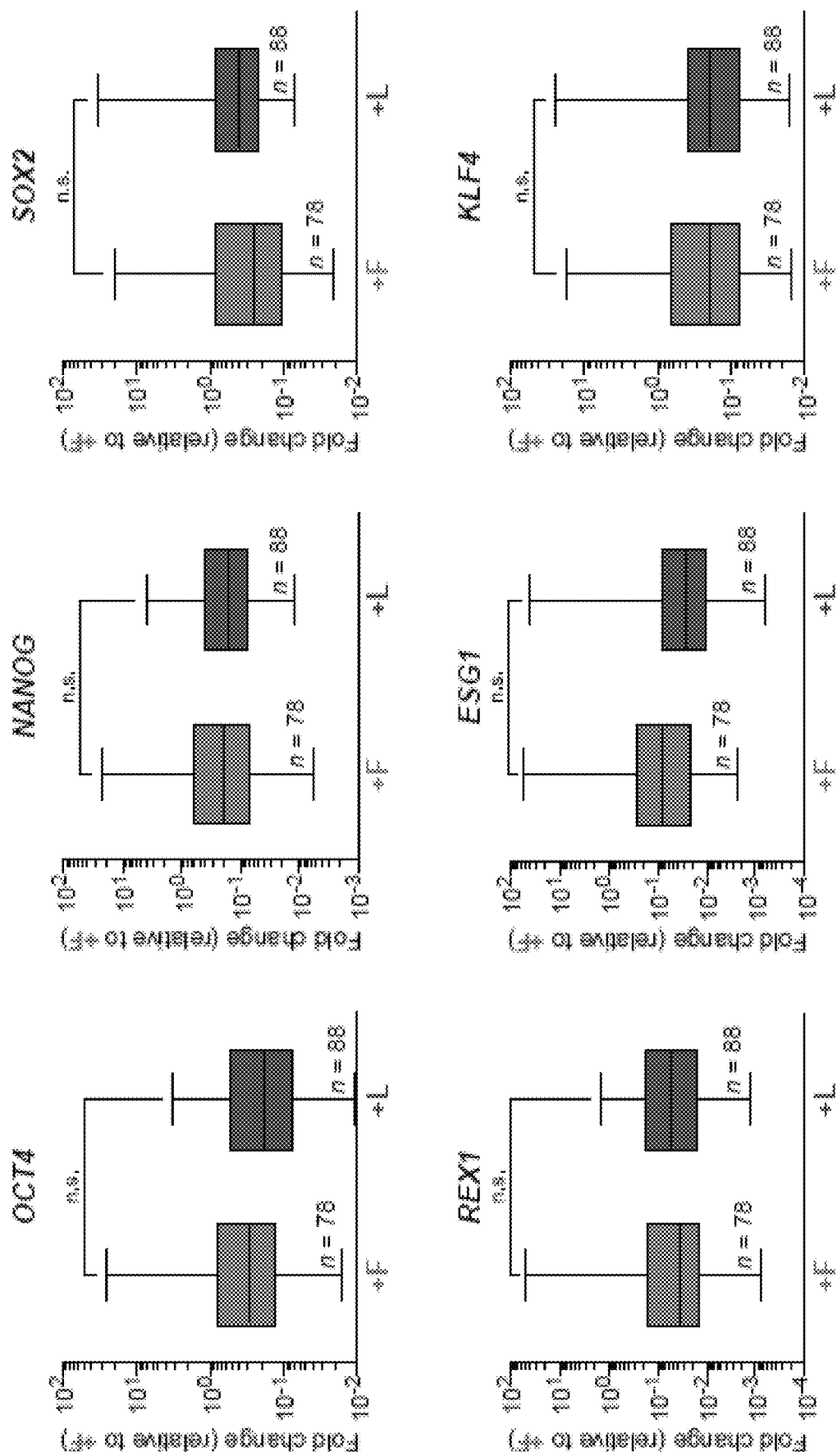

Long-term validation of the light-inducible FGF signaling system. The FGF2 protein is a critical medium component for maintaining the undifferentiated state in hPSCs; however, in the daily feeding condition, its concentration decreased by approximately 40% in 4 h and approximately 10% in 24 h after the initial feeding [38] (FIG. 1D, +F, positive control; FGF2 protein treatment). To repeatedly stimulate the FGF signaling at the appropriate level, we maintained Opto-FGFR hPSCs with a pulsed (not continued) blue light (FIG. 1D, +L, blue light illumination; 1 $\mu W/mm^2$, illumination of blue light for 1 min. or 5 min. in every 2 h). While the Opto-FGFR hESCs cultured in the dark were fully differentiated after 2 weeks, the cells cultured with pulsed blue light maintained hESC-colony morphologies for more than 1 year without FGF2 supplementation (FIG. 1D). The optically maintained hESCs from multiple passages showed a normal karyotype and comparable expression levels of pluripotency markers, including OCT4 and NANOG mRNAs and OCT4, NANOG, and SSEA4 proteins, to that of the cells maintained with FGF2 supplementation (FIGS. 1F and 1G and FIG. 9). Notably, the Opto-FGFR hiPSCs optically maintained for 12 weeks still expressed multiple pluripotency markers, OCT4 and NANOG mRNAs, and TRA-1-81 and NANOG proteins (FIGS. 1G and 1H). Moreover, the Opto-FGFR hESCs maintained with blue light illumination were successfully recovered after a freeze/thaw cycle (FIG. 10). To compare the transcriptional distribution of key pluripotency markers in hPSCs maintained with either pulsed blue light or FGF2 protein in more detail, we further profiled the gene expression of pluripotency markers at a single-cell level. The cells maintained with either condition for over 45 weeks were purified to OCT4::EGFP+ single-cells by cell sorting (FIG. 11A). The expression levels of key pluripotency marker genes, such as OCT4, NANOG, SOX2, REX1, ESG1, and KLF4, in the optically maintained single-PSCs were similar to the levels in the single-PSCs maintained with FGF2 supplementation (FIG. 11B). These data demonstrate that our optical induction system for FGF signaling is a suitable long-term culture system for maintaining the pluripotency of hPSCs.

Figure 2A:
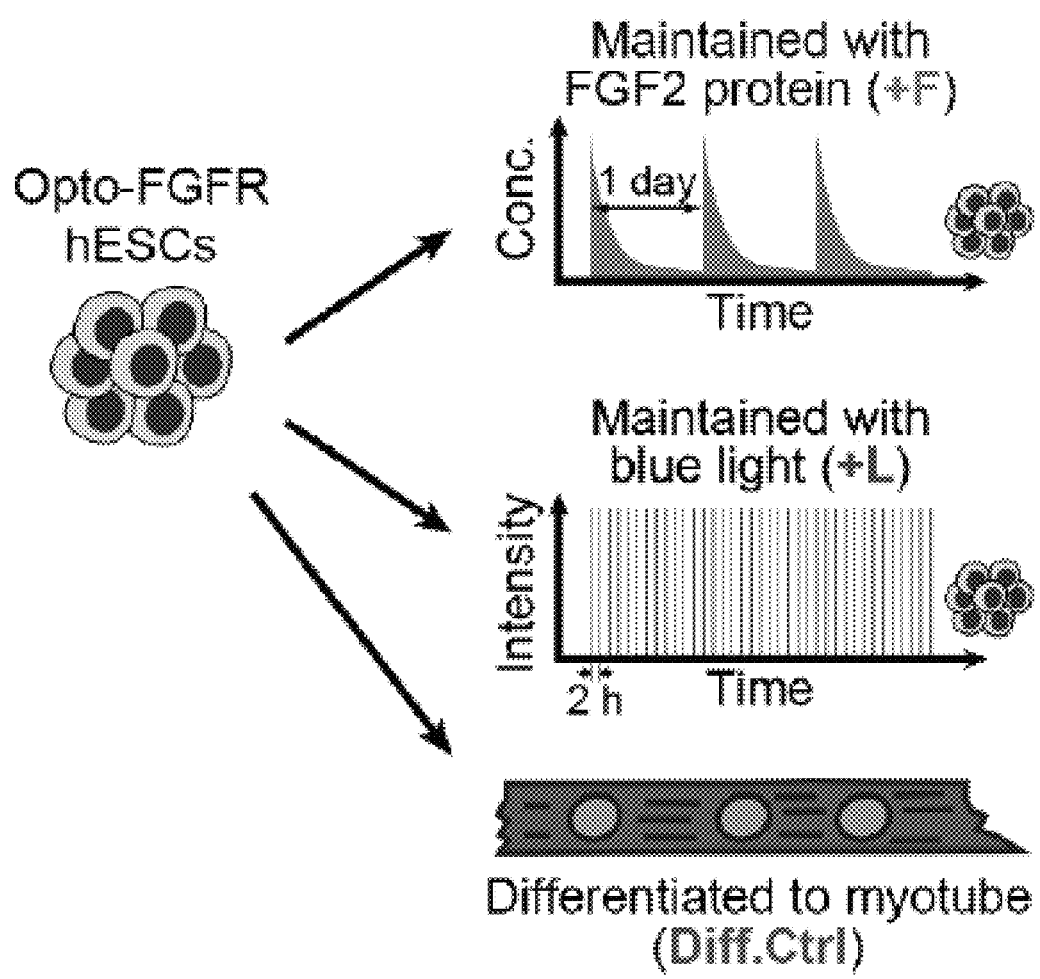
FIG. 2A-2F. The maintenance of pluripotency of Opto-FGFR hESCs cultured with blue light illumination.
Figure 2B:
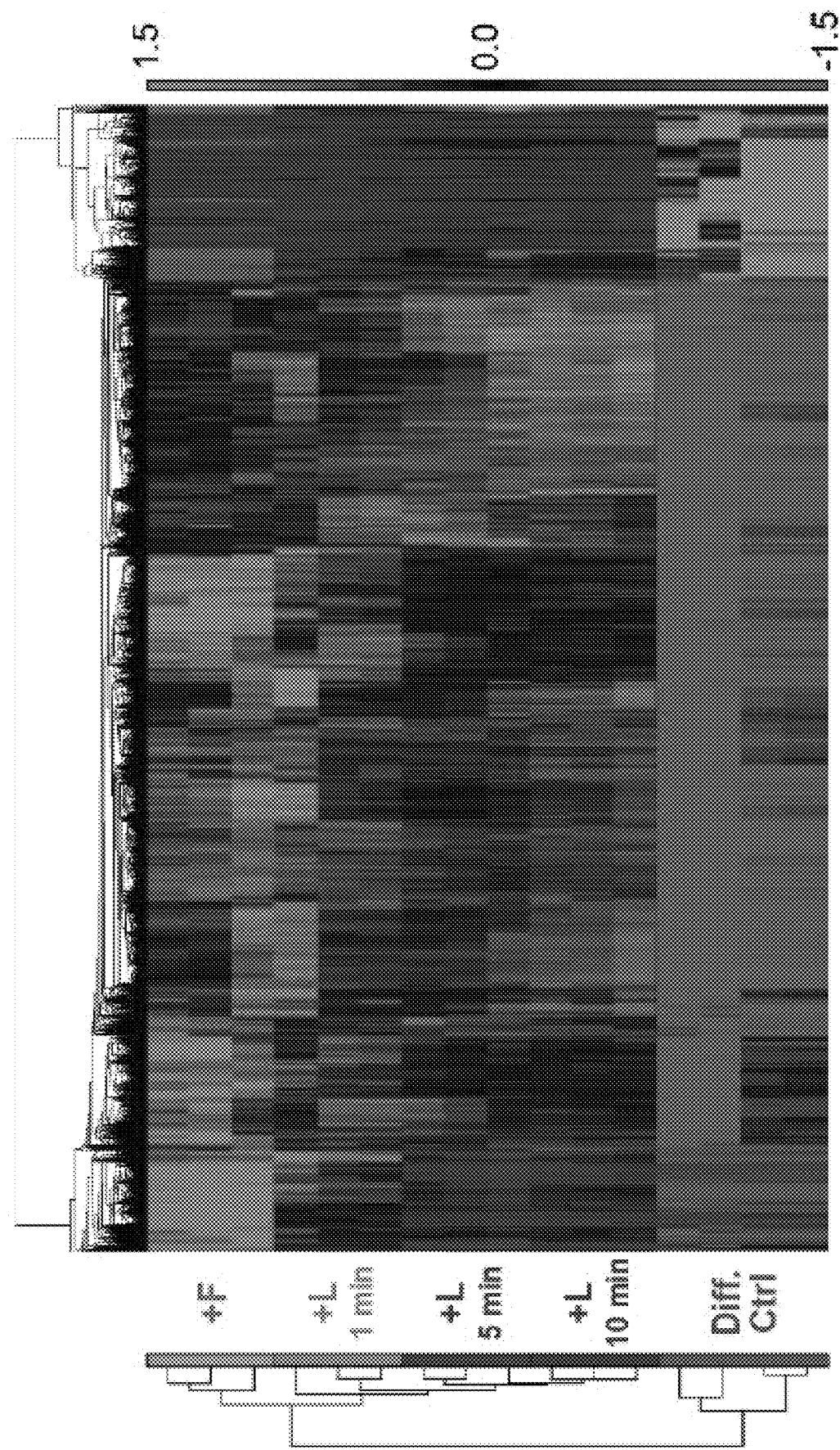
Figure 2C:
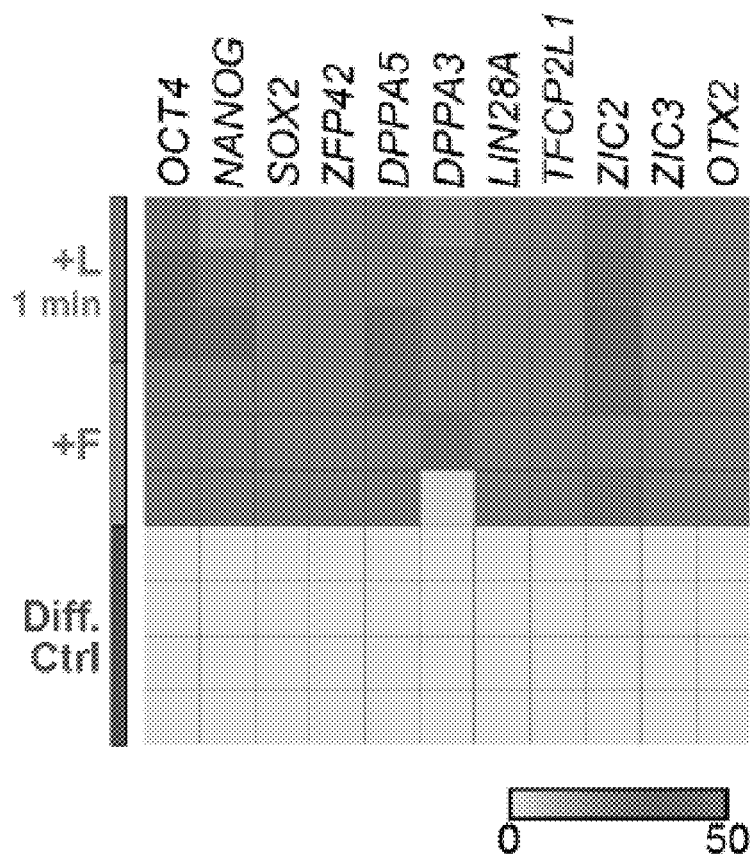
Figure 2D:
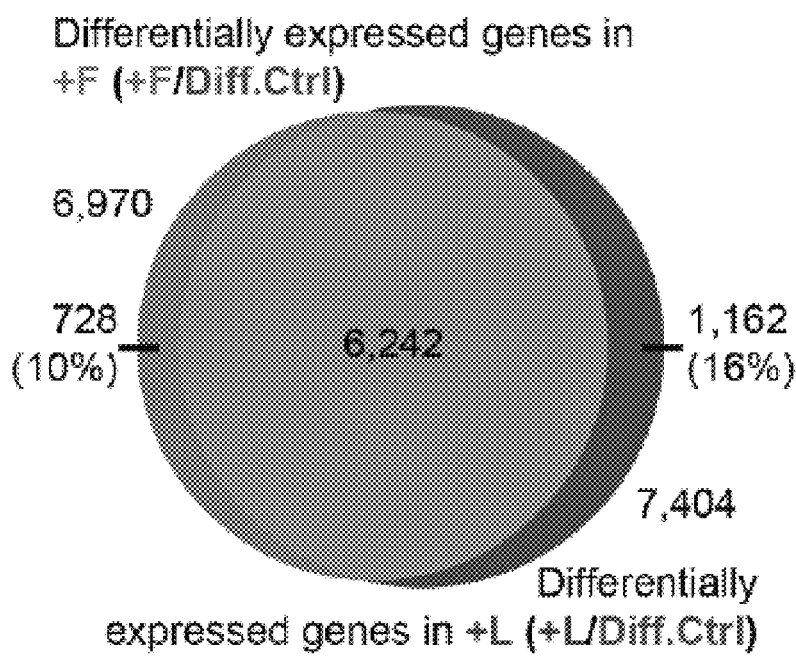
Figure 2E:
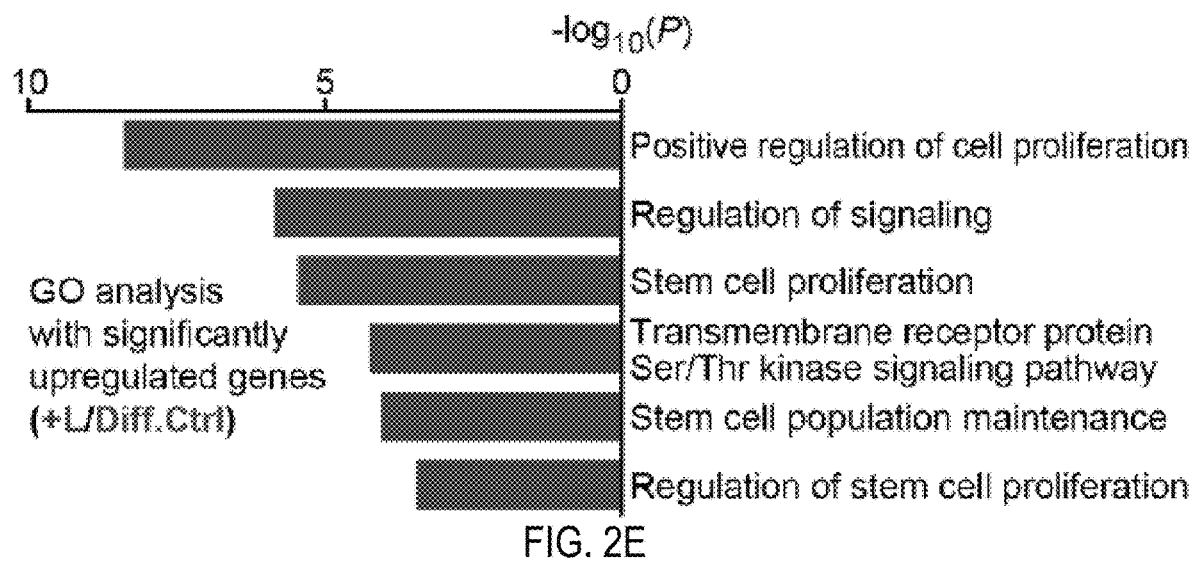
Figure 2F:
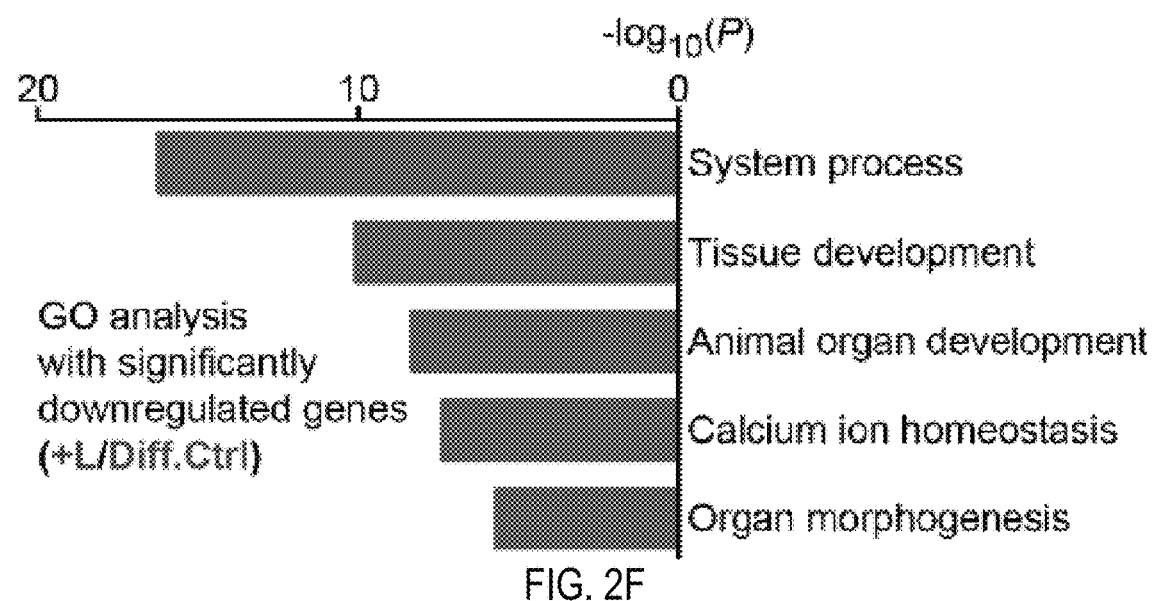
Figure 12A:
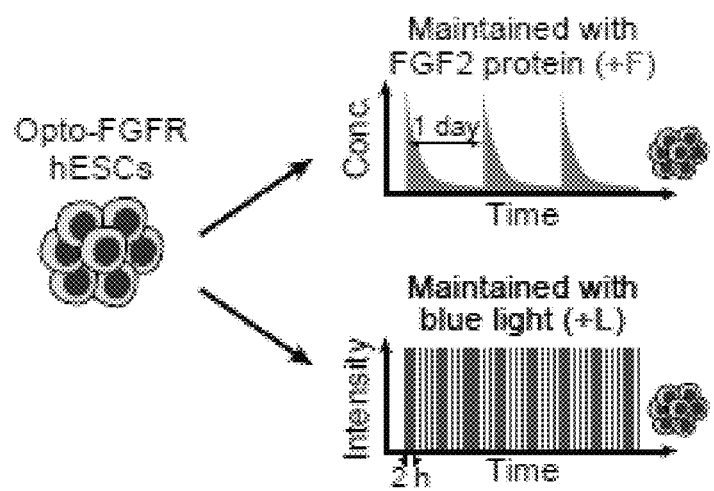
FIG. 12A-12C. Scatter and volcano plots of global transcriptome analyses (RNA-seq).
Figure 12B:
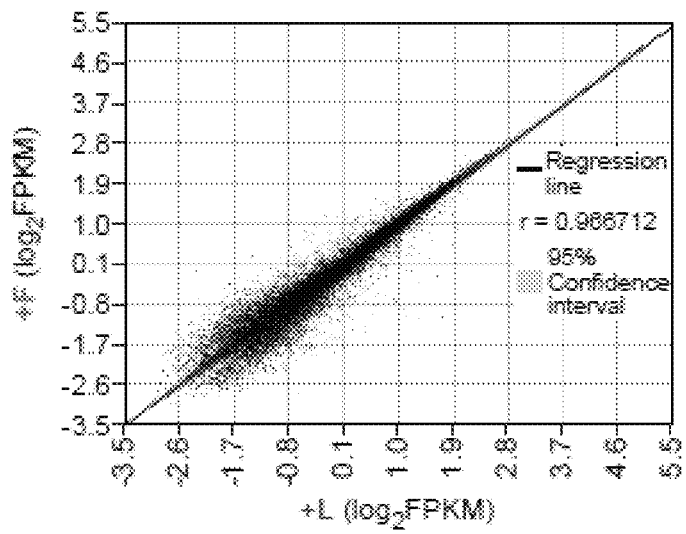
Figure 12C:
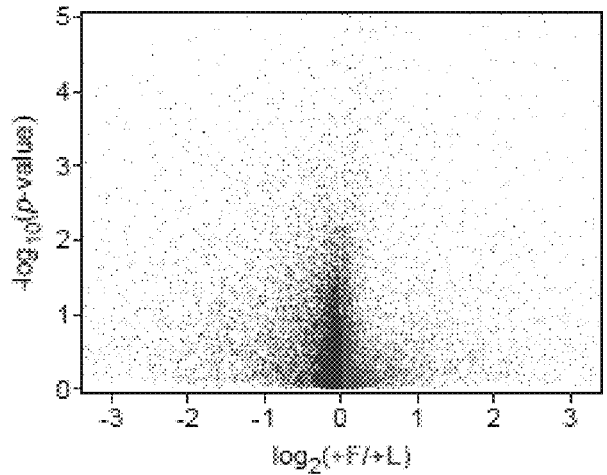

Conservation of pluripotency in optically maintained hPSC. To investigate the similarities at the molecular level between the light illumination and FGF2 treatment conditions that could conserve the pluripotency of hPSCs, we employed global transcriptome analyses (RNA-seq) (FIG. 12). The hierarchical clustering analysis demonstrated that the optically maintained hESCs (1, 5, or 10 min. of blue light illumination every 2 h for 3 weeks) had comparable transcriptional characteristics to that of the cells maintained with FGF2 supplementation, but not to that of the differentiated cells (FIGS. 2A and 2B). Moreover, the expression levels of pluripotency marker genes in the optically maintained hPSCs were similar to the levels in the hPSCs maintained with FGF2 supplementation (FIG. 2C). The majority of significantly differentially expressed genes either in the optically maintained hPSCs or in the hPSCs maintained with FGF2 protein overlapped with those of the differentiated cells (FIG. 2D). In a gene ontology (GO) analysis, the number of stem cell maintenance-related GO terms was significantly over-represented in the upregulated genes of the optically maintained hESCs over the differentiated cells (FIG. 2E), which emphasizes that illumination is sufficient to maintain stem cell pluripotency. In contrast, various cell differentiation-related GO terms were significantly enriched in the downregulated genes of the optically maintained hESCs over the differentiated cells (FIG. 2F), which confirms that the light illumination condition can maintain the transcriptional profiles of human pluripotency similar to that of the FGF2 treatment group and also be sufficient to prevent any spontaneous differentiation of PSCs.

Preserved pluripotency in optically maintained hPSC. To find the direct differentiation potentials of hPSCs optically maintained, we differentiated these cells into three germ layers (FIG. 3A). Quantitative real-time PCR (qRT-PCR) results showed that the expression levels of PAX6 and SOX1 (ectoderm), TBX6 and MSGN1 (mesoderm), and FOXA2 and SOX17 (endoderm) were significantly increased in the differentiated Opto-FGFR hPSCs compared to the undifferentiated cells (FIG. 3B, 3F). The differentiation abilities were also confirmed by immunostaining with NESTIN (ectoderm), TBX6 (mesoderm), and FOXA2 (endoderm) antibodies (FIG. 3C). We further verified the directed differentiation abilities of optically maintained hPSCs into TH+/TJU1+ dopaminergic neuron (ectoderm) or MF20+ skeletal muscle (mesoderm) (FIG. 3D). Additionally, the in vivo differentiation capacity of Opto-FGFR hPSCs was confirmed by a teratoma formation assay. The three germ layers were observed in teratoma tissue via hematoxylin/eosin staining (FIG. 3E, 3G). These results showed that long-term culture conditions along with the optical induction of the FGF signaling pathway maintained the pluripotency of PSCs without losing the cell specification capability toward the three germ layers.

Figure 4A:
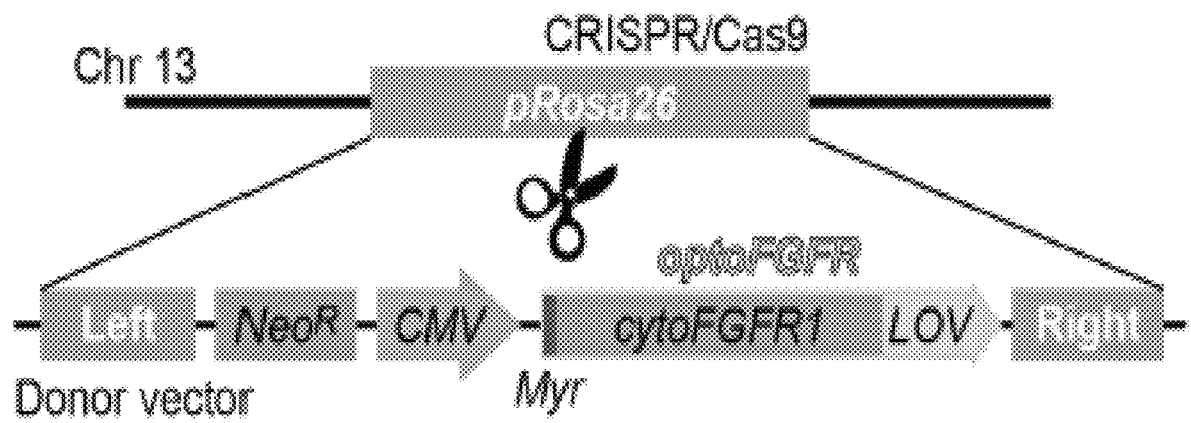
FIG. 4A-4G. Establishment of a novel and efficient FGF2-free piPSC culture system that maintains pluripotency.
Figure 4B:
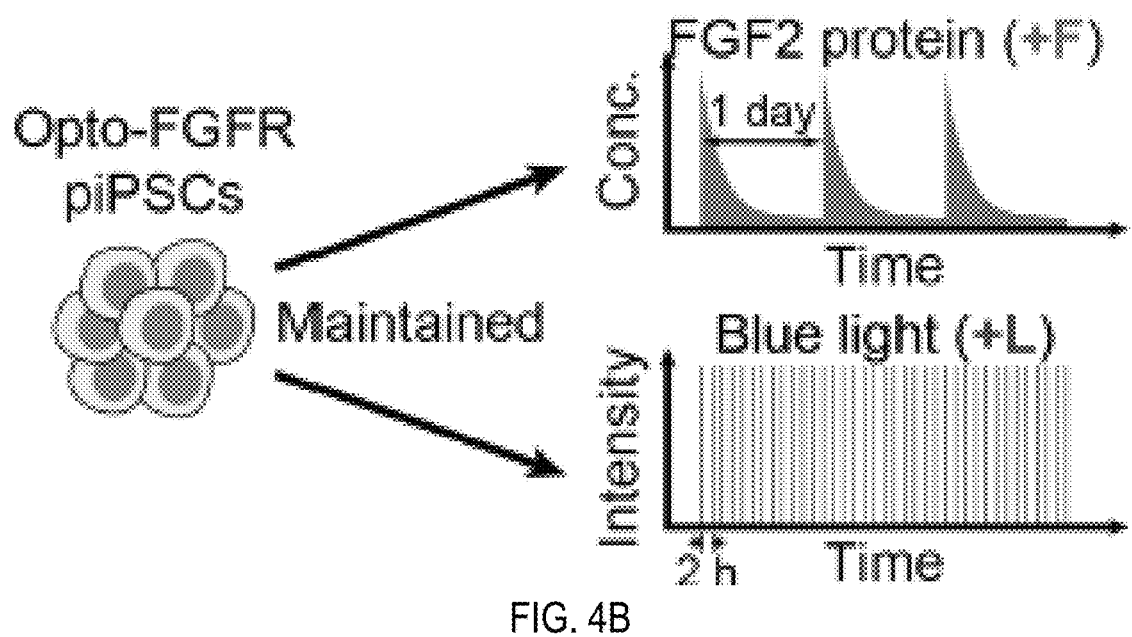
Figure 4C:
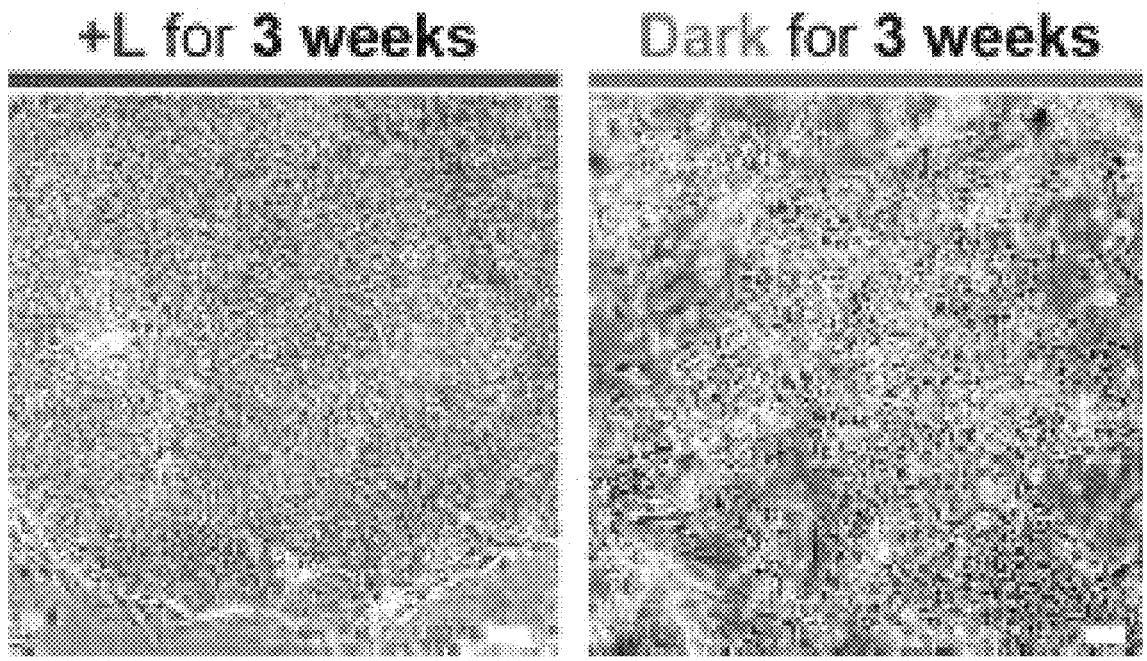
Figure 4D:
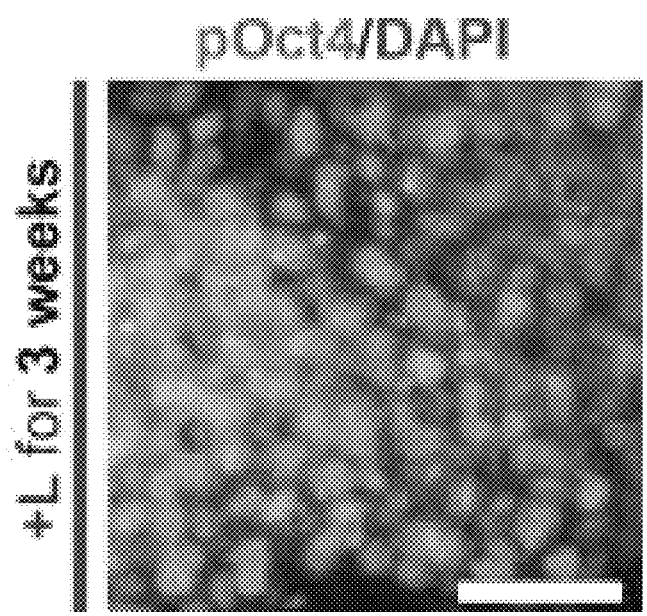
Figure 4E:
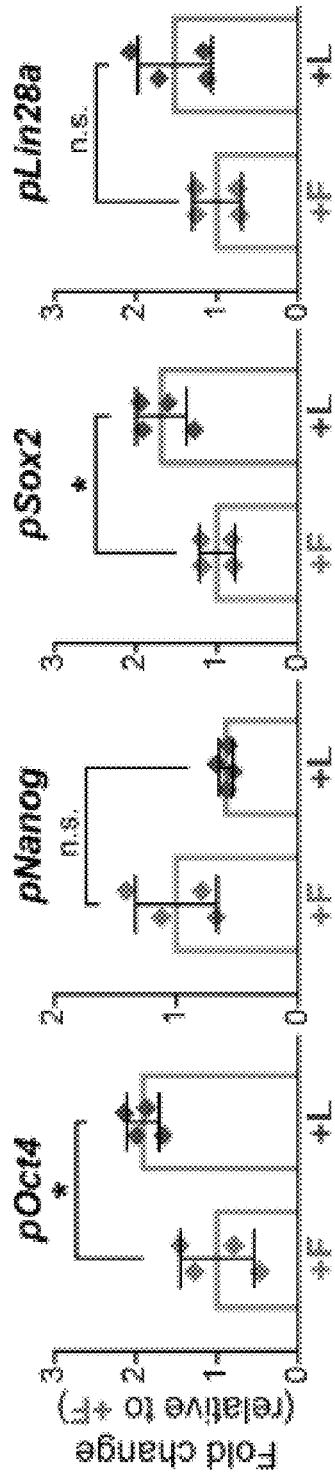
Figure 4F:
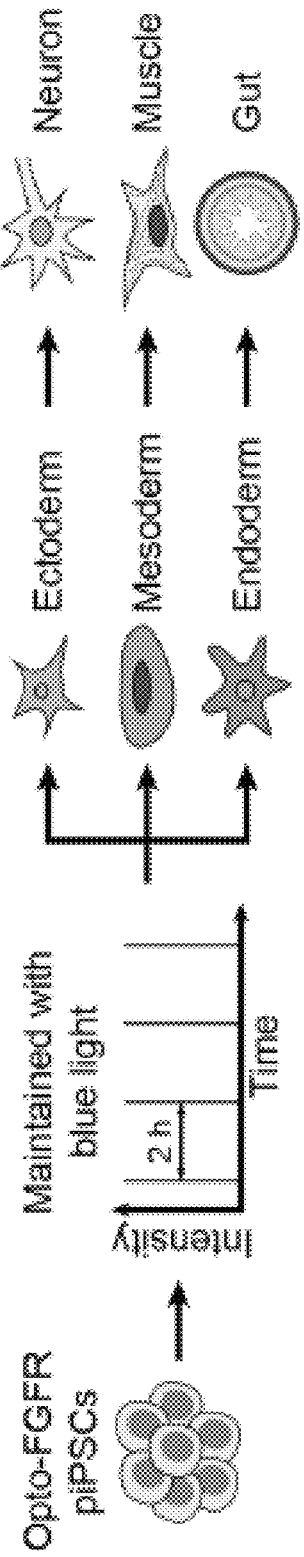
Figure 4G:
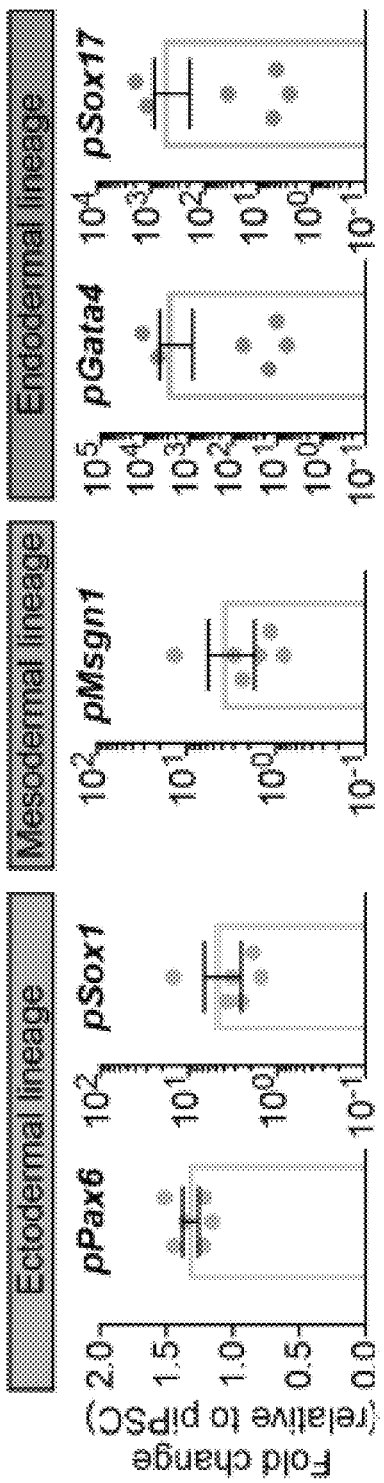
Figure 13D:
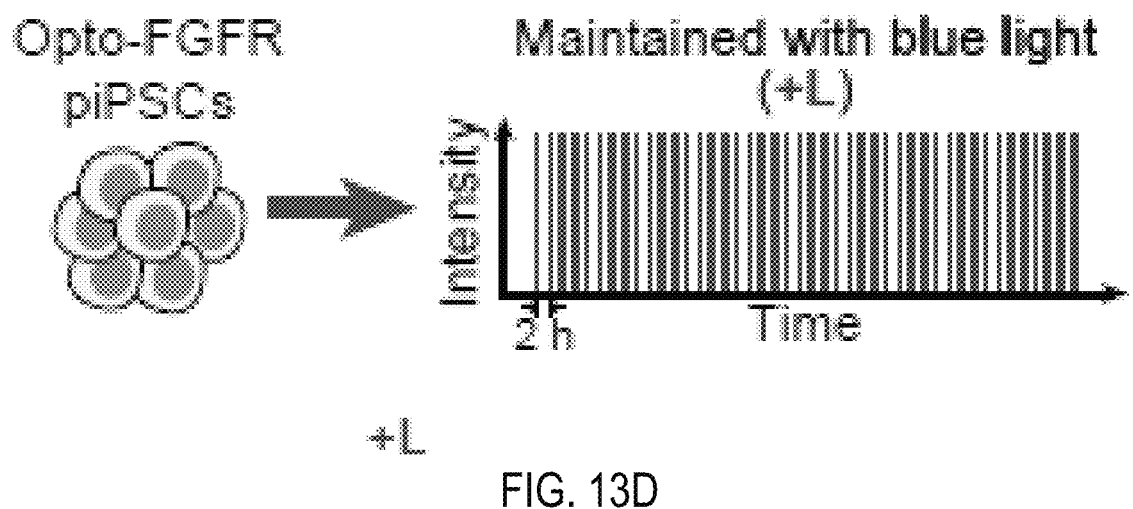
Figure 13E:
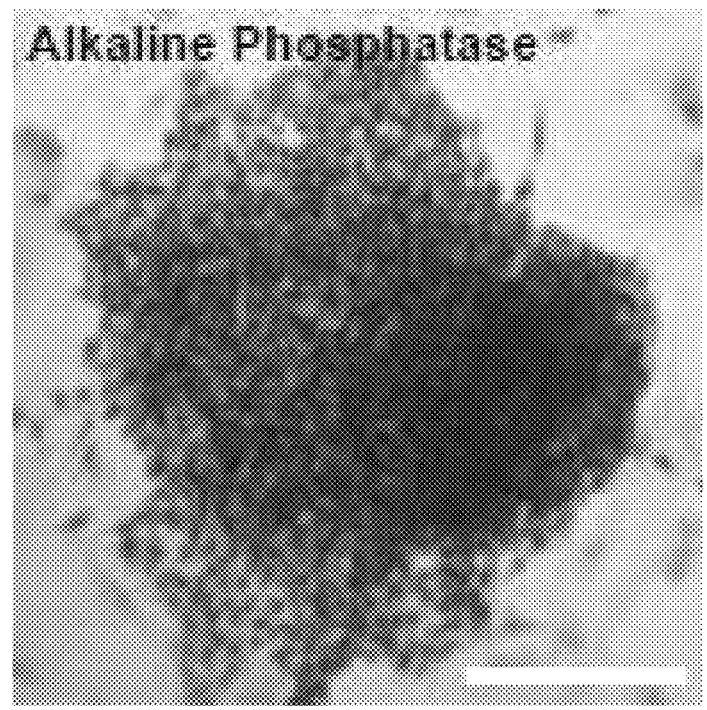
Figure 13F:
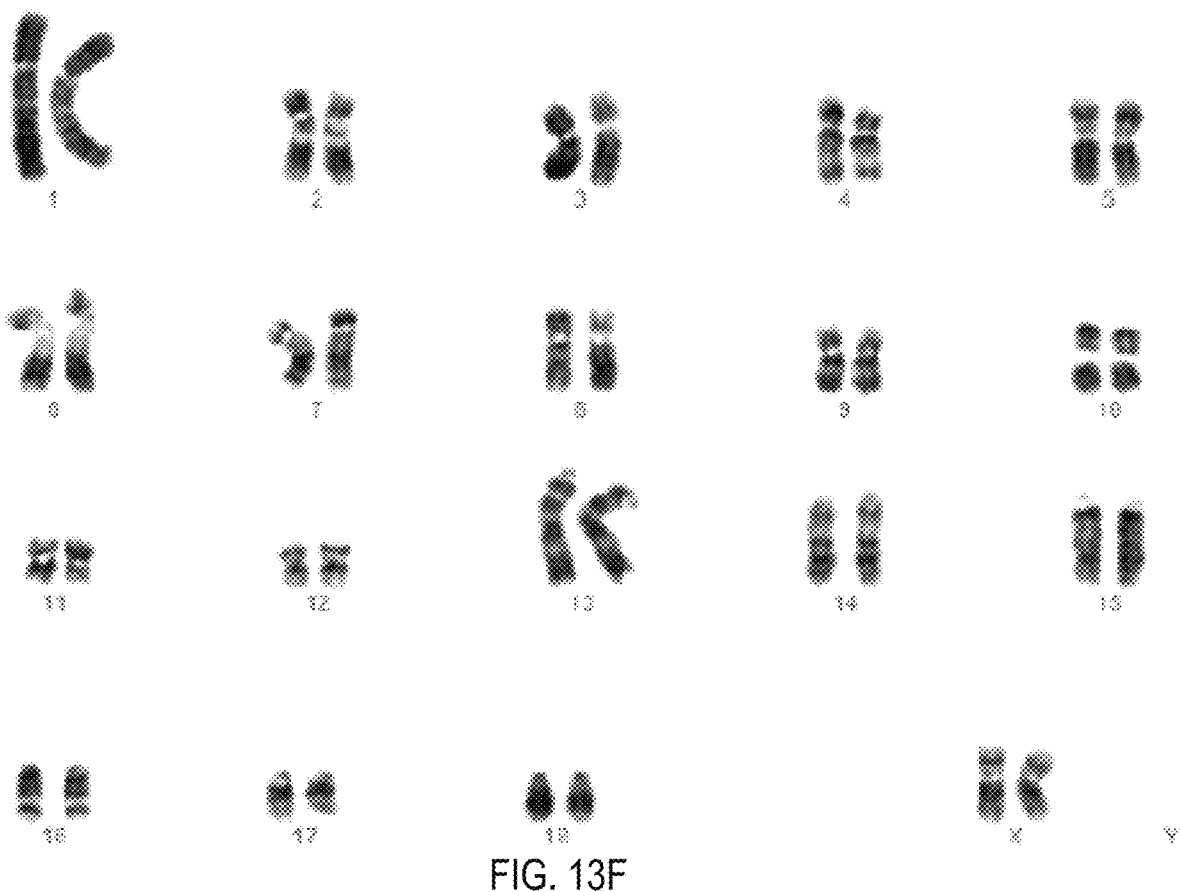
Figure 14A:
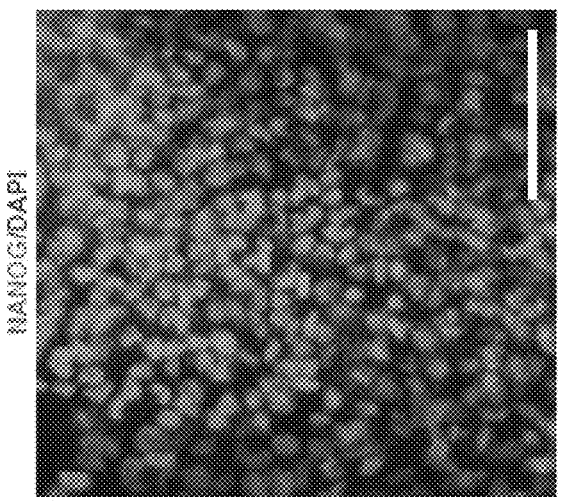
FIG. 14A-14E. Optogenetic activation of FGF signaling is sufficient to maintain pluripotency of hESCs even in a feeder-free culture system.
Figure 14B:
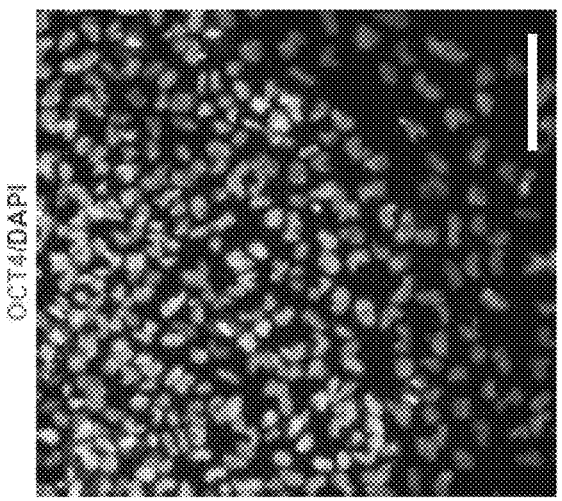
Figure 14C:
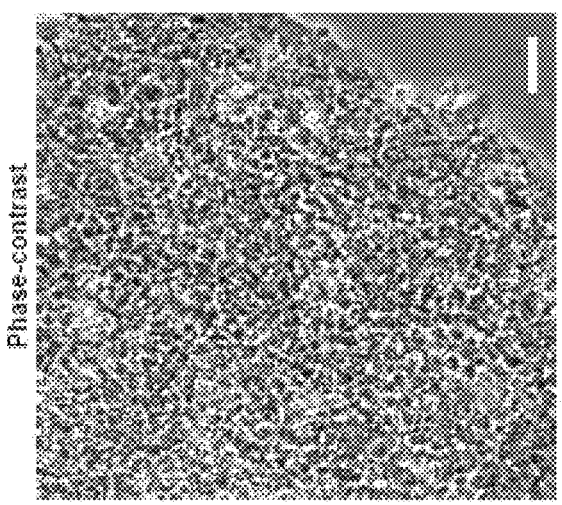
Figure 14E:
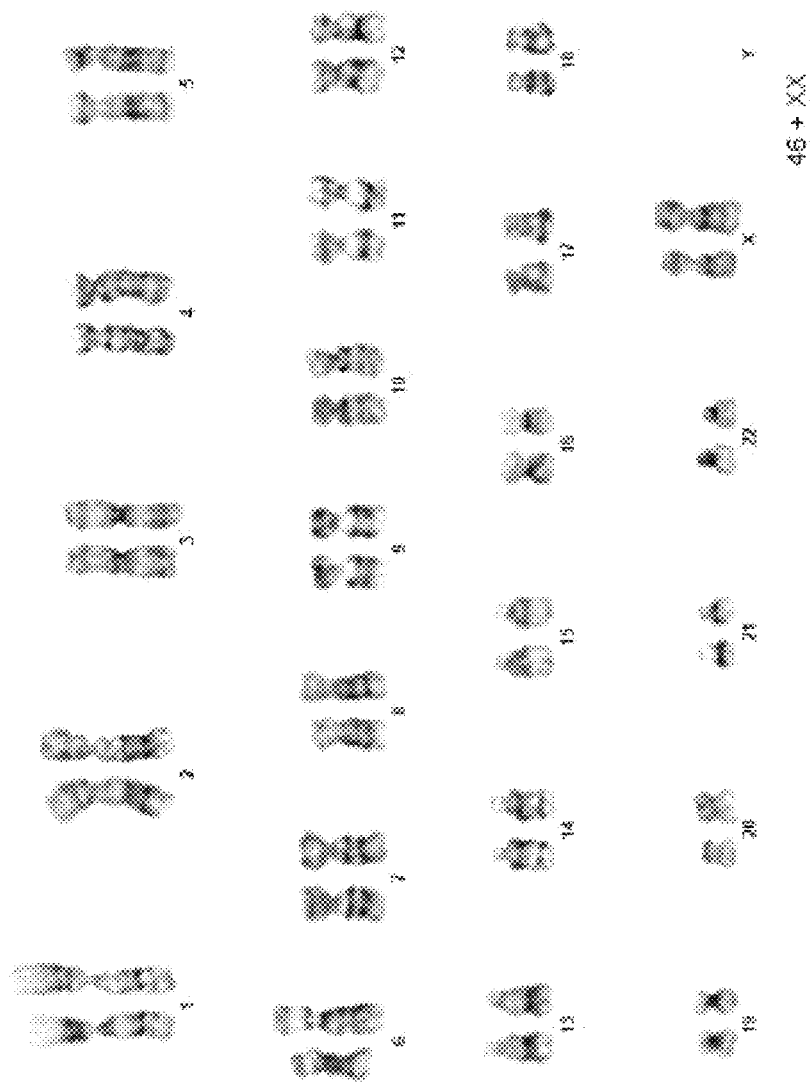
Figure 14D:
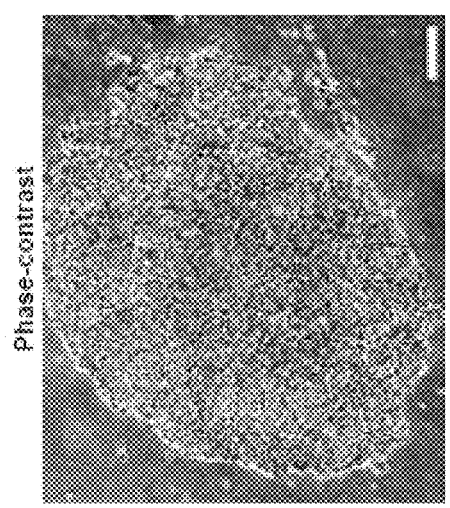

Generation of a novel FGF2-free porcine PSC culture system. Porcine PSCs also show an FGF2-dependency when maintaining their pluripotencies [17,18]. To expand our opto-FGFR system to piPSCs, the opto-FGFR cassette was inserted into the porcine Rosa26 (pRosa26) safe-harbor locus in piPSCs using the CRISPR/Cas9 system (FIG. 4A). For the opto-FGFR knock-in at pRosa26 locus, two gRNAs were designed and applied to target the first intron of pRosa26 [39], and the opto-FGFR knock-in efficiencies were comparable with each other (FIG. 13A). The selected Opto-FGFR piPSC line showed a typical colony morphology and enabled the optical activation of the FGF signaling pathway (FIGS. 13B and 13C). While the Opto-FGFR piPSCs cultured with pulsed blue light maintained the piPSC-colony morphologies for more than 20 weeks, the cells cultured in the dark were fully differentiated after 3 weeks (FIGS. 4B and 4C). The optically maintained alkaline phosphatase-positive piPSCs exhibited a normal karyotype and comparable expression levels of pluripotency markers, such as pOct4, pNanog, pSox2, pLin28a mRNAs and pOct4 protein, to that of the cells maintained with FGF2 supplementation (FIGS. 4D and 4E and FIG. 13D-13F). Furthermore, the optically maintained piPSCs possessed the differentiation potential into the three germ layers (FIGS. 4F and 4G), revealing that our optical induction system for FGF signaling is a suitable culture system for maintaining the pluripotency of piPSC. Overall, these results support that we successfully developed an efficient and economical FGF2-free PSC culture system.

Figure 5A:
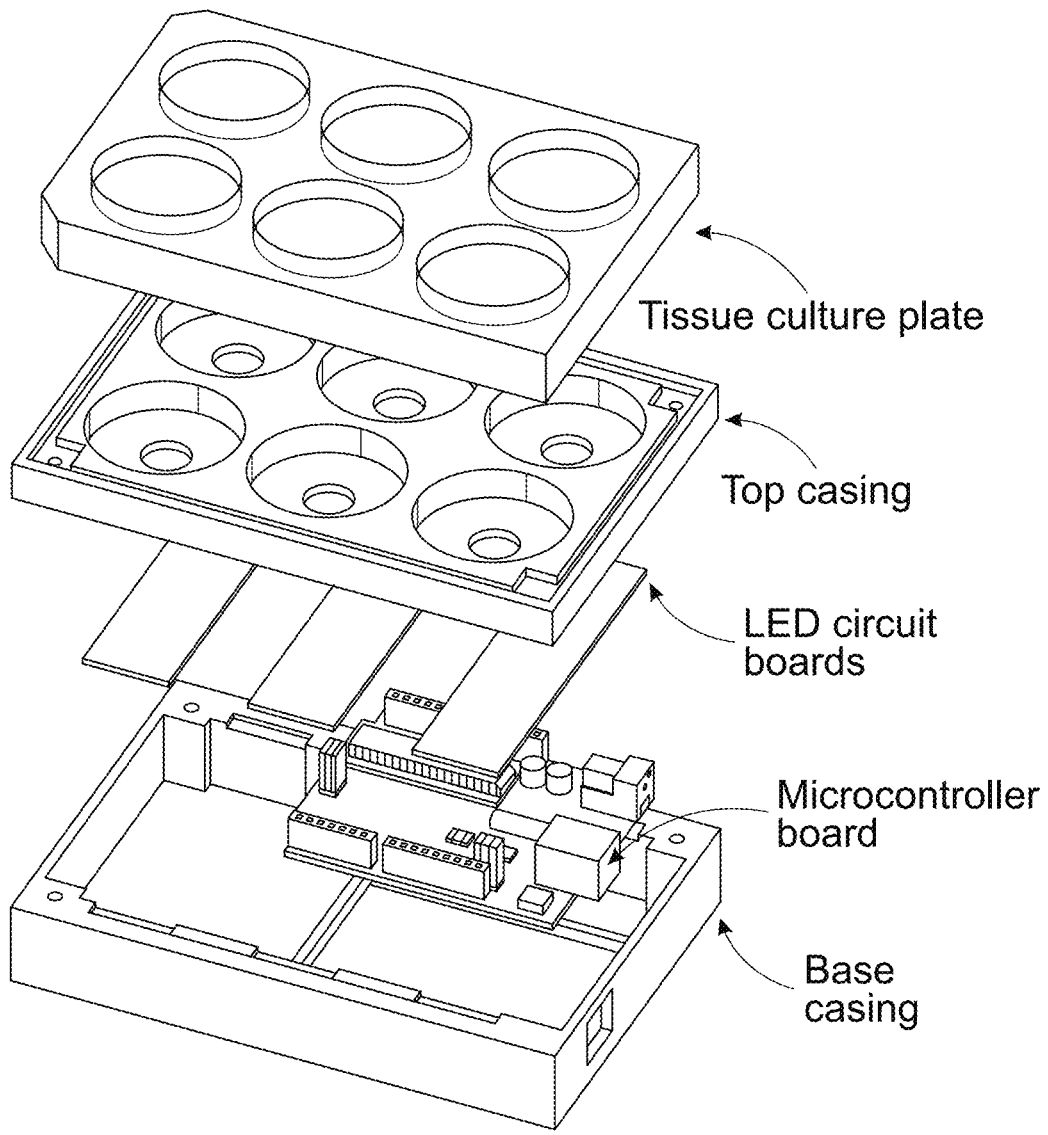
FIG. 5A-5F. Simple and cost-efficient LED illumination system for cell culture.
Figure 5B:
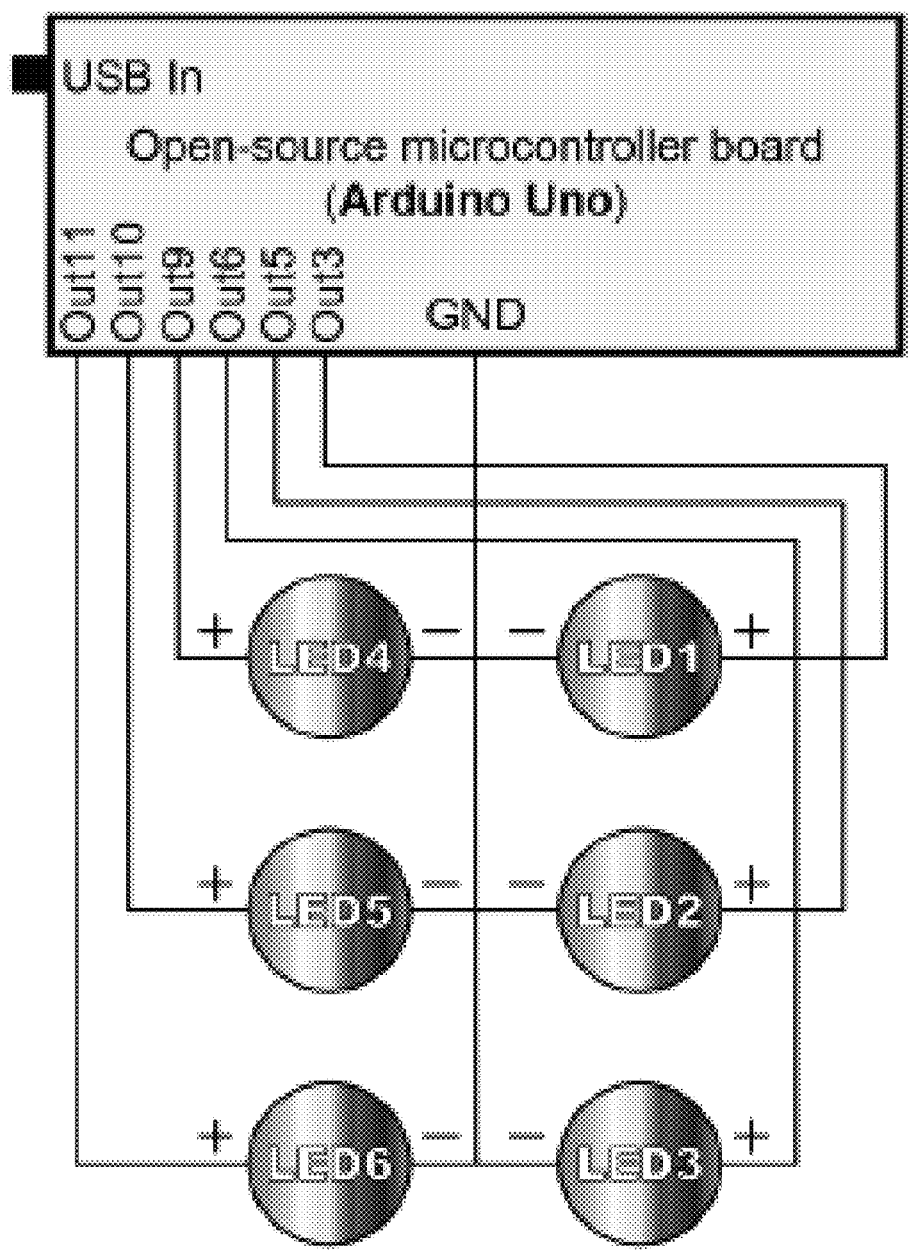
Figure 5C:
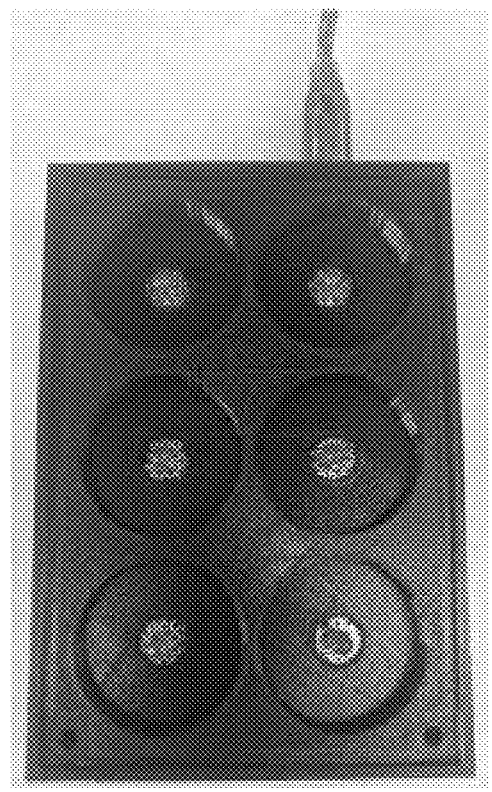
Figure 5D:
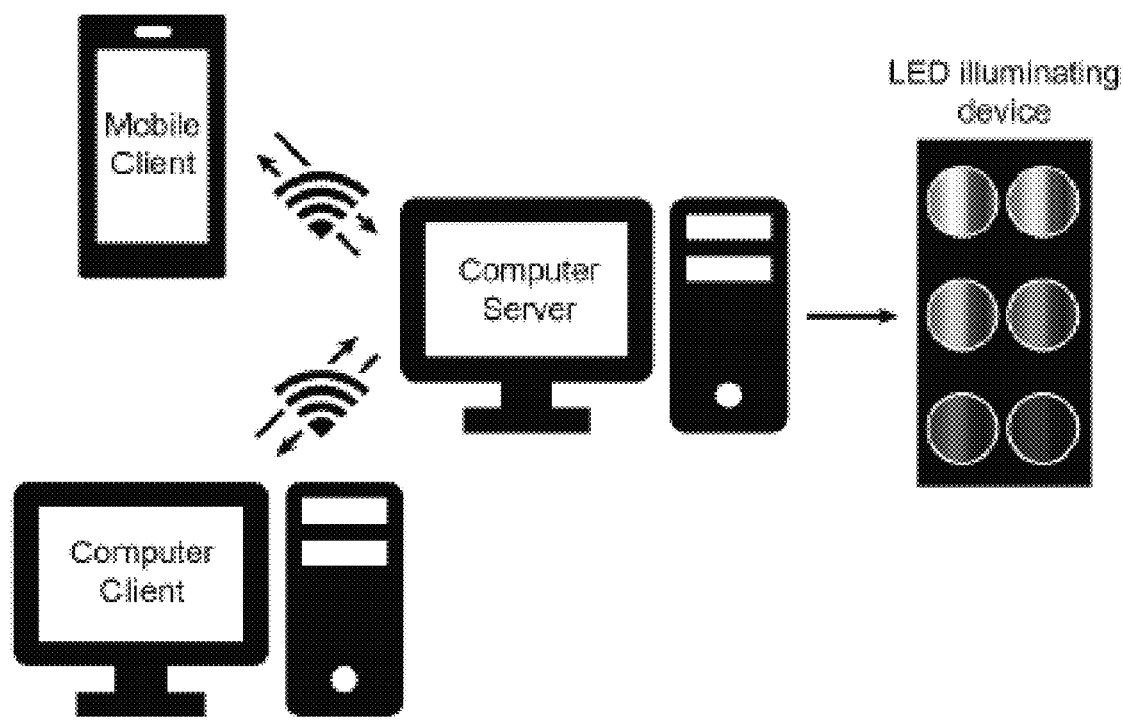
Figure 5E:
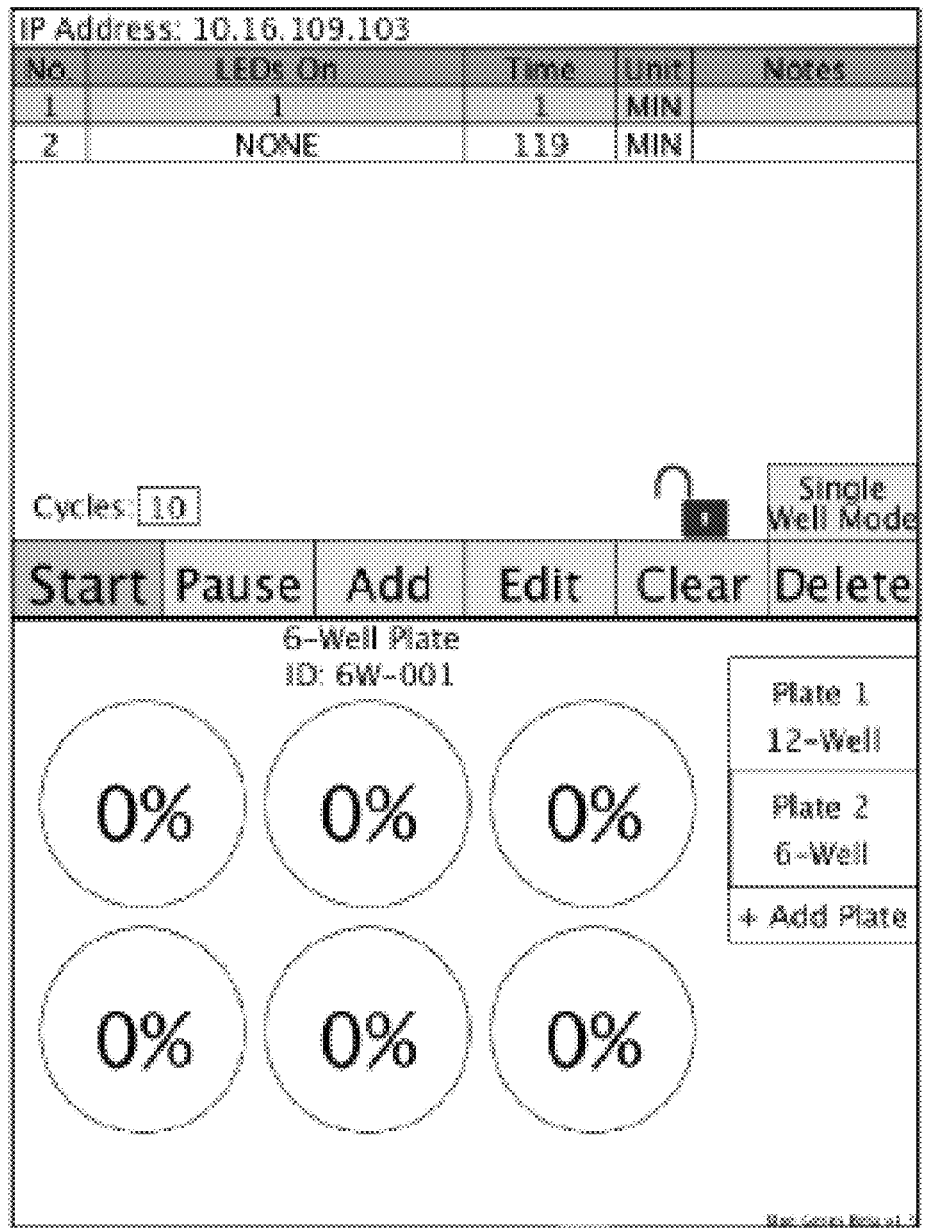
Figure 5F:
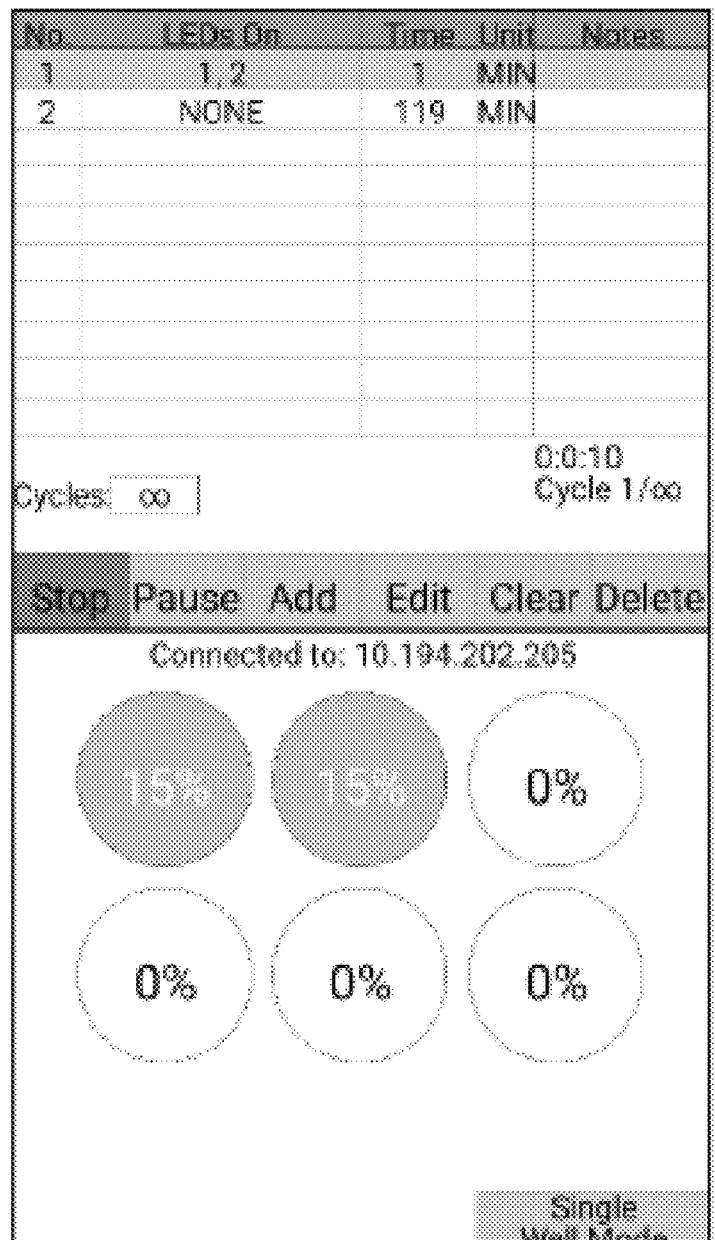

Simple and cost-efficient LED illumination system. To lower the entry barriers and increase control of the optical culture system, we next developed a do it yourself (DIY) light illumination system. We engineered a multi-well LED illuminating device to optically stimulate standard 6-well or 12-well tissue culture plates in a conventional CO2 incubator (FIG. 5A). The LED illuminating device consists of 6 or 12 LEDs of any color, a circuit board, an open-source microcontroller, and an enclosing plastic casing. The LEDs were soldered onto the circuit board and are controlled by the microcontroller (FIGS. 5A and 5B). The casing was designed using computer-aided design software and printed using a 3D plastic printer (FIG. 5A, 5C). Through our developed software and mobile application, the LED illuminating devices are remotely controlled by any computer or smartphone via a wireless connection (FIG. 5D). Users can easily control the pulse time length, frequency, and intensity of light illumination, and check current status of the LED illumination system (FIGS. 5E and 5F), which is seamlessly adopted in our routine stem cell culture. This DIY system provides the opportunity to apply optical culture systems to cell cultures in any laboratory.

Discussion

We describe a novel and efficient culture system for PSCs via the activation of the FGF pathway to maintain PSCs without the need for supplementation of FGF2 recombinant protein. Previous reports have demonstrated the optical activation of receptor tyrosine kinases in immortalized cell lines [31,40,41] and developing embryos [42,43] as an initial step in evolving such optical technologies. Although a study using the optical control of ERK phosphorylation reported a perturbation of patterning and morphogenesis in *Drosophila* embryos [42], other studies did not report any biologically relevant phenotypes; therefore, translating these approaches for use with PSCs has remained challenging. Here, we extend the approach to human and porcine PSCs and provide clear evidence that our Opto-FGFR PSCs are sufficiently maintained by blue light illumination and without the need for FGF2 protein supplementation. Although overall patterns of protein phosphorylation in the blue light illuminated group were similar to FGF2 protein treated group, MSK1/2, eNOS, and HSP27, which are known to regulate cell proliferation [44-46], were slightly more phosphorylated in the blue light exposed group than FGF2 treated group (Supplementary FIG. 3). Since there is no need to supplement FGF2 protein, the media does not need to be frequently changed in the optical PSC culture system. In feeder-free culture systems, very high concentrations of FGF2 (up to 100 ng/mL) are required for promoting self-renewal and inhibiting spontaneous differentiation of hPSCs [15]. Even in a feeder-free culture system, we succeeded in maintaining pluripotency of hESCs using our optical culture system (FIG. 14). Moreover, the optically maintained PSCs appeared to retain the normal differentiation potential of traditional PSCs.

There are various kinds of photoactivatable proteins available for optogenetic approaches [9,10]. Using the photolyase homology region of the Cry2 protein (Cry2 PHR [47]) and LOV domain [35], two pioneer researches have established the optical activation systems of the FGF signaling pathway [31,40]. In the present study, the photosensory LOV domain served as an initiator in the light-induced intermolecular signal transduction cascade of the FGF signaling pathway (termed as opto-FGFR signaling) for maintaining the pluripotency of mammalian PSCs, without FGF2 protein supplementation. Although we could optically activate FGF signaling in human embryonic kidney cells (HEK293T) and hESCs transiently transfected with the Cry2 PHR-based opto-FGFR (FIG. 15), we selected the LOV domain as a photodimerizable domain because of two reasons: the LOV domain has a shorter length (LOV, 432 bp or 144 aa [31] vs Cry2 PHR, 1506 bp or 502 aa [40]), which is more favorable for knock-in, and LOV domain has a shorter dissociation time after light withdrawal (LOV $t_{1/2}$ ¼ 2.5 min. [31] vs Cry2 PHR $t_{1/2}$ ¼ 5-6 min. [9,10]), which is more advantageous for accurate adjustment of the opto-FGFR signaling in PSC, than others. It is important to select an appropriate photosensory domain as the light-sensing actuator module for a given optogenetic modulation system in PSCs. In future work, it might also be important to build a systematic approach to select an appropriate photosensory domain for a given signaling pathway in a given cell type.

The current stem cell culture system is heavily dependent on random distribution of expensive and thermo-unstable recombinant proteins in a dish, which could jeopardize future mass production of human stem cells for a population-wide cell therapy. Our Opto-FGFR PSCs enable optical activation without any exogenous FGF2 recombinant proteins and offer spatiotemporally precise optical control of stem cell behaviors. Beyond implementing a new technology in the stem cell field, our experimental data could help lead to the development of a potential therapeutic cure against many human diseases by modulating multiple signaling pathways other than FGF2 and maximizing the potential of human PSCs. While our optogenetic culture system to stimulate the FGF signaling pathway is suitable for maintaining the pluripotency of PSCs, further studies to activate the LIF and/or Activin signaling via optogenetic stimulation for generating PSCs in a naïve state of pluripotency [48] will be of great interest. Furthermore, it will be interesting to see whether other signaling molecules to maintain the pluripotency of PSCs, such as insulin and/or TGFβ1 (or Nodal) [49], can be replaceable by the photo-activatable system. Regarding hiPSC culture for potential therapeutic application, developing an optogenetic system to activate insulin and/or TGFβ1 (or Nodal) signaling would be one way to reduce its production costs. In addition, because the FGF signaling pathway is a key factor for several differentiation protocols of PSCs, including ectodermal and neuronal differentiation protocols, our optogenetic system could be applied to the differentiation researches.

As many researchers adopted optogenetic techniques particularly for neuroscience field, there is a growing concern of a possible phototoxicity. For example, other group recently reported a phototoxicity caused by blue light illumination in in vitro culture of neural cells [50]. However, the light intensity (1 mW/mm$^2$) in their illumination condition is 1000-fold higher than that of our culture condition (1 μW/mm$^2$), and the frequency (1 Hz) in their condition is 7200-fold higher than that of our condition (0.14 mHz); which are why we did not detect any noticeable toxicity during over 1-year culture. It will be important to know what the susceptible ranges of the light illumination conditions in different cell types in future is. While it still needs to study more to find an ideal illumination conditions, '5 min. blue light illumination in every 2 h' was sufficient to maintain the pluripotency of PSCs; further studies to exquisitely optimize the illuminating conditions, such as pulse width, frequency, and intensity of illumination, will be of great interest.

The current animal agriculture and husbandry methods cause significant environmental issues such as greenhouse gas emissions, fresh water consumption, and arable land usage. As an alternative, cellular agriculture [51] or 'lab-grown meats [52]' have been introduced and social consent is growing due to ethical and environmentally friendly concepts. However, the production costs and use of animal-derived thermo-unstable recombinant proteins during the cellular agriculture process are barriers to entering the market for mass consumption. Based on our calculation, recombinant FGF2 protein for 1 billion of PSC culture costs ~$14,000 weekly. In addition, due to thermal and chemo-physical instabilities, FGF2 is recommended to be freshly added into the media and it requires additional labor fees. In conclusion, our opto-FGFR system in livestock PSCs can be a realistic solution to decrease these production costs.

Although researchers may consider that it is too early to know whether genetic engineering techniques will be safe in the clinic, the results of clinical trials of CRISPR/Cas9-mediated genome editing have been promising up to now [53-55]. We carefully speculate that the CRISPR-based genome editing of PSCs would be clinically possible with additional development and troubleshooting. Based on our karyotypic analysis results, our CRISPR-based genome editing of PSCs did not cause detectable karyotypic abnormalities (FIG. 11F FIG. 13F, and FIG. 14E); however, we will study much details of any possible genetic aberrations in future. If we employ newly developed genetic engineering techniques, such as prime editors [56], high-fidelity CRISPR/Cas9 nucleases [57], and CRISPR/Cas9 nickase [58], to increase accuracy and to reduce off-target effects, the safety issues can be mitigated. While it is hard to precisely estimate the cost to produce genetically engineered cell lines through the CRISPR system, there would not be an additional expense after upfront cost after production.

Currently, there are a few culture optogenetics systems on the market, but these systems are all very expensive. High cost commercial products prevent large volume optogenetics studies and thus, limit the rate of research in this field. There is also a lack of instrumentation that allows for precise control of illumination and remote monitoring of multiple culture plates. Our DIY illumination system is a hardware, software, and mobile application system capable of precise control and real-time monitoring of cell culture illumination that can serve as an inexpensive alternative to high cost commercial products. This illumination system was designed to be easy-to-assemble, easy-to-use, and low-cost, utilizing 3D printing of thermoplastic materials, programmable open-source electronics, and other readily-available electronic parts. Additionally, this system was designed to be adjustable and be customized to the individual researcher. The 3D models and source code are publicly available to be edited for any specific needs. Our cost saving PSC culture system with illumination system could help understanding disease mechanism. Furthermore, we did not find any notable safety issue, even in the feeder-free condition during the culture period with blue light illumination. Additionally, the LED illuminating device can be customized with any color LED to be used with any photosynthetic protein of interest. This DIY system provides the opportunity to apply a flexible optical culture system to cell cultures in any laboratory.

Conclusion

Our approach for the optical maintenance of human and porcine PSCs provides new insights for an alternative synthetic approach for the next generation in stem cell research. Furthermore, considering the number of signaling pathways that are crucial for controlling cell specification processes, our Opto-FGFR PSCs are a proof-of-concept for the optical control over a plethora of mammalian stem cell fates.

References

1. G. Nagel, D. Ollig, M. Fuhrmann, S. Kateriya, A. M. Musti, E. Bamberg, P. Hegemann, Channelrhodopsin-1: a light-gated proton channel in green algae, Science 296 (5577) (2002) 2395-2398.
2. K. Deisseroth, G. Feng, A. K. Majewska, G. Miesenbock, A. Ting, M. J. Schnitzer, Next-generation optical technologies for illuminating genetically targeted brain circuits, J. Neurosci. 26 (41) (2006) 10380-10386.
3. L. Fenno, O. Yizhar, K. Deisseroth, The development and application of optogenetics, Annu. Rev. Neurosci. 34 (2011) 389-412.

4. M. Yazawa, A. M. Sadaghiani, B. Hsueh, R. E. Dolmetsch, Induction of protein-protein interactions in live cells using light, Nat. Biotechnol. 27 (10) (2009) 941-945.
5. Y. I. Wu, D. Frey, O. I. Lungu, A. Jaehrig, I. Schlichting, B. Kuhlman, K. M. Hahn, A genetically encoded photoactivatable Rac controls the motility of living cells, Nature 461 (7260) (2009) 104-108.
6. A. Levskaya, O. D. Weiner, W. A. Lim, C. A. Voigt, Spatiotemporal control of cell signalling using a light-switchable protein interaction, Nature 461 (7266) (2009) 997-1001.
7. S. Shimizu-Sato, E. Huq, J. M. Tepperman, P. H. Quail, A light-switchable gene promoter system, Nat. Biotechnol. 20 (10) (2002) 1041-1044.
8. M. J. Kennedy, R. M. Hughes, L. A. Peteya, J. W. Schwartz, M. D. Ehlers, C. L. Tucker, Rapid blue-light-mediated induction of protein interactions in living cells, Nat. Methods 7 (12) (2010) 973-975.
9. K. Zhang, B. Cui, Optogenetic control of intracellular signaling pathways, Trends Biotechnol. 33 (2) (2015) 92-100.
10. D. Tischer, O. D. Weiner, Illuminating cell signalling with optogenetic tools, Nat. Rev. Mol. Cell Biol. 15 (8) (2014) 551-558.
11. L. J. Bugaj, A. T. Choksi, C. K. Mesuda, R. S. Kane, D. V. Schaffer, Optogenetic protein clustering and signaling activation in mammalian cells, Nat. Methods 10 (3) (2013) 249-252.
12. M. K. Furue, J. Na, J. P. Jackson, T. Okamoto, M. Jones, D. Baker, R. Hata, H. D. Moore, J. D. Sato, P. W. Andrews, Heparin promotes the growth of human embryonic stem cells in a defined serum-free medium, Proc. Natl. Acad. Sci. U.S.A. 105 (36) (2008) 13409-13414.
13. P. J. Tesar, J. G. Chenoweth, F. A. Brook, T. J. Davies, E. P. Evans, D. L. Mack, R. L. Gardner, R. D. McKay, New cell lines from mouse epiblast share defining features with human embryonic stem cells, Nature 448 (7150) (2007) 196-199.
14. K. Takahashi, K. Tanabe, M. Ohnuki, M. Narita, T. Ichisaka, K. Tomoda, S. Yamanaka, Induction of pluripotent stem cells from adult human fibroblasts by defined factors, Cell 131 (5) (2007) 861-872.
15. M. E. Levenstein, T. E. Ludwig, R. H. Xu, R. A. Llanas, K. VanDenHeuvel-Kramer, D. Manning, J. A. Thomson, Basic fibroblast growth factor support of human embryonic stem cell self-renewal, Stem Cell. 24 (3) (2006) 568-574.
16. J. A. Thomson, J. Itskovitz-Eldor, S. S. Shapiro, M. A. Waknitz, J. J. Swiergiel, V. S. Marshall, J. M. Jones, Embryonic stem cell lines derived from human blastocysts, Science 282 (5391) (1998) 1145-1147.
17. F. D. West, S. L. Terlouw, D. J. Kwon, J. L. Mumaw, S. K. Dhara, K. Hasneen, J. R. Dobrinsky, S. L. Stice, Porcine induced pluripotent stem cells produce chimeric offspring, Stem Cells Dev. 19 (8) (2010) 1211-1220.
18. T. Ezashi, B. P. Telugu, A. P. Alexenko, S. Sachdev, S. Sinha, R. M. Roberts, Derivation of induced pluripotent stem cells from pig somatic cells, Proc. Natl. Acad. Sci. U.S.A. 106 (27) (2009) 10993-10998.
19. M. Amit, M. K. Carpenter, M. S. Inokuma, C. P. Chiu, C. P. Harris, M. A. Waknitz, J. Itskovitz-Eldor, J. A. Thomson, Clonally derived human embryonic stem cell lines maintain pluripotency and proliferative potential for prolonged periods of culture, Dev. Biol. 227 (2) (2000) 271-278.
20. N. Itoh, D. M. Ornitz, Evolution of the Fgf and Fgfr gene families, Trends Genet. 20 (11) (2004) 563-569.
21. H. D. Beer, L. Vindevoghel, M. J. Gait, J. M. Revest, D. R. Duan, I. Mason, C. Dickson, S. Werner, Fibroblast growth factor (FGF) receptor 1-IIIb is a naturally occurring functional receptor for FGFs that is preferentially expressed in the skin and the brain, J. Biol. Chem. 275 (21) (2000) 16091-16097.
22. I. Urakawa, Y. Yamazaki, T. Shimada, K. Iijima, H. Hasegawa, K. Okawa, T. Fujita, S. Fukumoto, T. Yamashita, Klotho converts canonical FGF receptor into a specific receptor for FGF23, Nature 444 (7120) (2006) 770-774.
23. D. M. Ornitz, A. Yayon, J. G. Flanagan, C. M. Svahn, E. Levi, P. Leder, Heparin is required for cell-free binding of basic fibroblast growth factor to a soluble receptor and for mitogenesis in whole cells, Mol. Cell Biol. 12 (1) (1992) 240-247.
24. M. Mohammadi, I. Dikic, A. Sorokin, W. H. Burgess, M. Jaye, J. Schlessinger, Identification of six novel autophosphorylation sites on fibroblast growth factor receptor 1 and elucidation of their importance in receptor activation and signal transduction, Mol. Cell Biol. 16 (3) (1996) 977-989.
25. G. Chen, D. R. Gulbranson, P. Yu, Z. Hou, J. A. Thomson, Thermal stability of fibroblast growth factor protein is a determinant factor in regulating self-renewal, differentiation, and reprogramming in human pluripotent stem cells, Stem Cell. 30 (4) (2012) 623-630.
26. I. Y. Choi, H. Lim, K. Estrellas, J. Mula, T. V. Cohen, Y. Zhang, C. J. Donnelly, J. P. Richard, Y. J. Kim, H. Kim, Y. Kazuki, M. Oshimura, H. L. Li, A. Hotta, J. Rothstein, N. Maragakis, K. R. Wagner, G. Lee, Concordant but varied phenotypes among duchenne muscular dystrophy patient-specific myoblasts derived using a human iPSC-based model, Cell Rep. 15 (10) (2016) 2301-2312.
27. P. Mali, L. Yang, K. M. Esvelt, J. Aach, M. Guell, J. E. DiCarlo, J. E. Norville, G. M. Church, RNA-guided human genome engineering via Cas9, Science 339 (6121) (2013) 823-826.
28. I. Y. Choi, H. Lim, H. J. Cho, Y. Oh, B. K. Chou, H. Bai, L. Cheng, Y. J. Kim, S. Hyun, H. Kim, J. H. Shin, G. Lee, Transcriptional landscape of myogenesis from human pluripotent stem cells reveals a key role of TWIST1 in maintenance of skeletal muscle progenitors, Elife 9 (2020).
29. H. Lim, I. Y. Choi, G. Lee, Profiling individual human embryonic stem cells by quantitative RT-PCR, J. Vis. Exp. 87 (2014) e51408.
30. S. Kriks, J. W. Shim, J. Piao, Y. M. Ganat, D. R. Wakeman, Z. Xie, L. Carrillo-Reid, G. Auyeung, C. Antonacci, A. Buch, L. Yang, M. F. Beal, D. J. Surmeier, J. H. Kordower, V. Tabar, L. Studer, Dopamine neurons derived from human ES cells efficiently engraft in animal models of Parkinson's disease, Nature 480 (7378) (2011) 547-551.
31. M. Grusch, K. Schelch, R. Riedler, E. Reichhart, C. Differ, W. Berger, A. Ingles-Prieto, H. Janovjak, Spatiotemporally precise activation of engineered receptor tyrosine kinases by light, EMBO J. 33 (15) (2014) 1713-1726.
32. K. Huang, T. Merkle, C. F. Beck, Isolation and characterization of a *Chlamydomonas* gene that encodes a putative blue-light photoreceptor of the phototropin family, Physiol. Plant 115 (4) (2002) 613-622.
33. T. Kinoshita, M. Doi, N. Suetsugu, T. Kagawa, M. Wada, K. Shimazaki, Phot1 and phot2 mediate blue light regulation of stomatal opening, Nature 414 (6864) (2001) 656-660.

34. F. Takahashi, D. Yamagata, M. Ishikawa, Y. Fukamatsu, Y. Ogura, M. Kasahara, T. Kiyosue, M. Kikuyama, M. Wada, H. Kataoka, Aureochrome, a photoreceptor required for photomorphogenesis in stramenopiles, Proc. Natl. Acad. Sci. U.S.A 104 (49) (2007) 19625-19630.

35. T. Toyooka, O. Hisatomi, F. Takahashi, H. Kataoka, M. Terazima, Photoreactions of aureochrome-1, Biophys. J. 100 (11) (2011) 2801-2809.

36. Y. Oh, G. S. Cho, Z. Li, I. Hong, R. Zhu, M. J. Kim, Y. J. Kim, E. Tampakakis, L. Tung, R. Huganir, X. Dong, C. Kwon, G. Lee, Functional coupling with cardiac muscle promotes maturation of hpsc-derived sympathetic neurons, Cell Stem Cell 19 (1) (2016) 95-106.

37. L. Cong, F. A. Ran, D. Cox, S. Lin, R. Barretto, N. Habib, P. D. Hsu, X. Wu, W. Jiang, L. A. Marraffini, F. Zhang, Multiplex genome engineering using CRISPR/Cas systems, Science 339 (6121) (2013) 819-823.

38. S. Lotz, S. Goderie, N. Tokas, S. E. Hirsch, F. Ahmad, B. Comeo, S. Le, A. Banerjee, R. S. Kane, J. H. Stem, S. Temple, C. A. Fasano, Sustained levels of FGF2 maintain undifferentiated stem cell cultures with biweekly feeding, PloS One 8 (2) (2013) e56289.

39. Z. Xie, D. Pang, K. Wang, M. Li, N. Guo, H. Yuan, J. Li, X. Zou, H. Jiao, H. Ouyang, Z. Li, X. Tang, Optimization of a CRISPR/Cas9-mediated knock-in strategy at the porcine Rosa26 locus in porcine foetal fibroblasts, Sci. Rep. 7 (1) (2017) 3036.

40. N. Kim, J. M. Kim, M. Lee, C. Y. Kim, K. Y. Chang, W. D. Heo, Spatiotemporal control of fibroblast growth factor receptor signals by blue light, Chem Biol. 21 (7) (2014) 903-912.

41. Y. Li, M. Lee, N. Kim, G. Wu, D. Deng, J. M. Kim, X. Liu, W. D. Heo, Z. Zi, Spatiotemporal control of TGF-beta signaling with light, ACS Synth. Biol. 7 (2) (2018) 443-451.

42. H. E. Johnson, Y. Goyal, N. L. Pannucci, T. Schupbach, S. Y. Shvartsman, J. E. Toettcher, The Spatiotemporal Limits of Developmental Erk Signaling, Dev. Cell 40 (2) (2017) 185-192.

43. K. Sako, S. J. Pradhan, V. Barone, A. Ingles-Prieto, P. Muller, V. Ruprecht, D. Capek, S. Galande, H. Janovjak, C. P. Heisenberg, Optogenetic control of nodal signaling reveals a temporal pattern of nodal signaling regulating cell fate specification during gastrulation, Cell Rep. 16 (3) (2016) 866-877.

44. S. Zhang, Y. Hu, Y. Huang, H. Xu, G. Wu, H. Dai, Heat shock protein 27 promotes cell proliferation through activator protein-1 in lung cancer, Oncol. Lett. 9 (6) (2015) 2572-2576.

45. D. Reyes, C. Ballare, G. Castellano, D. Soronellas, J. R. Bago, J. Blanco, M. Beato, Activation of mitogen- and stress-activated kinase 1 is required for proliferation of breast cancer cells in response to estrogens or progestins, Oncogene 33 (12) (2014) 1570-1580.

46. C. Gentile, R. C. Muise-Helmericks, C. J. Drake, VEGF-mediated phosphorylation of eNOS regulates angioblast and embryonic endothelial cell proliferation, Dev. Biol. 373 (1) (2013) 163-175.

47. H. Liu, X. Yu, K. Li, J. Klejnot, H. Yang, D. Lisiero, C. Lin, Photoexcited CRY2 interacts with CIB1 to regulate transcription and floral initiation in *Arabidopsis*, Science 322 (5907) (2008) 1535-1539.

48. X. Gao, M. Nowak-Imialek, X. Chen, D. Chen, D. Herrmann, D. Ruan, A. C. H. Chen, M. A. Eckersley-Maslin, S. Ahmad, Y. L. Lee, T. Kobayashi, D. Ryan, J. Zhong, J. Zhu, J. Wu, G. Lan, S. Petkov, J. Yang, L. Antunes, L. S. Campos, B. Fu, S. Wang, Y. Yong, X. Wang, S. G. Xue, L. Ge, Z. Liu, Y. Huang, T. Nie, P. Li, D. Wu, D. Pei, Y. Zhang, L. Lu, F. Yang, S. J. Kimber, W. Reik, X. Zou, Z. Shang, L. Lai, A. Surani, P. P. L. Tam, A. Ahmed, W. S. B. Yeung, S. A. Teichmann, H. Niemann, P. Liu, Establishment of porcine and human expanded potential stem cells, Nat. Cell Biol. 21 (6) (2019) 687-699.

49. G. Chen, D. R. Gulbranson, Z. Hou, J. M. Bolin, V. Ruotti, M. D. Probasco, K. Smuga-Otto, S. E. Howden, N. R. Diol, N. E. Propson, R. Wagner, G. O. Lee, J. Antosiewicz-Bourget, J. M. Teng, J. A. Thomson, Chemically defined conditions for human iPSC derivation and culture, Nat. Methods 8 (5) (2011) 424-429.

50. J. H. Stockley, K. Evans, M. Matthey, K. Volbracht, S. Agathou, J. Mukanowa, J. Burrone, R. T. Karadottir, Surpassing light-induced cell damage in vitro with novel cell culture media, Sci. Rep. 7 (1) (2017) 849.

51. S. L. Liu, K. Gasteratos, Assessing cell-based animal proteins, Science 363 (6429) (2019) 826.

52. E. Dolgin, Sizzling interest in lab-grown meat belies lack of basic research, Nature 566 (7743) (2019) 161-162.

53. H. Ledford, Quest to use CRISPR against disease gains ground, Nature 577 (7789) (2020) 156.

54. E. A. Stadtmauer, J. A. Fraietta, M. M. Davis, A. D. Cohen, K. L. Weber, E. Lancaster, P. A. Mangan, I. Kulikovskaya, M. Gupta, F. Chen, L. Tian, V. E. Gonzalez, J. Xu, I. Y. Jung, J. J. Melenhorst, G. Plesa, J. Shea, T. Matlawski, A. Cervini, A. L. Gaymon, S. Desjardins, A. Lamontagne, J. Salas-Mckee, A. Fesnak, D. L. Siegel, B. L. Levine, J. K. Jadlowsky, R. M. Young, A. Chew, W. T. Hwang, E. O. Hexner, B. M. Carreno, C. L. Nobles, F. D. Bushman, K. R. Parker, Y. Qi, A. T. Satpathy, H. Y. Chang, Y. Zhao, S. F. Lacey, C. H. June, CRISPR-engineered T cells in patients with refractory cancer, Science 367 (6481) (2020).

55. L. Xu, J. Wang, Y. Liu, L. Xie, B. Su, D. Mou, L. Wang, T. Liu, X. Wang, B. Zhang, L. Zhao, L. Hu, H. Ning, Y. Zhang, K. Deng, L. Liu, X. Lu, T. Zhang, J. Xu, C. Li, H. Wu, H. Deng, H. Chen, CRISPR-edited stem cells in a patient with hiv and acute lymphocytic leukemia, N. Engl. J. Med. 381 (13) (2019) 1240-1247.

56. A. V. Anzalone, P. B. Randolph, J. R. Davis, A. A. Sousa, L. W. Koblan, J. M. Levy, P. J. Chen, C. Wilson, G. A. Newby, A. Raguram, D. R. Liu, Search-and-replace genome editing without double-strand breaks or donor DNA, Nature 576 (7785) (2019) 149-157.

57. B. P. Kleinstiver, V. Pattanayak, M. S. Prew, S. Q. Tsai, N. T. Nguyen, Z. Zheng, J. K. Joung, High-fidelity CRISPR-Cas9 nucleases with no detectable genome-wide off-target effects, Nature 529 (7587) (2016) 490-495.

58. F. A. Ran, P. D. Hsu, C. Y. Lin, J. S. Gootenberg, S. Konermann, A. E. Trevino, D. A. Scott, A. Inoue, S. Matoba, Y. Zhang, F. Zhang, Double nicking by RNA-guided CRISPR Cas9 for enhanced genome editing specificity, Cell 154 (6) (2013) 1380-1389.

That which is claimed:

1. A vector comprising a nucleotide sequence encoding a fusion protein comprising the intracellular domain of fibroblast growth factor 1 receptor (FGFR1) and a photoactivatable domain, wherein the vector comprises the nucleotide sequence of SEQ ID NO: 1.

2. The vector of claim 1, wherein the fusion protein comprises a signal peptide.

3. The vector of claim 2, wherein the signal peptide comprises a myristoylation signal peptide (Myr).

4. The vector of claim 3, wherein the Myr comprises the amino acid sequence of SEQ ID NO: 4.

5. The vector of claim 1, wherein the intracellular domain of FGFR1 comprises the amino acid sequence of SEQ ID NO: 6.

6. The vector of claim 1, wherein the photoactivatable domain comprises the light-oxygen-voltage sensing (LOV) domain.

7. The vector of claim 6, wherein the LOV comprises the amino acid sequence of SEQ ID NO: 8.

8. A pluripotent stem cell (PSC) comprising the vector of claim 1.

9. A fibroblast growth factor 2 (FGF2) free pluripotent stem cell (PSC) culture system comprising a PSC comprising a vector comprising a nucleotide sequence encoding a fusion protein comprising the intracellular domain of fibroblast growth factor 1 receptor (FGFR1) and a photoactivatable domain, wherein the vector comprises the nucleotide sequence of SEQ ID NO: 1; and a cell culture illumination source capable of illuminating the PSC with a selected wavelength and intensity of light.

10. The FGF2 free PSC culture system of claim 9, wherein the cell culture illumination source comprises a cell culture substrate, an upper and lower enclosure, one or more illumination sources, one or more circuit boards, and a microcontroller.

11. The FGF2 free PSC culture system of claim 10, wherein the one or more illumination sources can vary the wavelength of the illumination.

12. The FGF2 free PSC culture system of claim 10, wherein the one or more illumination sources emit light at a wavelength of about 470 nm.

13. The FGF2 free PSC culture system of claim 10, wherein the one or more illumination sources comprise one or more light emitting diodes (LEDs).

14. The FGF2 free PSC culture system of claim 10, wherein the one or more illumination sources continuously illuminate the PSC for a period of time between about 1 minute and about 120 minutes.

15. The FGF2 free PSC culture system of claim 14, wherein the one or more illumination sources illuminate the PSC in a time interval of between about 30 minutes to about 4 hours.

16. The FGF2 free PSC culture system of claim 10, wherein the one or more illumination sources illuminate the PSC at an intensity of between about 0.1 $\mu W/mm^2$ to about 25 $\mu W/mm^2$.

17. The FGF2 free PSC culture system of claim 10, wherein the microcontroller is controlled through a computer server via either a wireless or wired computer client.

* * * * *

SEQUENCE LISTING

<160> NUMBER OF SEQ ID NOS: 61

<210> SEQ ID NO 1
<211> LENGTH: 5206
<212> TYPE: DNA
<213> ORGANISM: Artificial Sequence
<220> FEATURE:
<223> OTHER INFORMATION: AAV-Myr-opto-FGFR-LOV
<220> FEATURE:
<221> NAME/KEY: misc_feature
<222> LOCATION: (1790)..(2373)
<223> OTHER INFORMATION: promoter
<220> FEATURE:
<221> NAME/KEY: misc_feature
<222> LOCATION: (2496)..(2537)
<223> OTHER INFORMATION: Myr signal peptide
<220> FEATURE:
<221> NAME/KEY: misc_feature
<222> LOCATION: (2544)..(3815)
<223> OTHER INFORMATION: FGFR1
<220> FEATURE:
<221> NAME/KEY: misc_feature
<222> LOCATION: (3828)..(4262)
<223> OTHER INFORMATION: LOV

<400> SEQUENCE: 1

```
tgctttctct gaccagcatt ctctcccctg ggcctgtgcc gctttctgtc tgcagcttgt      60
ggcctgggtc acctctacgg ctggcccaga tccttccctg ccgcctcctt caggttccgt     120
cttcctccac tccctcttcc ccttgctctc tgctgtgttg ctgcccaagg atgctctttc     180
cggagcactt ccttctcggc gctgcaccac gtgatgtcct ctgagcggat cctccccgtg     240
tctgggtcct ctccgggcat ctctcctccc tcacccaacc ccatgccgtc ttcactcgct     300
gggttcccctt ttccttctcc ttctggggcc tgtgccatct ctcgtttctt aggatggcct    360
tctccgacgg atgtctccct tgcgtcccgc ctccccttct tgtaggcctg catcatcacc     420
gttttctgg acaaccccaa agtaccccgt ctccctggcc ttagccacct ctccatcctc     480
ttgctttctt tgcctggaca ccccgttctc ctgtggattc gggtcacctc tcactccttt     540
catttgggca gctcccctac cccccttacc tctctagtct gtgctagctc ttccagcccc     600
ctgtcatggc atcttccagg ggtccgagag ctcagctagt cttcttcctc caacccgggc     660
ccctatgtcc acttcaggac agcatgtttg ctgcctccag ggatcctgtg tccccgagct     720
gggaccacct tatattccca gggccggtta atgtggctct ggttctgggt acttttatct     780
gtcccctcca ccccacagtg gggcaagctt ctgacctctt ctcttcctcc cacagggcct     840
cgagagatct ggcagcggag agggcagagg aagtcttcta acatgcggtg acgtggagga     900
gaatcccggc cctaggctcg agatgaccga gtacaagccc acggtgcgcc tcgccacccg     960
cgacgacgtc cccagggccg tacgcaccct cgccgccgcg ttcgccgact accccgccac    1020
gcgccacacc gtcgatccgg accgccacat cgagcgggtc accgagctgc aagaactctt    1080
cctcacgcgc gtcgggctcg acatcggcaa ggtgtgggtc gcggacgacg gcgccgcggt    1140
ggcggtctgg accacgccgg agagcgtcga agcggggggcg gtgttcgccg agatcggccc    1200
gcgcatggcc gagttgagcg gttcccggct ggccgcgcag caacagatgg aaggcctcct    1260
ggcgccgcac cggcccaagg agcccgcgtg gttcctggcc accgtcggcg tctcgcccga    1320
ccaccagggc aagggtctgg gcagcgccgt cgtgctcccc ggagtggagg cggccgagcg    1380
cgccggggtg cccgccttcc tggagacctc cgcgccccgc aacctcccct tctacgagcg    1440
gctcggcttc accgtcaccg ccgacgtcga ggtgcccgaa ggaccgcgca cctggtgcat    1500
gacccgcaag cccggtgcct gatctagagg gcccgtttaa acccgctgat cagcctcgac    1560
```

```
tgtgccttct agttgccagc catctgttgt ttgcccctcc cccgtgcctt ccttgaccct    1620
ggaaggtgcc actcccactg tcctttccta ataaaatgag gaaattgcat cgcattgtct    1680
gagtaggtgt cattctattc tggggggtgg ggtggggcag gacagcaagg gggaggattg    1740
ggaagacaat agcaggcatg ctgggatgc ggtgggctct atgggtctcg acattgatta     1800
ttgactagtt attaatagta atcaattacg ggtcattag ttcatagccc atatatggag     1860
ttccgcgtta cataacttac ggtaaatggc ccgcctggct gaccgcccaa cgaccccgc     1920 ccattgacgt caataatgac gtatgttccc atagtaacgc caatagggac tttccattga    1980
cgtcaatggg tggagtattt acggtaaact gcccacttgg cagtacatca agtgtatcat    2040
atgccaagta cgcccctat tgacgtcaat gacggtaaat ggcccgcctg gcattatgcc     2100
cagtacatga cctatgggga ctttcctact tggcagtaca tctacgtatt agtcatcgct    2160
attaccatgg tgatgcggtt ttggcagtac atcaatgggc gtggatagcg gtttgactca    2220
cggggatttc caagtctcca ccccattgac gtcaatggga gtttgttttg gcaccaaaat    2280
caacgggact ttccaaaatg tcgtaacaac tccgccccat tgacgcaaat gggcggtagg    2340
cgtgtacggt gggaggtcta taagcagag ctctctggc taactagaga acccactgct       2400
tactggctta tcgaaattaa tacgactcac tatagggaga cacaagctgg ctagcgttta    2460
aacgggccct ctagactcga gcggccgcgg ccaccatggg gagtagcaag agcaagccta    2520 aggacccag ccagcgcctc gacatgaaga gcggcaccaa gaagagcgac ttccatagcc      2580
agatggctgt gcacaagctg gccaagagca tccctctgcg cagacaggta acagtgtcag    2640
ctgactccag tgcatccatg aactctgggg ttctcctggt tcggccctca cggctctcct    2700
ccagcgggac ccccatgctg gctggagtct ccgaatatga gctccctgag gatccccgct    2760
gggagctgcc acgagacaga ctggtcttag gcaaaccact ggcgagggc tgcttcgggc     2820 aggtggtgtt ggctgaggcc atcggctgg ataaggacaa acccaaccgt gtgaccaaag      2880
tggccgtgaa gatgttgaag tccgacgcaa cggagaagga cctgtcggat ctgatctcgg    2940
agatggagat gatgaaaatg attgggaagc acaagaatat catcaaccct ctgggagcgt    3000
gcacacagga tggtcctctt tatgtcattg tggagtacgc ctccaaaggc aatctccggg    3060
agtatctaca ggcccggagg cctcctgggc tggagtactg ctataacccc agccacaacc    3120
ccgaggaaca gctgtcttcc aaagatctgg tatcctgtgc ctatcaggtg gctcggggca    3180
tggagtatct tgcctctaag aagtgtatac accgagacct ggctgctagg aacgtcctgg    3240
tgaccgagga taacgtaatg aagatcgcag actttggctt agctcgagac attcatcata    3300
tcgactacta caagaaaacc accaacggcc ggctgcctgt gaagtggatg gcccctgagg    3360
cgttgtttga ccgatctac acaccaga gcgatgtgtg gtcttttgga gtgctcttgt        3420
gggagatctt cactctgggt ggctccccat accccggtgt gcctgtggag aacttttca     3480 agctgctgaa ggagggtcat cgaatggaca agcccagtaa ctgtaccaat gagctgtaca    3540
tgatgatgcg ggactgctgg catgcagtgc cctctcagag acctacgttc aagcagttgg    3600
tggaagacct ggaccgcatt gtggccttga cctccaacca ggagtatctg gacctgtcca    3660
taccgctgga ccagtactca cccagctttc ccgacacacg gagctccacc tgctcctcag    3720 ggaggactc tgtcttctct catgagccgt tacctgagga gccctgtctg cctcgacacc     3780
ccacccagct tgccaacagt ggactcaaac ggcgcgtcga gaccggtcct gactacagtc    3840
tcgtgaaggc tctgcaaatg gcacaacaga atttgtcat tacagacgcc tccctcccag      3900
```

```
acaaccctat cgtctacgcc agtagagggt ttctgacact gacaggctat tctctcgacc    3960
agatcctggg caggaactgc aggtttctgc aagggccaga aacagaccca agagctgtgg    4020
ataagatcag gaatgccatc accaaaggcg ttgataccag tgtctgtctg ctgaattata    4080
gacaggatgg cacaaccttc tggaatctct tcttcgtggc tggactcaga gattctaagg    4140
gcaatattgt caactacgtc ggagtgcagt caaaggtgag cgaagattat gccaagctgc    4200
tggtcaacga gcagaacatt gagtacaaag gtgtgcgcac cagtaacatg ctgcgcagaa    4260
agcccggtgg atccggagtc gactatccgt acgacgtacc agactacgca ctcgactaag    4320
aattccacca cactggacta gtggatccga gctcggtacc aagcttaaga ctagggacag    4380
gattggtgac agaaaagccc catccttagg cctcctcctt cctagtctcc tgatattggg    4440
tctaaccccc acctcctgtt aggcagattc cttatctggt gacacacccc catttcctgg    4500
agccatctct ctccttgcca gaacctctaa ggtttgctta cgatggagcc agagaggatc    4560
ctgggaggga gagcttggca gggggtggga gggaagggg ggatgcgtga cctgcccggt    4620
tctcagtggc caccctgcgc taccctctcc cagaacctga gctgctctga cgcggctgtc    4680
tggtgcgttt cactgatcct ggtgctgcag cttccttaca cttcccaaga ggagaagcag    4740 tttgaaaaa caaatcaga ataagttggt cctgagttct aactttggct cttcacctt    4800 ctagtcccca atttatattg ttcctccgtg cgtcagtttt acctgtgaga taaggccagt    4860
agccagcccc gtcctggcag ggctgtggtg aggaggggg tgtccgtgtg aaaactccc    4920 tttgtgagaa tggtgcgtcc taggtgttca ccaggtcgtg gccgcctcta ctccctttct    4980 cttctccat ccttctttcc ttaaagagtc cccagtgcta tctgggacat attcctccgc    5040
ccagagcagg gtcccgcttc cctaaggccc tgctctgggc ttctgggttt gagtccttgg    5100
caagcccagg agaggcgctc aggcttccct gtccccttc ctcgtccacc atctcatgcc    5160
cctggctctc ctgccccttc cctacagggg ttcctggctc tgctct                  5206
```

<210> SEQ ID NO 2
<211> LENGTH: 584
<212> TYPE: DNA
<213> ORGANISM: Artificial Sequence
<220> FEATURE:
<223> OTHER INFORMATION: Promoter of AAV-Myr-opto-FGFR-LOV

<400> SEQUENCE: 2

```
gacattgatt attgactagt tattaatagt aatcaattac ggggtcatta gttcatagcc     60
catatatgga gttccgcgtt acataactta cggtaaatgg cccgcctggc tgaccgccca    120 acgaccccg cccattgacg tcaataatga cgtatgttcc catagtaacg ccaataggga    180
ctttccattg acgtcaatgg gtggagtatt tacggtaaac tgcccacttg gcagtacatc    240
aagtgtatca tatgccaagt acgccccta ttgacgtcaa tgacggtaaa tggcccgcct    300
ggcattatgc ccagtacatg accttatggg actttcctac ttggcagtac atctacgtat    360
tagtcatcgc tattaccatg gtgatgcggt tttggcagta catcaatggg cgtggatagc    420
ggtttgactc acggggattt ccaagtctcc accccattga cgtcaatggg agtttgtttt    480
ggcaccaaaa tcaacgggac tttccaaaat gtcgtaacaa ctccgcccca ttgacgcaaa    540
tgggcggtag gcgtgtacgg tgggaggtct atataagcag agct                     584
```

<210> SEQ ID NO 3
<211> LENGTH: 42
<212> TYPE: DNA
<213> ORGANISM: Artificial Sequence

```
<220> FEATURE:
<223> OTHER INFORMATION: Nucleotide sequence of signal peptide

<400> SEQUENCE: 3
atggggagta gcaagagcaa gcctaaggac cccagccagc gc                         42

<210> SEQ ID NO 4
<211> LENGTH: 14
<212> TYPE: PRT
<213> ORGANISM: Artificial Sequence
<220> FEATURE:
<223> OTHER INFORMATION: Amino acid sequence of signal petpide

<400> SEQUENCE: 4

Met Gly Ser Ser Lys Ser Lys Pro Lys Asp Pro Ser Gln Arg
1               5                   10

<210> SEQ ID NO 5
<211> LENGTH: 1272
<212> TYPE: DNA
<213> ORGANISM: Artificial Sequence
<220> FEATURE:
<223> OTHER INFORMATION: Nucleotide sequence encoding FGFR1

<400> SEQUENCE: 5
atgaagagcg gcaccaagaa gagcgacttc catagccaga tggctgtgca caagctggcc        60
aagagcatcc ctctgcgcag acaggtaaca gtgtcagctg actccagtgc atccatgaac       120
tctggggttc tcctggttcg gccctcacgg ctctcctcca gcggacccc catgctggct        180 ggagtctccg aatatgagct ccctgaggat ccccgctggg agctgccacg agacagactg       240
gtcttaggca aaccacttgg cgagggctgc ttcgggcagg tggtgttggc tgaggccatc       300
gggctggata ggacaaaacc caaccgtgtg accaaagtgg ccgtgaagat gttgaagtcc       360
gacgcaacgg agaaggacct gtcggatctg atctcggaga tggagatgat gaaaatgatt       420
gggaagcaca gaatatcat caaccttctg ggagcgtgca cacaggatgg tcctcttttat       480 gtcattgtgg agtacgcctc caaaggcaat ctccgggagt atctacaggc ccggaggcct       540
cctgggctgg agtactgcta taacccccagc acaaccccg aggaacagct gtcttccaaa       600
gatctggtat cctgtgccta tcaggtggct cggggcatgg agtatcttgc tctaagaag       660 tgtatacacc gagacctggc tgctaggaac gtcctggtga ccgaggataa cgtaatgaag       720
atcgcagact ttggcttagc tcgagacatt catcatatcg actactacaa gaaaaccacc       780
aacggccggc tgcctgtgaa gtggatggcc cctgaggcgt tgtttgaccg gatctacaca       840
caccagagcg atgtgtggtc ttttggagtg ctcttgtggg agatcttcac tctgggtggc       900
tccccatacc ccggtgtgcc tgtggaggaa cttttcaagc tgctgaagga gggtcatcga       960
atggacaagc ccagtaactg taccaatgag ctgtacatga tgatgcggga ctgctggcat      1020
gcagtgccct cagagacc tacgttcaag cagttggtgg aagacctgga ccgcattgtg       1080
gccttgacct ccaaccagga gtatctggac ctgtccatac gctgaccca gtactcaccc      1140 agctttcccg acacacggag ctccaccttc tcctcagggg aggactctgt cttctctcat      1200
gagccgttac ctgaggagcc ctgtctgcct cgacacccca cccagcttgc caacagtgga      1260
ctcaaacggc gc                                                        1272

<210> SEQ ID NO 6
<211> LENGTH: 424
<212> TYPE: PRT
<213> ORGANISM: Artificial Sequence
```

```
<220> FEATURE:
<223> OTHER INFORMATION: Amino acid sequence of FGFR1

<400> SEQUENCE: 6

Met Lys Ser Gly Thr Lys Lys Ser Asp Phe His Ser Gln Met Ala Val
1               5                   10                  15

His Lys Leu Ala Lys Ser Ile Pro Leu Arg Arg Gln Val Thr Val Ser
                20                  25                  30

Ala Asp Ser Ser Ala Ser Met Asn Ser Gly Val Leu Leu Val Arg Pro
            35                  40                  45

Ser Arg Leu Ser Ser Gly Thr Pro Met Leu Ala Gly Val Ser Glu
    50                  55                  60

Tyr Glu Leu Pro Glu Asp Pro Arg Trp Glu Leu Pro Arg Asp Arg Leu
65                  70                  75                  80

Val Leu Gly Lys Pro Leu Gly Glu Gly Cys Phe Gly Gln Val Val Leu
                85                  90                  95

Ala Glu Ala Ile Gly Leu Asp Lys Asp Lys Pro Asn Arg Val Thr Lys
            100                 105                 110

Val Ala Val Lys Met Leu Lys Ser Asp Ala Thr Glu Lys Asp Leu Ser
        115                 120                 125

Asp Leu Ile Ser Glu Met Glu Met Met Lys Met Ile Gly Lys His Lys
    130                 135                 140

Asn Ile Ile Asn Leu Leu Gly Ala Cys Thr Gln Asp Gly Pro Leu Tyr
145                 150                 155                 160

Val Ile Val Glu Tyr Ala Ser Lys Gly Asn Leu Arg Glu Tyr Leu Gln
                165                 170                 175

Ala Arg Arg Pro Pro Gly Leu Glu Tyr Cys Tyr Asn Pro Ser His Asn
            180                 185                 190

Pro Glu Glu Gln Leu Ser Ser Lys Asp Leu Val Ser Cys Ala Tyr Gln
        195                 200                 205

Val Ala Arg Gly Met Glu Tyr Leu Ala Ser Lys Lys Cys Ile His Arg
    210                 215                 220

Asp Leu Ala Ala Arg Asn Val Leu Val Thr Glu Asp Asn Val Met Lys
225                 230                 235                 240

Ile Ala Asp Phe Gly Leu Ala Arg Asp Ile His His Ile Asp Tyr Tyr
                245                 250                 255

Lys Lys Thr Thr Asn Gly Arg Leu Pro Val Lys Trp Met Ala Pro Glu
            260                 265                 270

Ala Leu Phe Asp Arg Ile Tyr Thr His Gln Ser Asp Val Trp Ser Phe
        275                 280                 285

Gly Val Leu Leu Trp Glu Ile Phe Thr Leu Gly Gly Ser Pro Tyr Pro
    290                 295                 300

Gly Val Pro Val Glu Glu Leu Phe Lys Leu Lys Glu Gly His Arg
305                 310                 315                 320

Met Asp Lys Pro Ser Asn Cys Thr Asn Glu Leu Tyr Met Met Arg
                325                 330                 335

Asp Cys Trp His Ala Val Pro Ser Gln Arg Pro Thr Phe Lys Gln Leu
            340                 345                 350

Val Glu Asp Leu Asp Arg Ile Val Ala Leu Thr Ser Asn Gln Glu Tyr
        355                 360                 365

Leu Asp Leu Ser Ile Pro Leu Asp Gln Tyr Ser Pro Ser Phe Pro Asp
    370                 375                 380

Thr Arg Ser Ser Thr Cys Ser Ser Gly Glu Asp Ser Val Phe Ser His
385                 390                 395                 400
```

Glu Pro Leu Pro Glu Glu Pro Cys Leu Pro Arg His Pro Thr Gln Leu
            405                 410                 415

Ala Asn Ser Gly Leu Lys Arg Arg
            420

<210> SEQ ID NO 7
<211> LENGTH: 435
<212> TYPE: DNA
<213> ORGANISM: Artificial Sequence
<220> FEATURE:
<223> OTHER INFORMATION: Nucleotide sequence encoding LOV domain

<400> SEQUENCE: 7
cctgactaca gtctcgtgaa ggctctgcaa atggcacaac agaattttgt cattacagac      60
gcctccctcc cagacaaccc tatcgtctac gccagtagag ggtttctgac actgacaggc     120
tattctctcg accagatcct gggcaggaac tgcaggtttc tgcaagggcc agaaacagac     180
ccaagagctg tggataagat caggaatgcc atcaccaaag gcgttgatac cagtgtctgt     240
ctgctgaatt atagacagga tggcacaacc ttctggaatc tcttcttcgt ggctggactc     300
agagattcta aggcaatat tgtcaactac gtcggagtgc agtcaaaggt gagcgaagat     360
tatgccaagc tgctggtcaa cgagcagaac attgagtaca aggtgtgcg caccagtaac     420 atgctgcgca gaaag                                                     435

<210> SEQ ID NO 8
<211> LENGTH: 145
<212> TYPE: PRT
<213> ORGANISM: Artificial Sequence
<220> FEATURE:
<223> OTHER INFORMATION: Amino acid sequence of LOV domain

<400> SEQUENCE: 8

Pro Asp Tyr Ser Leu Val Lys Ala Leu Gln Met Ala Gln Gln Asn Phe
1               5                   10                  15

Val Ile Thr Asp Ala Ser Leu Pro Asp Asn Pro Ile Val Tyr Ala Ser
            20                  25                  30

Arg Gly Phe Leu Thr Leu Thr Gly Tyr Ser Leu Asp Gln Ile Leu Gly
        35                  40                  45

Arg Asn Cys Arg Phe Leu Gln Gly Pro Glu Thr Asp Pro Arg Ala Val
    50                  55                  60

Asp Lys Ile Arg Asn Ala Ile Thr Lys Gly Val Asp Thr Ser Val Cys
65                  70                  75                  80

Leu Leu Asn Tyr Arg Gln Asp Gly Thr Thr Phe Trp Asn Leu Phe Phe
                85                  90                  95

Val Ala Gly Leu Arg Asp Ser Lys Gly Asn Ile Val Asn Tyr Val Gly
            100                 105                 110

Val Gln Ser Lys Val Ser Glu Asp Tyr Ala Lys Leu Leu Val Asn Glu
        115                 120                 125

Gln Asn Ile Glu Tyr Lys Gly Val Arg Thr Ser Asn Met Leu Arg Arg
    130                 135                 140

Lys
145

<210> SEQ ID NO 9
<211> LENGTH: 20
<212> TYPE: DNA
<213> ORGANISM: Artificial Sequence
<220> FEATURE:

<223> OTHER INFORMATION: guide RNA

<400> SEQUENCE: 9
gtcccctcca ccccacagtg                                        20

<210> SEQ ID NO 10
<211> LENGTH: 20
<212> TYPE: DNA
<213> ORGANISM: Artificial Sequence
<220> FEATURE:
<223> OTHER INFORMATION: pRosa26-gRNA#1

<400> SEQUENCE: 10
cctggcttaa cctgattctt                                        20

<210> SEQ ID NO 11
<211> LENGTH: 20
<212> TYPE: DNA
<213> ORGANISM: Artificial Sequence
<220> FEATURE:
<223> OTHER INFORMATION: pRosa26-gRNA#91

<400> SEQUENCE: 11
gtgagagtta tctgaccgta                                        20

<210> SEQ ID NO 12
<211> LENGTH: 23
<212> TYPE: DNA
<213> ORGANISM: Artificial Sequence
<220> FEATURE:
<223> OTHER INFORMATION: DPPA3 forward primer

<400> SEQUENCE: 12
ttaatccaac ctacatccca ggg                                    23

<210> SEQ ID NO 13
<211> LENGTH: 22
<212> TYPE: DNA
<213> ORGANISM: Artificial Sequence
<220> FEATURE:
<223> OTHER INFORMATION: DPPA3 reverse primer

<400> SEQUENCE: 13
aggggaaaca gattcgctac ta                                     22

<210> SEQ ID NO 14
<211> LENGTH: 24
<212> TYPE: DNA
<213> ORGANISM: Artificial Sequence
<220> FEATURE:
<223> OTHER INFORMATION: ESG1 forward primer

<400> SEQUENCE: 14
atatcccgcc gtgggtgaaa gttc                                   24

<210> SEQ ID NO 15
<211> LENGTH: 24
<212> TYPE: DNA
<213> ORGANISM: Artificial Sequence
<220> FEATURE:
<223> OTHER INFORMATION: ESG1 reverse primer

<400> SEQUENCE: 15
actcagccat ggactggagc atcc                                   24

```
<210> SEQ ID NO 16
<211> LENGTH: 21
<212> TYPE: DNA
<213> ORGANISM: Artificial Sequence
<220> FEATURE:
<223> OTHER INFORMATION: FOXA2 forward primer

<400> SEQUENCE: 16
cgactggagc agctactatg c                                              21

<210> SEQ ID NO 17
<211> LENGTH: 20
<212> TYPE: DNA
<213> ORGANISM: Artificial Sequence
<220> FEATURE:
<223> OTHER INFORMATION: FOXA2 reverse primer

<400> SEQUENCE: 17
tacgtgttca tgccgttcat                                                20

<210> SEQ ID NO 18
<211> LENGTH: 20
<212> TYPE: DNA
<213> ORGANISM: Artificial Sequence
<220> FEATURE:
<223> OTHER INFORMATION: GAPDH forward primer

<400> SEQUENCE: 18
cgagatccct ccaaaatcaa                                                20

<210> SEQ ID NO 19
<211> LENGTH: 20
<212> TYPE: DNA
<213> ORGANISM: Artificial Sequence
<220> FEATURE:
<223> OTHER INFORMATION: GAPDH reverse primer

<400> SEQUENCE: 19
ttctagacgg caggtcaggt                                                20

<210> SEQ ID NO 20
<211> LENGTH: 20
<212> TYPE: DNA
<213> ORGANISM: Artificial Sequence
<220> FEATURE:
<223> OTHER INFORMATION: KLF4 forward primer

<400> SEQUENCE: 20
tcccatcttt ctccacgttc                                                20

<210> SEQ ID NO 21
<211> LENGTH: 20
<212> TYPE: DNA
<213> ORGANISM: Artificial Sequence
<220> FEATURE:
<223> OTHER INFORMATION: KLF4 reverse primer

<400> SEQUENCE: 21
ggatcggata ggtgaagctg                                                20

<210> SEQ ID NO 22
<211> LENGTH: 18
<212> TYPE: DNA
<213> ORGANISM: Artificial Sequence
<220> FEATURE:
<223> OTHER INFORMATION: MSGN1 forward primer
```

```
<400> SEQUENCE: 22
agcgaaggct gcagtgtc                                                 18

<210> SEQ ID NO 23
<211> LENGTH: 20
<212> TYPE: DNA
<213> ORGANISM: Artificial Sequence
<220> FEATURE:
<223> OTHER INFORMATION: MSGN1 reverse primer

<400> SEQUENCE: 23
tggcctctct ggctgtagac                                               20

<210> SEQ ID NO 24
<211> LENGTH: 21
<212> TYPE: DNA
<213> ORGANISM: Artificial Sequence
<220> FEATURE:
<223> OTHER INFORMATION: NANOG forward primer

<400> SEQUENCE: 24
catgagtgtg gatccagctt g                                             21

<210> SEQ ID NO 25
<211> LENGTH: 21
<212> TYPE: DNA
<213> ORGANISM: Artificial Sequence
<220> FEATURE:
<223> OTHER INFORMATION: NANOG reverse primer

<400> SEQUENCE: 25
cctgaataag cagatccatg g                                             21

<210> SEQ ID NO 26
<211> LENGTH: 20
<212> TYPE: DNA
<213> ORGANISM: Artificial Sequence
<220> FEATURE:
<223> OTHER INFORMATION: OCT4 forward primer

<400> SEQUENCE: 26
agtgagaggc aacctggaga                                               20

<210> SEQ ID NO 27
<211> LENGTH: 20
<212> TYPE: DNA
<213> ORGANISM: Artificial Sequence
<220> FEATURE:
<223> OTHER INFORMATION: OCT4 reverse primer

<400> SEQUENCE: 27
acactcggac cacatccttc                                               20

<210> SEQ ID NO 28
<211> LENGTH: 24
<212> TYPE: DNA
<213> ORGANISM: Artificial Sequence
<220> FEATURE:
<223> OTHER INFORMATION: REX1 forward primer

<400> SEQUENCE: 28
cagatcctaa acagctcgca gaat                                          24

<210> SEQ ID NO 29
<211> LENGTH: 23
```

<212> TYPE: DNA
<213> ORGANISM: Artificial Sequence
<220> FEATURE:
<223> OTHER INFORMATION: REX1 reverse primer

<400> SEQUENCE: 29
gcgtacgcaa attaaagtcc aga                                          23

<210> SEQ ID NO 30
<211> LENGTH: 20
<212> TYPE: DNA
<213> ORGANISM: Artificial Sequence
<220> FEATURE:
<223> OTHER INFORMATION: PAX6 forward primer

<400> SEQUENCE: 30
ctttgcttgg gaaatccgag                                              20

<210> SEQ ID NO 31
<211> LENGTH: 20
<212> TYPE: DNA
<213> ORGANISM: Artificial Sequence
<220> FEATURE:
<223> OTHER INFORMATION: PAX6 reverse primer

<400> SEQUENCE: 31
agccaggttg cgaagaactc                                              20

<210> SEQ ID NO 32
<211> LENGTH: 20
<212> TYPE: DNA
<213> ORGANISM: Artificial Sequence
<220> FEATURE:
<223> OTHER INFORMATION: SOX1 forward primer

<400> SEQUENCE: 32
cctcggatct ctggtcaagt                                              20

<210> SEQ ID NO 33
<211> LENGTH: 22
<212> TYPE: DNA
<213> ORGANISM: Artificial Sequence
<220> FEATURE:
<223> OTHER INFORMATION: SOX1 reverse primer

<400> SEQUENCE: 33
gcaggtacat gctgatcatc tc                                           22

<210> SEQ ID NO 34
<211> LENGTH: 26
<212> TYPE: DNA
<213> ORGANISM: Artificial Sequence
<220> FEATURE:
<223> OTHER INFORMATION: SOX2 forward primer

<400> SEQUENCE: 34
gggaaatggg aggggtgcaa aagagg                                       26

<210> SEQ ID NO 35
<211> LENGTH: 26
<212> TYPE: DNA
<213> ORGANISM: Artificial Sequence
<220> FEATURE:
<223> OTHER INFORMATION: SOX2 reverse primer

<400> SEQUENCE: 35

```
ttgcgtgagt gtggatggga ttggtg                                          26
```

<210> SEQ ID NO 36
<211> LENGTH: 20
<212> TYPE: DNA
<213> ORGANISM: Artificial Sequence
<220> FEATURE:
<223> OTHER INFORMATION: SOX17 forward primer

<400> SEQUENCE: 36

```
cgcacggaat ttgaacagta                                                 20
```

<210> SEQ ID NO 37
<211> LENGTH: 20
<212> TYPE: DNA
<213> ORGANISM: Artificial Sequence
<220> FEATURE:
<223> OTHER INFORMATION: SOX17 reverse primer

<400> SEQUENCE: 37

```
ggatcaggga cctgtcacac                                                 20
```

<210> SEQ ID NO 38
<211> LENGTH: 20
<212> TYPE: DNA
<213> ORGANISM: Artificial Sequence
<220> FEATURE:
<223> OTHER INFORMATION: TBX6 forward primer

<400> SEQUENCE: 38

```
aagtaccaac cccgcataca                                                 20
```

<210> SEQ ID NO 39
<211> LENGTH: 20
<212> TYPE: DNA
<213> ORGANISM: Artificial Sequence
<220> FEATURE:
<223> OTHER INFORMATION: TBX6 reverse primer

<400> SEQUENCE: 39

```
taggctgtca cggagatgaa                                                 20
```

<210> SEQ ID NO 40
<211> LENGTH: 19
<212> TYPE: DNA
<213> ORGANISM: Artificial Sequence
<220> FEATURE:
<223> OTHER INFORMATION: pGapdh forward primer

<400> SEQUENCE: 40

```
ctcaacggga agctcactg                                                  19
```

<210> SEQ ID NO 41
<211> LENGTH: 20
<212> TYPE: DNA
<213> ORGANISM: Artificial Sequence
<220> FEATURE:
<223> OTHER INFORMATION: pGapdh reverse primer

<400> SEQUENCE: 41

```
ccctgttgct gtagccaaat                                                 20
```

<210> SEQ ID NO 42
<211> LENGTH: 18
<212> TYPE: DNA
<213> ORGANISM: Artificial Sequence

```
<220> FEATURE:
<223> OTHER INFORMATION: pGata4 forward primer

<400> SEQUENCE: 42
gcttcgcggg ctcctact                                                  18

<210> SEQ ID NO 43
<211> LENGTH: 18
<212> TYPE: DNA
<213> ORGANISM: Artificial Sequence
<220> FEATURE:
<223> OTHER INFORMATION: pGata4 reverse primer

<400> SEQUENCE: 43
ccggttgatg ccattcat                                                  18

<210> SEQ ID NO 44
<211> LENGTH: 20
<212> TYPE: DNA
<213> ORGANISM: Artificial Sequence
<220> FEATURE:
<223> OTHER INFORMATION: pLin28a forward primer

<400> SEQUENCE: 44
tgccggcatc tgtaaatggt                                                20

<210> SEQ ID NO 45
<211> LENGTH: 20
<212> TYPE: DNA
<213> ORGANISM: Artificial Sequence
<220> FEATURE:
<223> OTHER INFORMATION: pLin28a reverse primer

<400> SEQUENCE: 45
gcagtttgca ttccttggca                                                20

<210> SEQ ID NO 46
<211> LENGTH: 20
<212> TYPE: DNA
<213> ORGANISM: Artificial Sequence
<220> FEATURE:
<223> OTHER INFORMATION: pMsgn1 forward primer

<400> SEQUENCE: 46
cgctggagtc ctattcttcg                                                20

<210> SEQ ID NO 47
<211> LENGTH: 20
<212> TYPE: DNA
<213> ORGANISM: Artificial Sequence
<220> FEATURE:
<223> OTHER INFORMATION: pMsgn1 reverse primer

<400> SEQUENCE: 47
gtctgtgagt tccccgatgt                                                20

<210> SEQ ID NO 48
<211> LENGTH: 19
<212> TYPE: DNA
<213> ORGANISM: Artificial Sequence
<220> FEATURE:
<223> OTHER INFORMATION: pNanog forward primer

<400> SEQUENCE: 48
ttgccccgaa gcatccatt                                                 19
```

```
<210> SEQ ID NO 49
<211> LENGTH: 20
<212> TYPE: DNA
<213> ORGANISM: Artificial Sequence
<220> FEATURE:
<223> OTHER INFORMATION: pNanog reverse primer

<400> SEQUENCE: 49
ccagctctga ttaccccaca                                                    20

<210> SEQ ID NO 50
<211> LENGTH: 20
<212> TYPE: DNA
<213> ORGANISM: Artificial Sequence
<220> FEATURE:
<223> OTHER INFORMATION: pPax6 forward primer

<400> SEQUENCE: 50
agttcttcgc aacctggcta                                                    20

<210> SEQ ID NO 51
<211> LENGTH: 20
<212> TYPE: DNA
<213> ORGANISM: Artificial Sequence
<220> FEATURE:
<223> OTHER INFORMATION: pPax6 reverse primer

<400> SEQUENCE: 51
catttggccc ttcgattaga                                                    20

<210> SEQ ID NO 52
<211> LENGTH: 20
<212> TYPE: DNA
<213> ORGANISM: Artificial Sequence
<220> FEATURE:
<223> OTHER INFORMATION: pOct4 forward primer

<400> SEQUENCE: 52
tgaggctttg cagctcagtt                                                    20

<210> SEQ ID NO 53
<211> LENGTH: 20
<212> TYPE: DNA
<213> ORGANISM: Artificial Sequence
<220> FEATURE:
<223> OTHER INFORMATION: pOct4 reverse primer

<400> SEQUENCE: 53
actgcttgat cgtttgccct                                                    20

<210> SEQ ID NO 54
<211> LENGTH: 20
<212> TYPE: DNA
<213> ORGANISM: Artificial Sequence
<220> FEATURE:
<223> OTHER INFORMATION: pSox1 forward primer

<400> SEQUENCE: 54
cacccggatt acaagtaccg                                                    20

<210> SEQ ID NO 55
<211> LENGTH: 20
<212> TYPE: DNA
<213> ORGANISM: Artificial Sequence
<220> FEATURE:
<223> OTHER INFORMATION: pSox1 reverse primer
```

```
<400> SEQUENCE: 55
gagttggaga tggggctgta                                          20

<210> SEQ ID NO 56
<211> LENGTH: 20
<212> TYPE: DNA
<213> ORGANISM: Artificial Sequence
<220> FEATURE:
<223> OTHER INFORMATION: pSox2 forward primer

<400> SEQUENCE: 56
taagtacaca ctgcccggag                                          20

<210> SEQ ID NO 57
<211> LENGTH: 20
<212> TYPE: DNA
<213> ORGANISM: Artificial Sequence
<220> FEATURE:
<223> OTHER INFORMATION: pSox2 reverse primer

<400> SEQUENCE: 57
catggaaccg agcgtcatgc                                          20

<210> SEQ ID NO 58
<211> LENGTH: 20
<212> TYPE: DNA
<213> ORGANISM: Artificial Sequence
<220> FEATURE:
<223> OTHER INFORMATION: pSox17 forward primer

<400> SEQUENCE: 58
tcggggacat gaagatgaag                                          20

<210> SEQ ID NO 59
<211> LENGTH: 19
<212> TYPE: DNA
<213> ORGANISM: Artificial Sequence
<220> FEATURE:
<223> OTHER INFORMATION: pSox17 reverse primer

<400> SEQUENCE: 59
gcggccggta cttgtagtt                                           19

<210> SEQ ID NO 60
<211> LENGTH: 20
<212> TYPE: DNA
<213> ORGANISM: Artificial Sequence
<220> FEATURE:
<223> OTHER INFORMATION: pTbx6 forward primer

<400> SEQUENCE: 60
agtatcagcc ccgcatacac                                          20

<210> SEQ ID NO 61
<211> LENGTH: 20
<212> TYPE: DNA
<213> ORGANISM: Artificial Sequence
<220> FEATURE:
<223> OTHER INFORMATION: pTbx6 reverse primer

<400> SEQUENCE: 61
ctgctcggga tctgactctc                                          20
```